(12) United States Patent
Schiller et al.

(10) Patent No.: US 7,807,458 B2
(45) Date of Patent: Oct. 5, 2010

(54) MULTILINEAGE-INDUCIBLE CELLS AND USES THEREOF

(75) Inventors: Paul C. Schiller, Miami Beach, FL (US); Gianluca D'Ippolito, North Miami Beach, FL (US)

(73) Assignees: The United States of America as represented by the Secretary of the Department of Veterans Affairs, Washington, DC (US); The University of Miami, Miami, FL (US)

(*) Notice: Subject to any disclaimer, the term of this patent is extended or adjusted under 35 U.S.C. 154(b) by 959 days.

(21) Appl. No.: 10/544,021

(22) PCT Filed: Jan. 29, 2004

(86) PCT No.: PCT/US2004/002580

§ 371 (c)(1), (2), (4) Date: Jul. 28, 2005

(87) PCT Pub. No.: WO2004/069172

PCT Pub. Date: Aug. 19, 2004

(65) Prior Publication Data

US 2006/0147426 A1 Jul. 6, 2006

Related U.S. Application Data

(60) Provisional application No. 60/443,572, filed on Jan. 30, 2003.

(51) Int. Cl.
C12N 5/00 (2006.01)
C12N 5/02 (2006.01)
C12N 5/06 (2006.01)
C12N 5/08 (2006.01)

(52) U.S. Cl. ........................ 435/325; 435/377; 435/372

(58) Field of Classification Search .................. None
See application file for complete search history.

(56) References Cited

U.S. PATENT DOCUMENTS

| | | |
|---|---|---|
| 6,261,549 B1 | 7/2001 | Fernandez et al. |
| 6,387,367 B1 | 5/2002 | Davis-Sproul et al. |
| 6,936,281 B2 | 8/2005 | Seshi |
| 7,033,831 B2 * | 4/2006 | Fisk et al. ................... 435/377 |
| 7,056,738 B2 * | 6/2006 | Prockop et al. ............. 435/372 |
| 7,101,710 B2 | 9/2006 | Tsai et al. |
| 7,252,995 B2 | 8/2007 | Fu et al. |
| 2002/0168765 A1 | 11/2002 | Prockop et al. |
| 2003/0161818 A1 | 8/2003 | Weiss et al. |
| 2003/0166272 A1 | 9/2003 | Abuljadayel |
| 2003/0211602 A1 | 11/2003 | Atala |
| 2003/0219898 A1 | 11/2003 | Sugaya et al. |
| 2004/0058412 A1 | 3/2004 | Ho et al. |
| 2004/0121464 A1 | 6/2004 | Rathjen et al. |
| 2004/0137612 A1 | 7/2004 | Baksh et al. |
| 2004/0224401 A1 | 11/2004 | Ludwig et al. |
| 2004/0258669 A1 | 12/2004 | Dzau et al. |
| 2005/0054098 A1 | 3/2005 | Mistry et al. |
| 2005/0058631 A1 | 3/2005 | Kihm et al. |
| 2005/0084959 A1 | 4/2005 | Hamada et al. |
| 2005/0118712 A1 | 6/2005 | Tsai et al. |
| 2005/0164380 A1 | 7/2005 | Trisler et al. |
| 2005/0181502 A1 | 8/2005 | Furcht et al. |
| 2005/0255588 A1 * | 11/2005 | Young et al. ................. 435/366 |
| 2006/0040392 A1 | 2/2006 | Collins et al. |
| 2006/0057657 A1 | 3/2006 | Baetscher et al. |
| 2006/0073124 A1 | 4/2006 | Garcia Castro et al. |
| 2006/0078993 A1 | 4/2006 | Phan et al. |
| 2006/0088890 A1 | 4/2006 | Simmons |
| 2006/0093586 A1 | 5/2006 | Musick |
| 2006/0147426 A1 | 7/2006 | Schiller et al. |
| 2006/0177932 A1 | 8/2006 | Nakauchi et al. |
| 2006/0182724 A1 | 8/2006 | Riordan et al. |
| 2006/0223177 A1 | 10/2006 | Harris et al. |
| 2007/0014771 A1 | 1/2007 | Mistry et al. |
| 2007/0020757 A1 | 1/2007 | Zhang et al. |
| 2007/0053885 A1 | 3/2007 | Nishikawa et al. |
| 2007/0054399 A1 | 3/2007 | Kim et al. |
| 2007/0072294 A1 | 3/2007 | Doronin et al. |
| 2007/0077201 A1 | 4/2007 | Reading et al. |
| 2007/0077649 A1 | 4/2007 | Sammak et al. |
| 2007/0077652 A1 | 4/2007 | Peled et al. |

(Continued)

FOREIGN PATENT DOCUMENTS

WO   WO 0121767 A2 *   3/2001

OTHER PUBLICATIONS

Lennon et al., (2001) J. Cell. Physiol. 187, 345-355.*

(Continued)

*Primary Examiner*—Daniel C Gamett
(74) *Attorney, Agent, or Firm*—Nixon & Vanderhye P.C.

(57) ABSTRACT

Described herein are post natal, multilineage inducible cells (MIAMI cells). In some examples, the cells are isolated from non fractionated, adult (males and females 3 to 72 years old) human bone marrow under cell culture conditions, which are believed to resemble an in vivo niche microenvironment in which primitive multipotent cells exist. MIAMI cells have a unique profile of molecular markers, and can be maintained in vitro (for more than 50 population doublings) without detectable changes in their characteristic molecular profile. MIAMI cells can be differentiated into mesodermal, neuroectodermal, and endodermal cell lineages. Methods of isolating, differentiating and using MIAMI cells are also described.

64 Claims, 12 Drawing Sheets

U.S. PATENT DOCUMENTS

| | | | |
|---|---|---|---|
| 2007/0092967 | A1 | 4/2007 | Han et al. |
| 2007/0098699 | A1 | 5/2007 | Rudd |
| 2007/0105221 | A1 | 5/2007 | Han et al. |
| 2007/0128722 | A1 | 6/2007 | Lin et al. |
| 2007/0160583 | A1 | 7/2007 | Lange et al. |
| 2007/0178591 | A1 | 8/2007 | Honmou et al. |
| 2007/0212336 | A1 | 9/2007 | Fulkerson et al. |
| 2007/0218548 | A1 | 9/2007 | Nishikawa et al. |
| 2007/0219526 | A1 | 9/2007 | Freyman |

OTHER PUBLICATIONS

Blazar et al., Blood. Jun. 1986;67(6):1655-1660.*
Aubin (J Cell Biochem. Mar. 1, 1999;72(3):396-410).*
Kuznetsov et al., Br J Haematol. Jun. 1997;97(3):561-570.*
Young et al., The Anatomical Record Part A: Discoveries in Molecular, Cellular, and Evolutionary Biology, vol. 277A, Issue 1, pp. 178-203 Published Online: Feb. 10, 2004.*
Int'l Search Report for related Appln. No. PCT/US2004/002580 dated Dec. 8, 2005.
Int'l Preliminary Report on Patentability for related Appln. No. PCT/US2004/002580 dated Apr. 10, 2006.
D'Ippolito et al., "Age-Related Osteogenic Potential of Mesenchymal Stromal Stem Cells from Human Vertebral Bone Marrow," *Journal of Bone and Mineral Research* 14(7):1115-1122, 1999.
Galimi et al., "Hepatocyte Growth Factor Induces Proliferation and Differentiation of Multipotent and Erythroid Hemopoietic Progenitors," *The Journal of Cell Biology* 127(6):1743-1754, 1994.
Schwartz et al., "Multipotent adult progenitor cells from bone marrow differentiate into functional hepatocyte-like cells," *The Journal of Clinical Investigation* 109(10):1291-1302, 2002.

* cited by examiner

STEP 1: Specification (bFGF; 1 day)

STEP 2: Commitment (NT-3/βME; 2 days)

STEP 3: Differentiation (NT-3/BDNF/NGF; 3-7 days)

SEQUENCE LISTING

<160> NUMBER OF SEQ ID NOS: 32

<210> SEQ ID NO 1
<211> LENGTH: 22
<212> TYPE: DNA
<213> ORGANISM: artificial sequence
<220> FEATURE:
<223> OTHER INFORMATION: Primer

<400> SEQUENCE: 1
agccagtctc accttcaacc gc                                              22

<210> SEQ ID NO 2
<211> LENGTH: 20
<212> TYPE: DNA
<213> ORGANISM: artificial sequence
<220> FEATURE:
<223> OTHER INFORMATION: Primer

<400> SEQUENCE: 2
ggagtagcag agggaggccg                                                 20

<210> SEQ ID NO 3
<211> LENGTH: 22
<212> TYPE: DNA
<213> ORGANISM: artificial sequence
<220> FEATURE:
<223> OTHER INFORMATION: Primer

```
<400> SEQUENCE: 3
aggtgattat cctgaaccat cc                                              22

<210> SEQ ID NO 4
<211> LENGTH: 22
<212> TYPE: DNA
<213> ORGANISM: artificial sequence
<220> FEATURE:
<223> OTHER INFORMATION: Primer

<400> SEQUENCE: 4
aaaggtggat agtctgagaa gc                                              22

<210> SEQ ID NO 5
<211> LENGTH: 16
<212> TYPE: DNA
<213> ORGANISM: artificial sequence
<220> FEATURE:
<223> OTHER INFORMATION: Primer

<400> SEQUENCE: 5
catgagagcc ctcaca                                                     16

<210> SEQ ID NO 6
<211> LENGTH: 17
<212> TYPE: DNA
<213> ORGANISM: artificial sequence
<220> FEATURE:
<223> OTHER INFORMATION: Primer

<400> SEQUENCE: 6
agagcgacac cctagac                                                    17

<210> SEQ ID NO 7
<211> LENGTH: 20
<212> TYPE: DNA
<213> ORGANISM: artificial sequence
<220> FEATURE:
<223> OTHER INFORMATION: Primer

<400> SEQUENCE: 7
tcagcatttt gggaatggcc                                                 20

<210> SEQ ID NO 8
<211> LENGTH: 20
<212> TYPE: DNA
<213> ORGANISM: artificial sequence
<220> FEATURE:
<223> OTHER INFORMATION: Primer

<400> SEQUENCE: 8
gaggttgttg tcttcgaggt                                                 20

<210> SEQ ID NO 9
<211> LENGTH: 20
<212> TYPE: DNA
<213> ORGANISM: artificial sequence
<220> FEATURE:
<223> OTHER INFORMATION: Primer

<400> SEQUENCE: 9
ccaagtaagt ccaavgaaag                                                 20

<210> SEQ ID NO 10
```

```
<211> LENGTH: 19
<212> TYPE: DNA
<213> ORGANISM: artificial sequence
<220> FEATURE:
<223> OTHER INFORMATION: Primer

<400> SEQUENCE: 10
ggtgatgtcc tcgtctgta                                                  19

<210> SEQ ID NO 11
<211> LENGTH: 20
<212> TYPE: DNA
<213> ORGANISM: artificial sequence
<220> FEATURE:
<223> OTHER INFORMATION: Primer

<400> SEQUENCE: 11
gtttgttctc tgaccgcctc                                                 20

<210> SEQ ID NO 12
<211> LENGTH: 19
<212> TYPE: DNA
<213> ORGANISM: artificial sequence
<220> FEATURE:
<223> OTHER INFORMATION: Primer

<400> SEQUENCE: 12
ccagttctga agcacctga                                                  19

<210> SEQ ID NO 13
<211> LENGTH: 21
<212> TYPE: DNA
<213> ORGANISM: artificial sequence
<220> FEATURE:
<223> OTHER INFORMATION: Primer

<400> SEQUENCE: 13
aaccagattg agagcatccg c                                               21

<210> SEQ ID NO 14
<211> LENGTH: 21
<212> TYPE: DNA
<213> ORGANISM: artificial sequence
<220> FEATURE:
<223> OTHER INFORMATION: Primer

<400> SEQUENCE: 14
ccttcagggc agtgtacgtg a                                               21

<210> SEQ ID NO 15
<211> LENGTH: 24
<212> TYPE: DNA
<213> ORGANISM: artificial sequence
<220> FEATURE:
<223> OTHER INFORMATION: Primer

<400> SEQUENCE: 15
attctcctat tgacccagaa agcg                                            24

<210> SEQ ID NO 16
<211> LENGTH: 26
<212> TYPE: DNA
<213> ORGANISM: artificial sequence
<220> FEATURE:
<223> OTHER INFORMATION: Primer

<400> SEQUENCE: 16
```
agctttatct ccacagacac gacatt        26

<210> SEQ ID NO 17
<211> LENGTH: 21
<212> TYPE: DNA
<213> ORGANISM: artificial sequence
<220> FEATURE:
<223> OTHER INFORMATION: Primer

<400> SEQUENCE: 17
gagatttctc tgtatggcac c        21

<210> SEQ ID NO 18
<211> LENGTH: 21
<212> TYPE: DNA
<213> ORGANISM: artificial sequence
<220> FEATURE:
<223> OTHER INFORMATION: Primer

<400> SEQUENCE: 18
ctgcaaatga gacactttct c        21

<210> SEQ ID NO 19
<211> LENGTH: 20
<212> TYPE: DNA
<213> ORGANISM: artificial sequence
<220> FEATURE:
<223> OTHER INFORMATION: Primer

<400> SEQUENCE: 19
caacaaacaa aacgcaaaac        20

<210> SEQ ID NO 20
<211> LENGTH: 19
<212> TYPE: DNA
<213> ORGANISM: artificial sequence
<220> FEATURE:
<223> OTHER INFORMATION: Primer

<400> SEQUENCE: 20
aagtcaaaca caatcccga        19

<210> SEQ ID NO 21
<211> LENGTH: 21
<212> TYPE: DNA
<213> ORGANISM: artificial sequence
<220> FEATURE:
<223> OTHER INFORMATION: Primer

<400> SEQUENCE: 21
ctggagaaga ctttcgaaca a        21

<210> SEQ ID NO 22
<211> LENGTH: 21
<212> TYPE: DNA
<213> ORGANISM: artificial sequence
<220> FEATURE:
<223> OTHER INFORMATION: Primer

<400> SEQUENCE: 22
agaggcttat tgtagtcgtc g        21

<210> SEQ ID NO 23
<211> LENGTH: 19
<212> TYPE: DNA

```
<213> ORGANISM: artificial sequence
<220> FEATURE:
<223> OTHER INFORMATION: Primer

<400> SEQUENCE: 23
tctttcaaac acgaaccgt                                                   19

<210> SEQ ID NO 24
<211> LENGTH: 21
<212> TYPE: DNA
<213> ORGANISM: artificial sequence
<220> FEATURE:
<223> OTHER INFORMATION: Primer

<400> SEQUENCE: 24 gcctttgta aacacgacag t                                                 21

<210> SEQ ID NO 25
<211> LENGTH: 20
<212> TYPE: DNA
<213> ORGANISM: artificial sequence
<220> FEATURE:
<223> OTHER INFORMATION: Primer

<400> SEQUENCE: 25
atctggactc caggcgtgcc                                                  20

<210> SEQ ID NO 26
<211> LENGTH: 20
<212> TYPE: DNA
<213> ORGANISM: artificial sequence
<220> FEATURE:
<223> OTHER INFORMATION: Primer

<400> SEQUENCE: 26
agcaatgaat tccttggcag                                                  20

<210> SEQ ID NO 27
<211> LENGTH: 16
<212> TYPE: DNA
<213> ORGANISM: artificial sequence
<220> FEATURE:
<223> OTHER INFORMATION: Primer

<400> SEQUENCE: 27
aggcttcttc tacaca                                                      16

<210> SEQ ID NO 28
<211> LENGTH: 16
<212> TYPE: DNA
<213> ORGANISM: artificial sequence
<220> FEATURE:
<223> OTHER INFORMATION: Primer

<400> SEQUENCE: 28
caggctgcct gcacca                                                      16

<210> SEQ ID NO 29
<211> LENGTH: 20
<212> TYPE: DNA
<213> ORGANISM: artificial sequence
<220> FEATURE:
<223> OTHER INFORMATION: Primer

<400> SEQUENCE: 29
cgaccatctg ccgctttgag                                                  20
```

```
<210> SEQ ID NO 30
<211> LENGTH: 20
<212> TYPE: DNA
<213> ORGANISM: artificial sequence
<220> FEATURE:
<223> OTHER INFORMATION: Primer

<400> SEQUENCE: 30
ccccctgtcc cccattccta                                               20

<210> SEQ ID NO 31
<211> LENGTH: 24
<212> TYPE: DNA
<213> ORGANISM: artificial sequence
<220> FEATURE:
<223> OTHER INFORMATION: Primer

<400> SEQUENCE: 31
cagatcctaa acagctcgca gaat                                          24

<210> SEQ ID NO 32
<211> LENGTH: 23
<212> TYPE: DNA
<213> ORGANISM: artificial sequence
<220> FEATURE:
<223> OTHER INFORMATION: Primer

<400> SEQUENCE: 32
gcgtacgcaa attaaagtcc aga                                           23
```

MULTILINEAGE-INDUCIBLE CELLS AND USES THEREOF

CROSS REFERENCE TO RELATED APPLICATIONS

This is a §371 U.S. national stage of PCT application No. PCT/US2004/002580, which claims the benefit of U.S. Provisional Application No. 60/443,572, filed Jan. 30, 2003, each of which applications is incorporated in its entirety herein by reference.

FIELD

This disclosure relates to multilineage-inducible cells isolated from biological sources and methods of isolating, differentiating, and using these cells.

BACKGROUND

Stem cells are unspecialized cells that can self renew indefinitely and also differentiate into more mature cells with specialized functions. Stem cells offer unprecedented opportunities for treatment of debilitating diseases and a new way to explore fundamental questions of biology. Human embryonic stem cells have been shown to develop into multiple tissue types and to exhibit long-term self renewal in culture; however, the use of human embryonic stem cells is controversial, given the diverse views held in society about the moral and legal status of the early embryo. The controversy has prompted scientists to find meaningful post-natal substitutes for embryonic stem cells.

It is now known that cells having at least some of the characteristics of embryonic stem cells are present in after-born individuals, even throughout adulthood. Often called "adult stem cells," these cells can self renew for extended periods of time, and can give rise to cells with specialized morphology and function. Until recently, it was not believed that adult stem cells found in one tissue type (such as, a neural stem cell) would be capable of generating the specialized cell types of another tissue type (such as, a blood cell). Moreover, it was not thought that an adult stem cell could differentiate into a cell type derived from an embryonic germ layer other than the one from which the stem cell derived.

Although primitive cell subpopulations with the potential to differentiate toward various cell lineages have been isolated from post-natal sources, few of such cells can maintain a broad and multilineage differentiation capacity, resembling the plasticity of embryonic stem cells. Additional multipotent post-natal cells, particularly from human sources, are needed, as are new methods of reproducibly isolating such cells.

SUMMARY

Cell culture conditions to isolate post-natal, multilineage inducible cells (MIAMI cells) are disclosed herein. In certain embodiments, such culture conditions may include, for example, extracellular matrix substrate, oxygen tension, growth factors and vitamins, cell density, co-culture of cells, or combinations thereof. The disclosed MIAMI cells have unique molecular profiles. For example, in one embodiment, MIAMI cells express at least one of CD29, CD81, CD90, or SSEA4 in combination with CD122, CD164, hepatocyte growth factor receptor (c-Met), bone morphogenetic protein receptor, type MB (BMP-receptor 1B), neurotrophic tyrosine kinase receptor type 3 (NTRK3), Oct-4, or Rex-1. MIAMI cells (and single-cell-derived colonies thereof) can be maintained in vitro without detectable changes in their characteristic molecular profile. Such in vitro MIAMI cell populations have multi-germ layer differentiation potential and can be differentiated into mesodermal, neuroectodermal, and endodermal cell lineages.

MIAMI cells and differentiated MIAMI cells are useful for, among other things, the treatment of many types of diseases, including, for example, neurological disorders, bone disorders, cartilage disorders, and diabetes.

The foregoing and other features and advantages will become more apparent from the following detailed description of several embodiments, which proceeds with reference to the accompanying figures.

BRIEF DESCRIPTION OF THE FIGURES

FIG. 2A shows FACS analysis profiles of MIAMI cells labeled, as indicated, with antibodies against CD29, CD36, CD49E, CD54, CD56, CD63, CD81, CD90, CD122, CD164, CNTFR, HLA-DR and/or control IgGs. Plots show isotype control IgG-staining profiles (dashed lines) versus specific antibody staining profile (solid lines). FIG. 2B shows a western blot of total protein (10 µg) using an antibody that recognizes human cMet. Expression of the 190 kD precursor and 140 kD cleaved receptor was detected in MIAMI cells and in the PC-3 prostate cancer cell line (positive control). FIGS. 2C and 2D show RT-PCR analysis of mRNA expression of the stem cell markers Oct-4 and Rex-1 (FIG. 2C) and hTERT (FIG. 2D) in MIAMI cell isolates. In FIG. 2D, RNA isolated from the human foreskin fibroblast cell line hTERT-BJ1 was used as positive control (+ve cont). RNA-specific amplification is demonstrated by the absence of a band when reverse transcriptase (RT) was excluded (−RT).

FIG. 4A shows Alizarin red-S staining of hydroxyapatite-associated calcium mineral deposited in the extracellular matrix by osteoblastic cells derived upon osteogenic induction of MIAMI cells.

FIG. 4B shows RT-PCR analysis of transcripts present in osteoblast-induced MIMI cells. MIAMI cells (1-4: different isolates) induced to differentiate to the osteoblastic lineage express the osteoblast phenotypic markers bone sialoprotein (BSP), osteocalcin (OC), runt-homology domain transcription factor Runx2, and osteopontin (OP). The size of the human-specific PCR products and the number of amplification cycles are in parenthesis. BSP and OC transcripts were not detected in uninduced MIAMI cells. Human elongation factor 1-alpha (EF1-α) was used as an internal and loading control for the RT-PCR experiments.

FIG. 5A shows Sudan-IV staining of triglyceride lipid droplets accumulated in the cytoplasm of adipocytic cells derived upon adipocytic induction of MIAMI cells. FIG. 5B shows RT-PCR analysis of transcripts present in adipocyte-induced MIAMI cells. MIAMI cells induced to differentiate to the adipogenic lineage express the adipocytic phenotypic markers lipoprotein lipase (LPL) and pro-adipocytic transcription factor peroxisome proliferator activated receptor γ-2 (PPAR-γ2), detected after 25 amplification cycles. These transcripts were not detected in uninduced MIAMI cells.

Neural-competent MIAMI cells progress through a sequential neuro-induction process of specification (step 1; bFGF), commitment (step 2; βME/NT-3), and differentiation (step 3; NT-3/NGF/BDNF). Each stage is characterized by the stage-specific expression of specific markers. Nestin (top left) is expressed first, followed by induction of β-M-tubulin (TuJ1) and NGF receptor (middle), and then expression of neurofilament-160 (NF160) and neuronal nuclear protein (NeuN) (bottom). Morphologically homogeneous cell populations are observed after each step.

Figure 7:
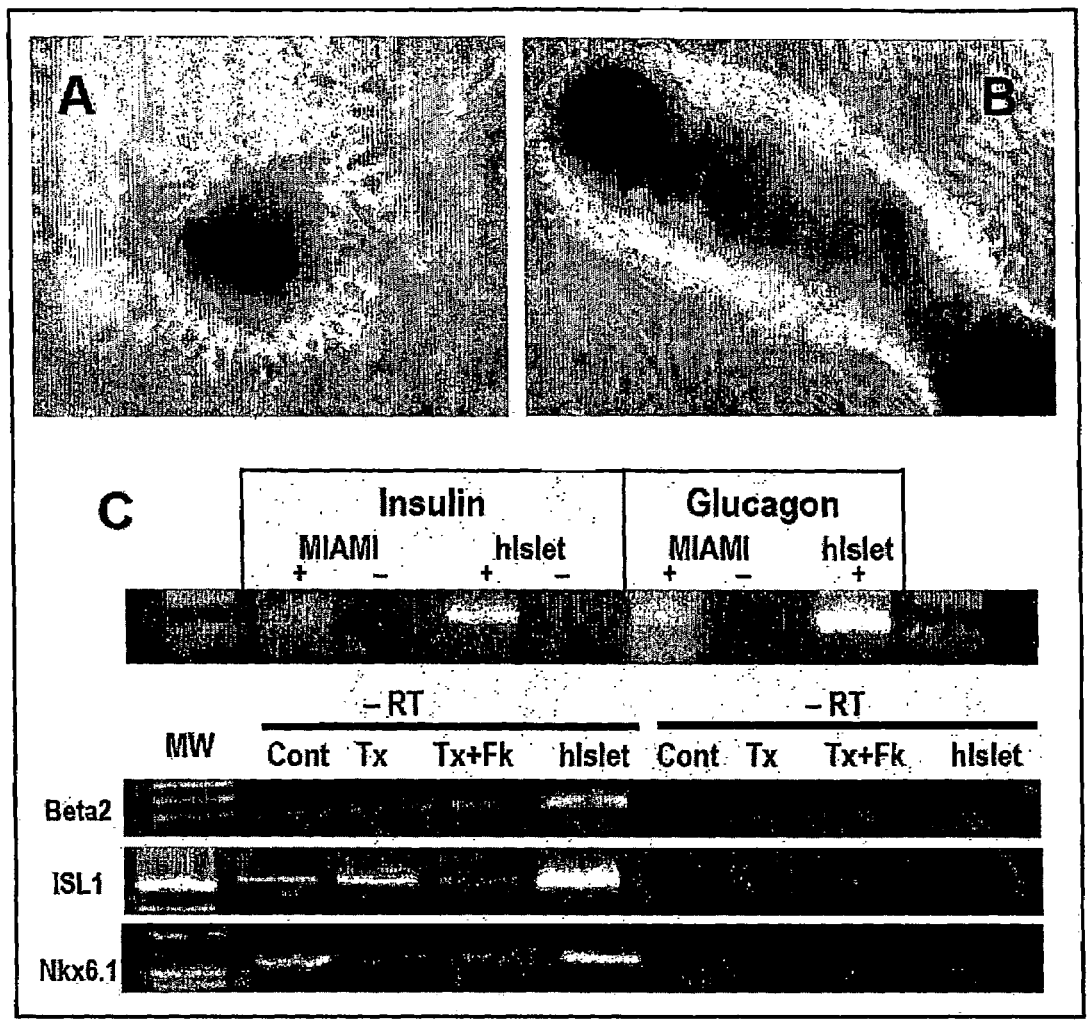

FIG. 7 shows the result of experiments demonstrating that MIAMI cells develop features resembling those of pancreatic islets. MIAMI cells growing as adherent cultures can be induced to grow in an attachment-independent fashion, forming spherical or oblong clusters (FIGS. 7A and B). FIG. 7C shows RT-PCR analysis transcripts isolated from MIAMI cells grown under endodermal-promoting conditions (as described in Example 1). Treated MIAMI cells express transcripts for insulin and glucagon, as do islet (hIslet) positive controls. These islet-specific transcripts were not expressed in MIAMI cells under uninduced conditions. Control (Cont) and treated (Tx) MIAMI also cells expressed Beta2/NeuroD (295 bp), ISL1 (542 bp), and Nkx6.1 (239 bp) transcripts, which demonstrates that these cells are molecularly competent to develop the physiologic phenotype of functional endocrine islet cells. In all cases, bands were detected after 25 amplification cycles. MW: molecular weight markers. Fk: forskolin.

Figure 8:
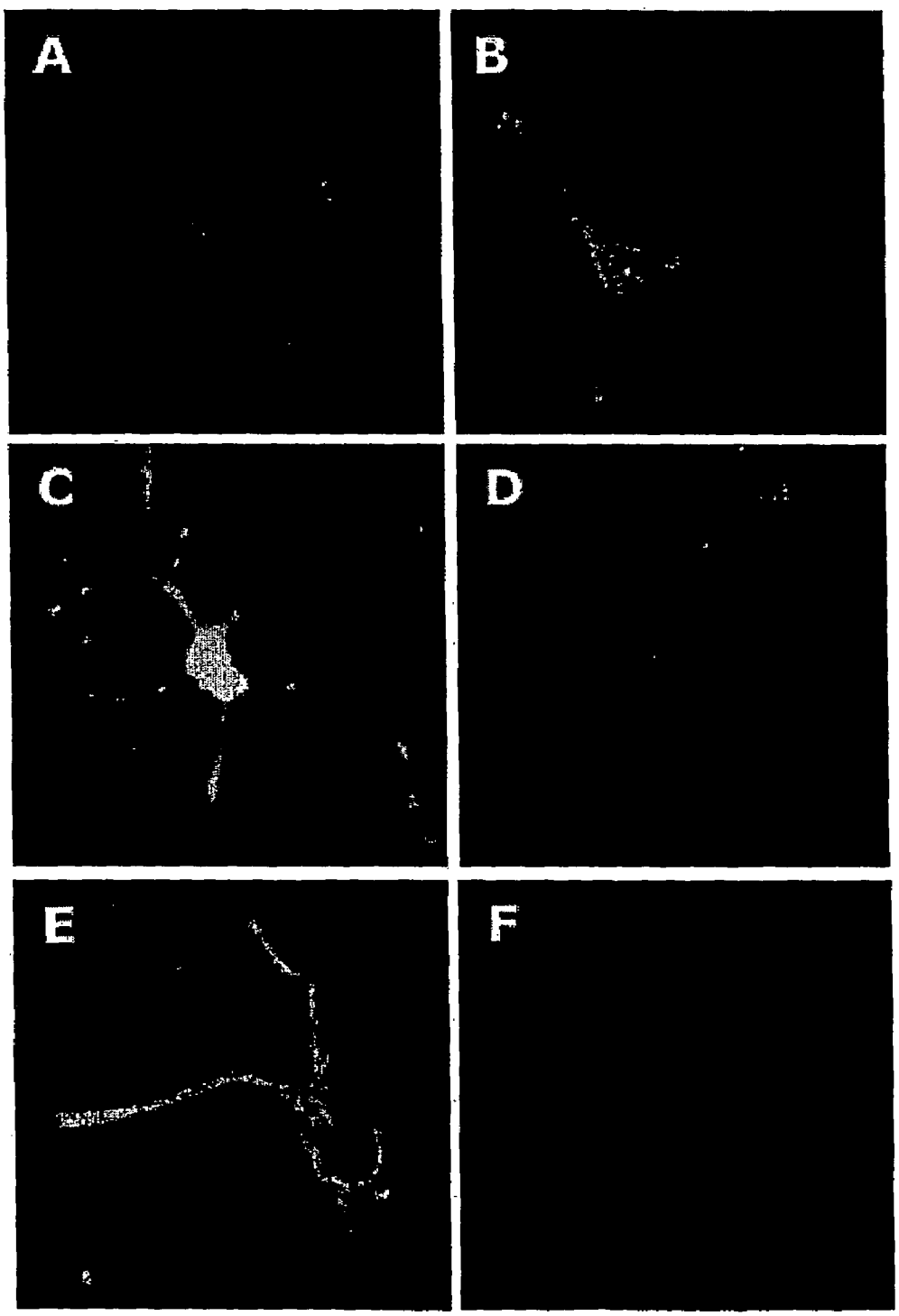

FIG. 8 shows digital photographs of nestin expression during neuronal differentiation of MIAMI cells. In untreated expanded cultures of MIAMI cells very few cells were observed to express low levels of nestin (FIG. 8A). Upon treatment with bFGF (Step 1) expression of nestin was stronger (FIG. 8B) and in a larger fraction of cells. Upon neuronal commitment treatment (bFGF withdrawal and addition of NT-3/β-ME; Step 2) strong nestin expression was detected within 24 hours of induction in cells undergoing morphological changes where processes were becoming elongated (FIG. 8C). However, after 48 hours of the treatment the level of nestin expression decreased to barely detectable levels (FIG. 8D) and was below detection levels after that point. Specific immunostaining was demonstrated in experiments in which fetal brain-derived human neuroepithelial progenitor cells were used as positive controls (FIG. 8E), or in experiments in which primary isotypic antibodies were used as negative controls (FIG. 8F).

Figure 9:
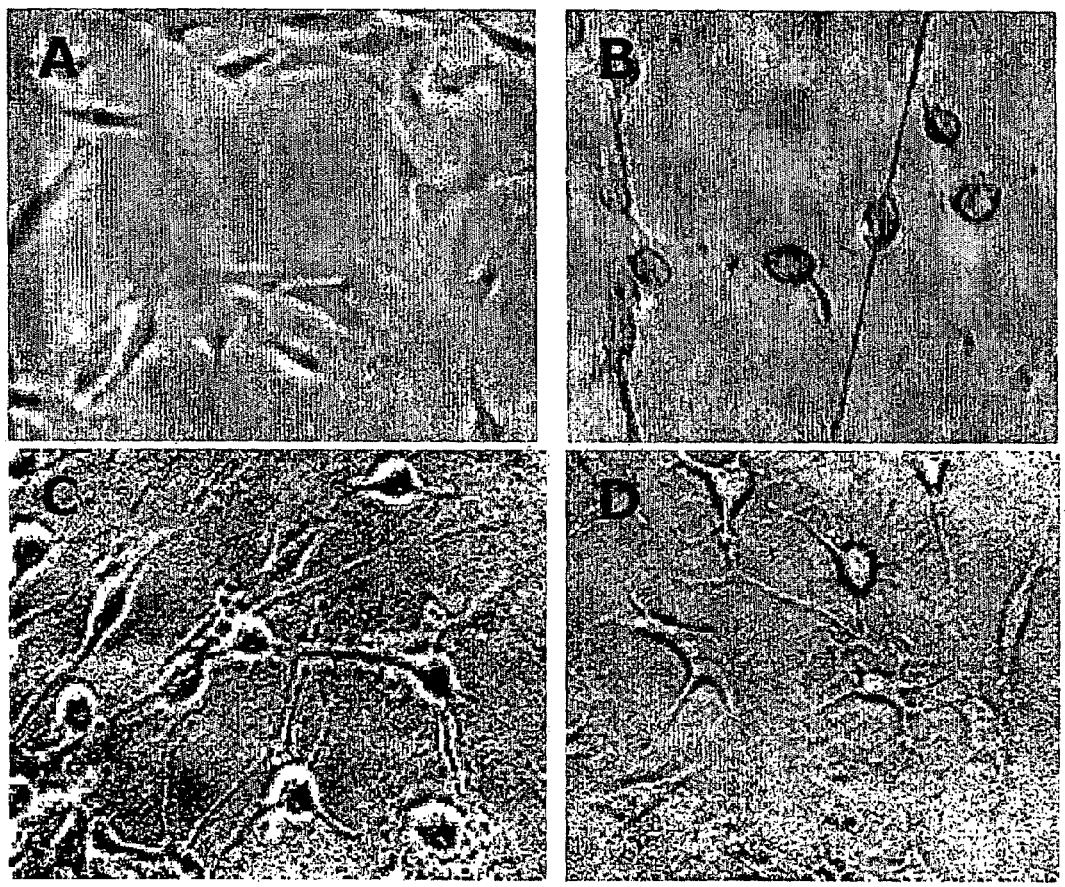

FIG. 9 shows digital photographs of the morphology of MIAMI cells undergoing neuronal differentiation. As shown in FIG. 9A, MIAMI cells have a fibroblastic morphology after 24 hours of plating under conditions for neuronal differentiation described in Example 2. Upon treatment with bFGF (Step 1) cells appear to become somewhat more round. Soon after neuronal commitment (NT-3/β-ME; Step 2) dramatic morphological changes can be observed. Within 5 hours the cells acquired a spherical refractile body and exhibited a typical neuronal perikaryal appearance and bipolar spindle shape (FIG. 9B). At the beginning of the neuronal differentiation process (NT-3/BDNF/NGF; Step 3) a homogeneous population of cells with long and branched neurites can be observed (FIG. 9C). As shown in FIG. 9D, the complexity and length of neurites increases with time in culture, in this instance 3 days after initiating neuronal differentiation.

Figure 10:
Figure 10:
Figure 10:
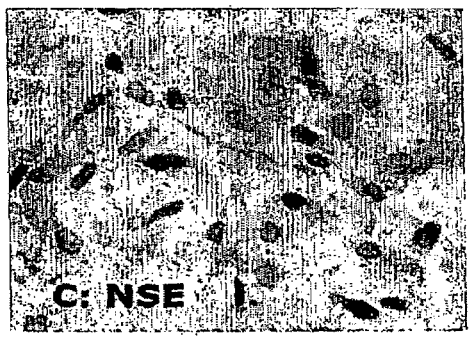
Figure 10:
Figure 10:
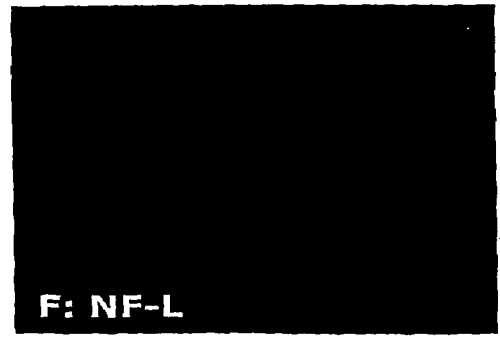
Figure 10:

FIG. 10 shows digital photographs demonstrating the expression of neuronal markers during neuronal differentiation of MIAMI cells. Within 24 hours of plating, the MIAMI cells were exposed to neural specification conditions (Step 1; bFGF) for 1 day, followed by neuronal commitment (NT-3/βME; Step 2) for 2 days, and the neuronal differentiation (NT-3/BDNF/NGF; Step 3) for 3-7 days. At different times during the treatment protocol cells were immunostained with specific antibodies against neural proteins, followed by secondary antibodies conjugated to horseradish peroxidase, rhodamine, or FITC. While expression of the markers examined could not be detected in uninduced MIAMI cell (FIG. 10A), expression of GFAP (FIG. 10B) and NSE (FIG. 10C) was observed in the cells within 24 hours after neural specification treatment. Expression of NGF-receptor (FIG. 10D: TrkA) and neuron-specific class III β-tubulin (FIG. 10E: TuJ1) was observed within 48 hours after initiation of the neuronal commitment step. Later in the cultures (2-4 days) the expression of class III β-tubulin, but not TrkA, was found to decrease. Expression of NF-L (FIG. 10F) and NeuN (FIG. 10G), markers for mature neurons, began to be observed in the majority of the cells shortly after initiation of the neuronal differentiation step and their expression of these markers increased with time.

Figure 11:
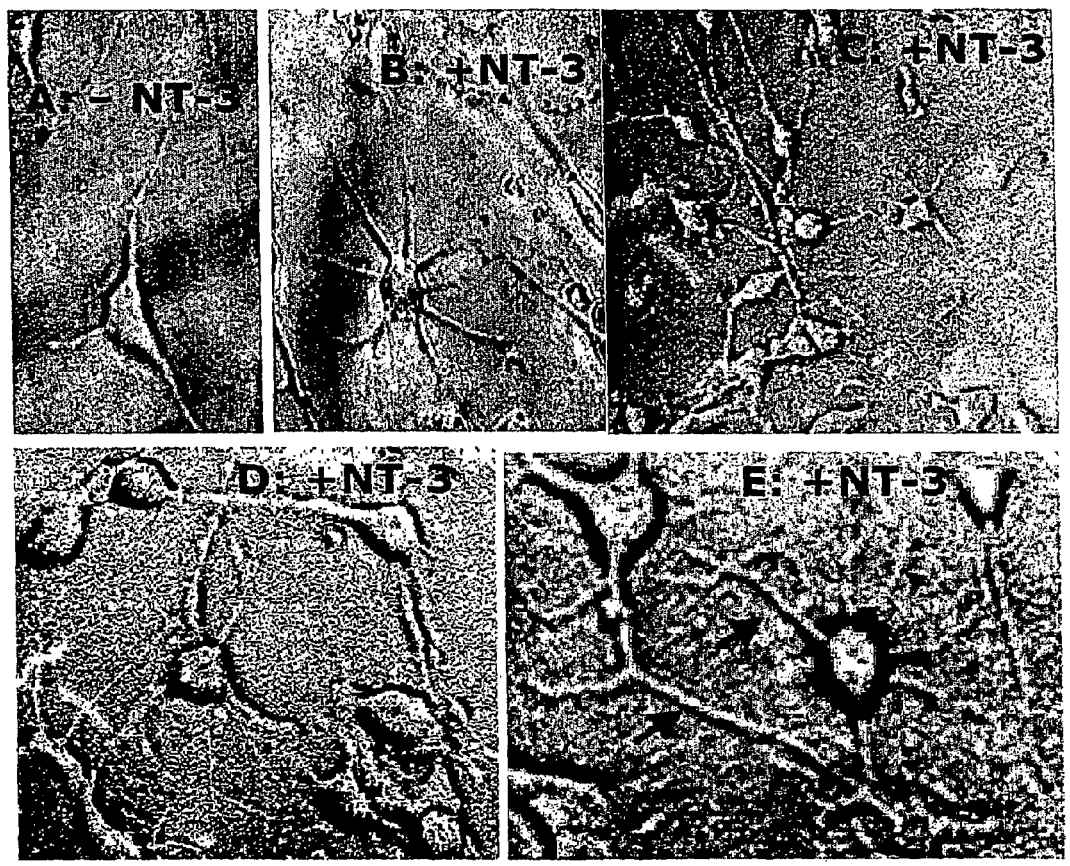

FIG. 11 shows digital photographs demonstrating that neurite growth and arborization of MIAMI-derived neuronal cells is enhanced by NT-3 treatment. When NT-3 was excluded during the commitment step, cells developed a bipolar shape but neurite processes and branching points were rarely observed (FIG. 11A). In the presence of NT-3 the arborization dramatically increased (FIG. 11B) as well as the length of the neurites (FIG. 11C-E). In most cases, numerous long neurites could be observed (arrowheads in FIG. 11E) in neuronal cells found to contain a longer and thicker process (arrows in FIG. 11E).

Figure 12:
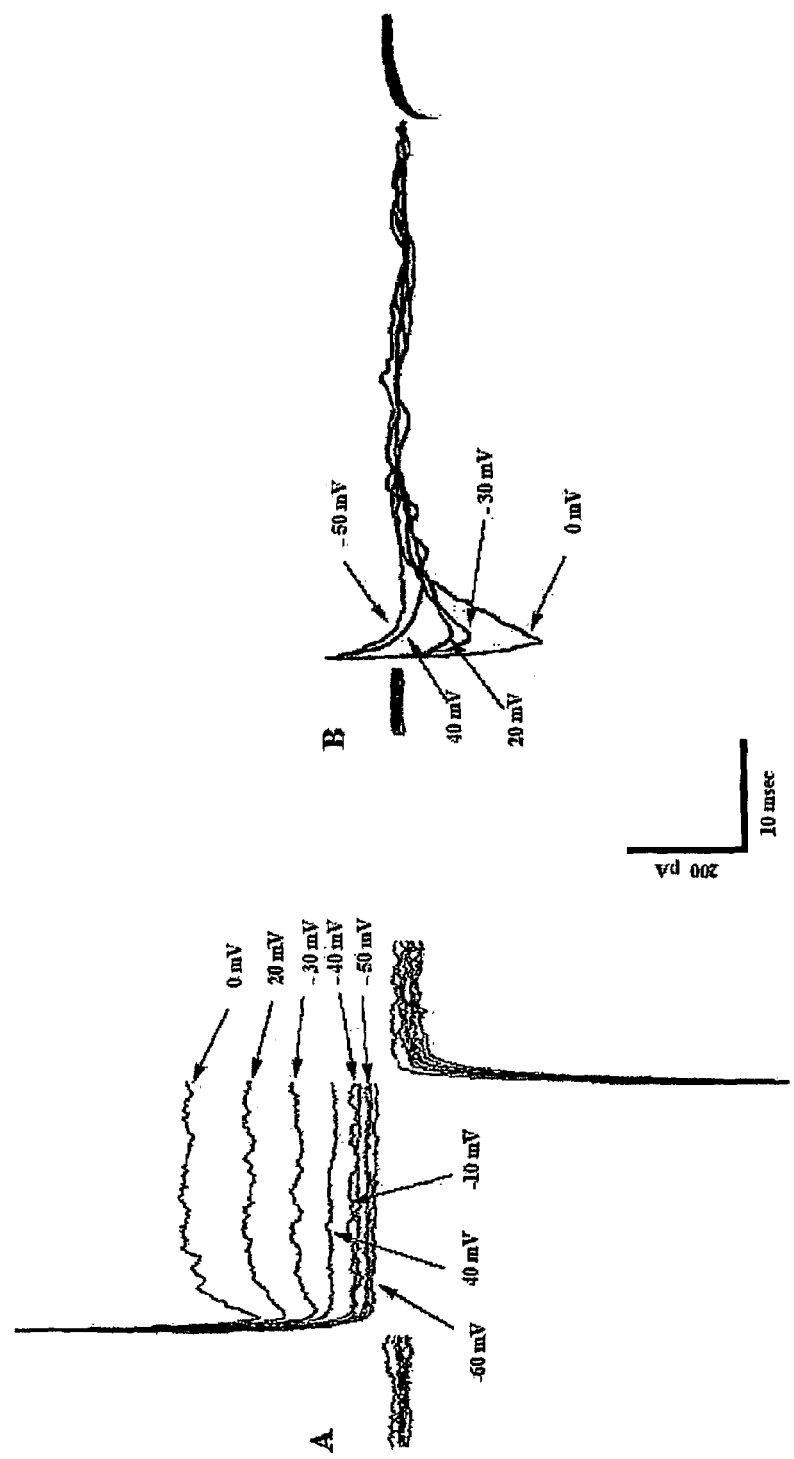

FIG. 12 shows recordings of voltage-activated ion currents in MIAMI-derived neuronal cells. In FIG. 12A, inward, outward and leakage currents were recorded in the MIAMI-derived neuronal cells. Ion currents were recorded without using compensation. FIG. 12B shows potential-activated inward currents recorded in whole-cell configuration from cultured MIAMI-derived neuronal cells. In order to study sodium currents in the absence of potassium currents in the cells KCl in the extracellular and intracellular solutions was replaced with CsCl. Leak currents have been subtracted from signals obtained during the voltage-steps commands. Arrows in A and B show the depolarizing voltage steps. Cells were whole-cell patch clamped at the holding membrane potential −70 mV and currents were activated by 10 mV depolarizing steps.

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. In the accompanying sequence listing:

SEQ ID NO: 1 is a human telomerase reverse transcriptase (Accession No. NM_003219) forward nucleic acid primer (hTERT-F).

SEQ ID NO: 2 is a human telomerase reverse transcriptase (Accession No. NM_003219) reverse nucleic acid primer (hTERT-R).

SEQ ID NO: 3 is a human elongation factor 1-alpha (Accession No. L41490) forward nucleic acid primer (hEF1α-F).

SEQ ID NO: 4 is a human elongation factor 1-alpha (Accession No. L41490) reverse nucleic acid primer (hEF1α-R).

SEQ ID NO: 5 is a human osteocalcin (Accession No. NM_000711) forward nucleic acid primer (hOC-F).

SEQ ID NO: 6 is a human osteocalcin (Accession No. NM_000711) reverse nucleic acid primer (hOC-R).

SEQ ID NO: 7 is a human bone sialoprotein (Accession No. J05213) forward nucleic acid primer (hBSP-F).

SEQ ID NO: 8 is a human bone sialoprotein (Accession No. J05213) reverse nucleic acid primer (hBSP-R).

SEQ ID NO: 9 is a human osteopontin (Accession No. X13694) forward nucleic acid primer (hOP-F).

SEQ ID NO: 10 is a human osteopontin (Accession No. X13694) reverse nucleic acid primer (hOP-R).

SEQ ID NO: 11 is a human runt domain transcription factor Runx2 (Accession No. L40992) forward nucleic acid primer (hRunx2-F).

SEQ ID NO: 12 is a human runt domain transcription factor Runx2 (Accession No. L40992) reverse nucleic acid primer (hRunx2-R).

SEQ ID NO: 13 is a human collagen type II-alpha 1 (Accession No. NM_001844) forward nucleic acid primer (hCOL2A1-F).

SEQ ID NO: 14 is a human collagen type II-alpha 1 (Accession No. NM_001844) reverse nucleic acid primer (hCOL2A1-R).

SEQ ID NO: 15 is a human peroxisome proliferator-activated receptor gamma-2 (Accession No. U79012) forward nucleic acid primer (hPPAR-γ2-F).

SEQ ID NO: 16 is a human peroxisome proliferator-activated receptor gamma-2 (Accession No. U79012) reverse nucleic acid primer (hPPAR-γ2-R).

SEQ ID NO: 17 is a human lipoprotein lipase (Accession No. X14390) forward nucleic acid primer (hLPL-F).

SEQ ID NO: 18 is a human lipoprotein lipase (Accession No. X14390) reverse nucleic acid primer (hLPL-R).

SEQ ID NO: 19 is a human islet-1 transcription factor (ISL-1) (Accession No. BC017027) forward nucleic acid primer (hISL-1-F).

SEQ ID NO: 20 is a human ISL-1 (Accession No. BC017027) reverse nucleic acid primer (hISL-1-R).

SEQ ID NO: 21 is a human NK6 transcription factor related, locus 1 (Accession No. NM_006168) forward nucleic acid primer (hNkx6.1-F).

SEQ ID NO: 22 is a human NK6 transcription factor related, locus 1 (Accession No. NM_006168) reverse nucleic acid primer (hNkx6.1-R).

SEQ ID NO: 23 is a human beta-cell transcription factor Beta2/NeuroD (Accession No. NM_002500) forward nucleic acid primer (hBeta2-F).

SEQ ID NO: 24 is a human beta-cell transcription factor Beta2/NeuroD (Accession No. NM_002500) reverse nucleic acid primer (hBeta2-R).

SEQ ID NO: 25 is a human glucagon (Accession No. NM002054) forward nucleic acid primer (hGLUC-F).

SEQ ID NO: 26 is a human glucagon (Accession No. NM002054) reverse nucleic acid primer (hGLUC-R).

SEQ ID NO: 27 is a human insulin (Accession No. NM_000207) forward nucleic acid primer (hINS-F).

SEQ ID NO: 28 is a human insulin (Accession No. NM_000207) reverse nucleic acid primer (hINS-R).

SEQ ID NO: 29 is a human POU domain, class 5, transcription factor 1 (POU5F1/Oct-4) (Accession No. NM_002701) forward nucleic acid primer.

SEQ ID NO: 30 is a human POU domain, class 5, transcription factor 1 (POU5F1/Oct-4) (Accession No. NM_002701) reverse nucleic acid primer SEQ ID NO: 31 is a human Rex-1 (Accession No. AF450454) forward nucleic acid primer.

SEQ ID NO: 32 is a human Rex-1 (Accession No. AF450454) reverse nucleic acid primer.

DETAILED DESCRIPTION

I. Introduction

Disclosed herein are isolated, post-natal, multilineage-inducible cells, which express at least one of hepatocyte growth factor receptor (c-Met), bone morphogenetic protein receptor, type IB (BMP-receptor 1B), or neurotrophic tyrosine kinase receptor type 3 (NTRK3). In some embodiments, the cells further express at least one of CD29, CD81, CD90, or stage-specific embryonic antigen 4 (SSEA4). The cells may be isolated from a wide range of biological sources, including bone marrow, vertebral bodies, peripheral blood, umbilical cord blood, iliac crest aspirate, bone marrow, vertebral bodies, peripheral blood, umbilical cord blood, iliac crest aspirate, fat, cartilage, muscle, skin, bone, teeth, liver, brain, or mixtures thereof. In particular examples, the biological sample is bone marrow. In other examples, the cell is isolated from a mammal, such as a human. In some examples, the mammal from which the cell is isolated is a postmortem subject.

Also disclosed are isolated, post-natal, multilineage-inducible cells, which express at least one of CD29, CD81, CD90, or stage-specific embryonic antigen 4 (SSEA4), and at least one of CD122, CD164, hepatocyte growth factor receptor (c-Met), bone morphogenetic protein receptor, type IB (IMP-receptor 1B), neurotrophic tyrosine kinase receptor type 3 (NTRK3), Oct-4, or Rex-1. In particular embodiments, isolated, $CD29^+$, $CD81^+$, $CD90^+$, $CD122^+$, $CD164^+$, multilineage-inducible cells are disclosed.

Methods of isolating multilineage-inducible cells are also disclosed. Such methods include culturing a cell population isolated from a biological sample, including bone marrow, vertebral bodies, peripheral blood, umbilical cord blood, iliac crest aspirate, bone marrow, vertebral bodies, peripheral blood, umbilical cord blood, iliac crest aspirate, fat, cartilage, muscle, skin, bone, teeth, liver, brain, or mixtures thereof, under low-oxygen conditions (such as, in certain examples, less than about 3% oxygen) to produce adherent cells and non-adherent cells; removing the non-adherent cells; and expanding the adherent cells. In some methods the biological sample is from a post-natal subject, including, in some embodiments, from a human post-natal subject. In some methods, the adherent cells and the non-adherent cells are co-cultured for at least 7 days, or the cells are placed in a cell culture container, which includes an extracellular matrix (ECM) substrate, such as fibronectin, collagen, laminin, vitronectin, polylysine, heparan sulfate proteoglycans, entactin, or a combination thereof. Multilineage-inducible cells isolated by these methods are also contemplated.

A method of inducing osteogenic differentiation of multilineage-inducible cells by culturing the multilineage-inducible cells in an osteogenic medium is also disclosed. In some embodiments, the osteogenic medium comprises ascorbic acid 2-phosphate, β-glycerophosphate, and dexamethasone. In other embodiments, the method further involves placing the multilineage-inducible cells in a cell culture container, and adding dexamethasone to the osteogenic medium after a portion of the multilineage-inducible cells adhere to the cell culture container. In particular methods, osteogenic differentiation includes the expression of Runx2, osteocalcin, collagen I$\alpha$1, or bone sialoprotein in the multilineage-inducible cells.

Also disclosed herein are methods of inducing chondrogenic differentiation of multilineage-inducible cells by culturing multilineage-inducible cells in a serum-free, chondrogenic medium. In some embodiments, the chondrogenic medium comprises dexamethasone, TGF-β3, ascorbic acid 2-phosphate, sodium pyruvate, proline, insulin, transferrin, and selenous acid. In other embodiments, the method further involves pelleting the cells, which are subsequently suspended in the serum-free, chondrogenic medium, in a tube. In more specific embodiments, the cells are cultured for at least about 4 to 6 weeks.

Methods of inducing adipogenic differentiation of multilineage-inducible cells are also disclosed. Such methods include culturing the multilineage-inducible cells in an adipogenic medium, which, in some examples, includes hydrocortisone, isobutylmethylxanthine, and indomethacine. In some methods, adipogenic differentiation involves expression of lipoprotein lipase or peroxisome proliferators-activated receptor γ-2 in the multilineage-inducible cells.

This disclosure also includes methods of inducing neural differentiation of multilineage-inducible cells, which involves the following steps: (a) contacting the cells with a first culture medium comprising basic fibroblast growth factor (bFGF); (b) contacting the cells with a second culture medium comprising β-mercaptoethanol (βBME) and neurotrophin-3 (NT-3); and (c) contacting the cells with a third culture medium comprising NT-3, β-nerve growth factor (NGF), and brain-derived neurotrophic factors (BDNF). Some methods further include plating the cells at low density in a cell culture container, which includes an ECM substrate (such as fibronectin, collagen, laminin, vitronectin, polylysine, heparan sulfate proteoglycans, entactin, or a combination thereof), prior to step (a). In particular embodiments, step (b) has a duration of up to about 48 hours, or step (c) has a duration of up to about 2 days, or step (d) has a duration of up to about 14 days.

Methods of inducing endodermal differentiation of multilineage-inducible cells are also disclosed. Such methods include (a) contacting the cells to a first culture medium comprising bFGF; (b) contacting the cells to a second culture medium comprising DMSO, butylated hydroxyanisole (BHA), and exendin-4; (c) contacting the cells to a third culture medium comprising bFGF, EGF, and exendin-4; and (d) contacting the cells to a fourth culture medium comprising nicotinamide, HGF, exendin-4, and activin-A. Specific method embodiments further include plating the cells at low density prior to step (a). In yet other embodiments, the cells are contacted with the first culture medium for up to about 24 hours, or the cells are contacted with the second culture medium for up to about 24 hours, or the cells are contacted with the third culture medium for up to about 4 days, or the cells are contacted with the fourth culture medium for up to about 14 days.

Also disclosed herein are methods of treating a disorder, such as, but not limited to, a neurological disorder, a bone disorder, a cartilage disorder, or diabetes, in a subject by administering a therapeutically effective amount of a disclosed multilineage-inducible cell. Some methods further include inducing the cells to differentiate, for example, inducing neural differentiation, osteogenic differentiation, chondrogenic differentiation, or β-cell-like differentiation in the cells. In some methods, the cells are introduced locally into a subject, or, in other examples, the cells introduced systemically into the subject. Specific neurological disorders include Parkinson's Huntington's disease, Alzheimer's disease, epilepsy, familial dysautonomia, schizophrenia, amyotrophic lateral sclerosis, Lewy body dementia, multiple sclerosis, cerebellar ataxia, progressive supranuclear palsy, anxiety disorder, obsessive compulsive disorder, attention deficit disorder, Tourette Syndrome, Tay Sachs, Nieman Pick, HIV encephalopathy, spinal cord injury, or stroke. Specific bone disorders, which may be treated by the disclosed methods, include arthritis, osteoporosis, osteosclerotic metaphyseal dysplasia, osteomyelitis, Paget's disease of bone, hypophosphatasia, osteopetrosis, osteomalacia, or bone fracture. Specific cartilage disorders, which may be treated by the disclosed methods, include arthritis, pseudoachondroplasia, articular cartilage degeneration, osteogenesis imperfecta, or a cartilage tear.

Methods for fat augmentation in a subject are also disclosed. Such methods include administering an amount of multilineage-inducible cells disclosed herein sufficient to augment fat in the subject. In some of these methods, adipogenic differentiation is induced in the cells. In other methods, the cells may be introduced locally into a region of the body where fat augmentation is desired.

Pharmaceutical compositions including disclosed multilineage-inducible cells in a pharmaceutically acceptable carrier are also disclosed herein.

Further disclosed herein are methods of identifying a differentiation-inducing agent including providing multilineage-inducible cells disclosed herein; contacting the cells with the agent; and observing the effect of the agent on the cells, wherein differentiation of the cells identifies the agent as differentiation inducing. In specific embodiments differentiation of the cells includes assaying expression of an osteogenic marker, a chondrogenic marker, an adipogenic marker, a neural marker, an endodermal marker, or a combination thereof, or assaying a functional property of an osteogenic cell, a chondrogenic cell, an adipogenic cell, a neural cell, or a β-cell.

Kits including a container containing a purified population of multilineage-inducible cells described herein are also disclosed.

II. Abbreviations

α-MEM α-minimum essential medium
BDNF brain-derived neurotrophic factors
Beta2/NeuroD neurogenic differentiation transcription factor (also, beta-cell E-box transactivator 2)

bFGF basic fibroblast growth factor
BHA butylated hydroxyanisole
βME β-mercaptoethanol
BMMNCs bone marrow mononuclear cells
BMP-receptor 1B bone morphogenetic protein receptor, type IB
BSP bone sialoprotein
c-Met HGF receptor
CNTFR ciliary neurotrophic factor receptor
DMEM Dulbecco's modified Eagle medium
DMSO dimethyl sulfoxide
ECM extracellular matrix
EF1-α translation elongation factor 1-alpha
EGF epidermal growth factor
ES embryonic stem [cells]
FACS fluorescence-activated cell sorting
FBS fetal bovine serum
FN fibronectin
GFAP glial fibrillary acidic protein
GlyA glycophorin-A
HGF hepatocyte growth factor
ISL-1 islet-1 transcription factor
LPL lipoprotein lipase
MAPCs multipotent adult progenitor cells
MSCs marrow stromal cells
NeuN neuronal nuclear protein
NF160 neurofilament-160 kD
NF-L neurofilament protein, light chain (68 kD)
NF-M 125 kD neurofilament protein
NGF β-nerve growth factor
Nkx6.1 NK6 transcription factor related, locus 1
NSCs neural stem cells
NT-3 neurotrophin-3
NTRK3 NT-3 receptor
OC osteocalcin
OP osteopontin
PPAR-γ2 peroxisome proliferator activated receptor γ-2
Runx2 runt-homology domain transcription factor
SSEA4 stage-specific embryonic antigen 4
TGF-β3 transforming growth factor-β3
Trk-A tyrosine kinase receptor A (also, NGF receptor)
TuJ1 monoclonal antibody specific for β-III-tubulin III. Terms Unless otherwise noted, technical terms are used according to conventional usage. Definitions of common terms in molecular biology may be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

In order to facilitate review of the various embodiments of the invention, the following explanations of specific terms are provided:

Adherent: Connected to, associated with, or affixed to, a substrate. For example, a cell that adheres to a cell culture dish in vitro, and grows attached thereto is adherent. Typically, an adherent cell will not wash off a surface to which it is attached by gentle washing with a buffered saline solution. In some cases, enzymatic solutions (such as trypsin-EDTA) may be used to disrupt the attachment between an adherent cell and the surface to which it is attached. In other circumstances, adherent cells may be physically detached from a surface using a tool designed for such purposes, such as a cell scraper.

A non-adherent cell is one that is not stably connected to, associated with, or affixed to a substrate. Cells grown in suspension culture are examples of non-adherent cells.

β cells: Mature insulin producing cells. In vivo, these cells are found in the pancreatic islets of Langerhans. "β-like cells" are cells that express one or more markers characteristic of β cells, such as Nkx6.1 or insulin.

Biological Sample: Any sample that may be obtained directly or indirectly from a living or postmortem subject (such as, a recently deceased), including whole blood, plasma, serum, bone marrow, vertebral bodies, iliac crest aspirate, umbilical cord blood, tears, mucus, saliva, urine, pleural fluid, spinal fluid, gastric fluid, sweat, semen, vaginal secretion, sputum, fluid from ulcers and/or other surface eruptions, blisters, abscesses, and/or extracts of tissues, cells or organs (such as, fat, cartilage, muscle, skin, bone, teeth, liver, brain). The biological sample may also be a laboratory research sample such as a cell culture supernatant. The sample is collected or obtained using methods well known to those skilled in the art.

Bone morphogenetic protein receptor, type IB (BMP-receptor 1B or BMPR1B): A member of a family of transmembrane serine/threonine kinases, which are receptors for members of the TGF-β superfamily. Human BMPR1B cDNA encodes a 502-amino acid polypeptide that contains a single transmembrane domain and an intracellular serine/threonine kinase domain. BMPR1B mRNA is about 6.5 kb and is expressed in several human tissues, with highest levels in prostate and brain. BMPR1B is also known as activin receptor-like kinase 6 (or ALK6). (See, for example, ten Dijke et al., *Science*, 264:101-104, 1994; Ide et al., *Oncogene*, 14:1377-1382, 1997; Ide et al., *Cytogenet. Cell Genet.*, 81:285-286, 1998).

CD13: An antigen of between about 150-170 kD, which is expressed, for example, in myelomonocytic cells. CD13 is a zinc metalloproteinase, and is also known as amino peptidase N.

CD29: A 130-kD antigen expressed, for example, in leukocytes. CD29 is also known as the β1-integrin subunit, which associates with CD49a in VLA-1 integrin. Alternate names for CD29 include Fibronectin Receptor, Beta Subunit (FNRβ), Very Late Activation Protein, Beta (VLA-β).

CD49b: A 165 kD antigen expressed, for example, in B cells, monocytes, and platelets.

CD49b is also known as the α2-integrin subunit. It associates with CD29 (the β1-integrin subunit) to bind collagen and laminin. Alternate names for CD49b are Very Late Activation Protein 2 Receptor, VLA-2 Receptor, or Platelet Glycoprotein Ia/IIa.

CD71: An antigen ubiquitously distributed on the cell surface of actively growing human cells. It is a glycoprotein composed of disulfide-linked polypeptide chains, each of about 90 kD molecular weight. CD71 is also known as the transferrin receptor.

CD81: A 26-kD integral membrane protein, also known as TAPA1, which is expressed on many human cell types (including lymphocytes). CD81 is believed to associate with CD19 and CD21 to form B cell coreceptor. CD81 is a member of the transmembrane pore integral membrane protein family.

CD90: An 18-kD glycoprotein antigen expressed, for example, on $CD34^+$ human prothymocytes, fibroblasts and brain cells and on mouse T cells. CD90 is also known as Thy-1. It belongs to immunoglobulin supergene family, and consists of a single immunoglobulin homology unit that is either intermediate between V and C or somewhat more similar to a V homology unit.

CD122: The 75-kD 6-chain of the interleukin-2 receptor (also known as, IL-2Rβ). This antigen is expressed, for example, in natural killer cells, resting T cells and, some B cell lines.

CD164: A protein antigen of about 80 to 90 kD, which is expressed, for example, in human CD34+ hematopoietic progenitor cells (Zannettino et al., Blood, 92:2613-2628, 1998). CD164 belongs to a heterogeneous group of secreted or membrane-associated proteins called sialomucins. Sialomucins are believed to have two opposing functions in vivo: first, as cytoprotective or antiadhesive agents and, second, as adhesion receptors.

Differentiation: A process whereby relatively unspecialized cells (for example, undifferentiated cells, such as multilineage-inducible cells) acquire specialized structural and/or functional features characteristic of mature cells. Similarly, "differentiate" refers to this process. Typically, during differentiation, cellular structure alters and tissue-specific proteins appear. "Osteogenic differentiation" is a process whereby undifferentiated cells acquire one or more properties (for example, morphological, biochemical, or functional properties) characteristic of bone-related cells, such as osteoblasts or osteoclasts. "Chondrogenic differentiation" is a process whereby undifferentiated cells acquire one or more properties (for example, morphological, biochemical, or functional properties) characteristic of cartilage-related cells, such as chondrocytes. "Adipogenic differentiation" is a process whereby undifferentiated cells acquire one or more properties (for example, morphological, biochemical, or functional properties) characteristics of adipocytes. "Neural differentiation" is a process whereby undifferentiated cells acquire one or more properties (for example, morphological, biochemical, or function properties) characteristic of neural cells, such as glial cells, oligodendrocytes, or neurons. "Neuronal differentiation" is a process whereby undifferentiated cells acquire one or more properties (for example, morphological, biochemical, or function properties) characteristic of neurons. "β-cell-like differentiation" is a process whereby undifferentiated cells acquire one or more properties (for example, morphological, biochemical, or functional properties) characteristic of a pancreatic β-cell.

Expand: A process by which the number or amount of cells in a cell culture is increased due to cell division. Similarly, the terms "expansion" or "expanded" refers to this process. The terms "proliferate," "proliferation" or "proliferated" may be used interchangeably with the words "expand," "expansion", or "expanded." Typically, during an expansion phase, the cells do not differentiate to form mature cells.

Expression: The process by which the coded information of a gene is converted into an operational, non-operational, or structural part of a cell, often including the synthesis of a protein.

Thus, the term "expression" contemplates either or both gene expression, measured for example, by levels of RNA (such as, mRNA) in a cell, or protein expression. Methods of determining RNA levels are well known in the art, and include Northern blots, RT-PCR, RNAse protection, and others.

Methods of determining protein expression are similarly well known, and include Western blots, functional assays, immunofluorescence, optical absorbance, microscopy (including electron microscopy) and others.

Extracellular matrix (ECM): A complex network of different combinations of collagens, proteoglycans (PG), hyaluronic acid, laminin, fibronectin, and many other glycoproteins. The ECM is a scaffold that fills extracellular spaces. In some instances, the ECM (or particular components thereof) can mediating cell-to-cell interactions, or play a functional role in mediating cellular proliferation or differentiation.

Proteoglycans may be modified by glycosaminoglycans (GAGs), which are long-chain compounds of repeated disaccharide units. The four main types of GAGs consist mainly of sulfated heparan sulfate/heparin, chondroitin sulfate/dermatan, keratan sulfate, and the non-sulfated glycosaminoglycan hyaluronic acid. Many proteoglycans contain a core protein which links them to the cellular membrane. Hyaluronic acid is the only extracellular oligosaccharide that is not known to be covalently linked to a protein.

Growth factor: A substance that promotes cell growth, survival, and/or differentiation. Growth factors include molecules that function as growth stimulators (mitogens), molecules that function as growth inhibitors (e.g. negative growth factors) factors that stimulate cell migration, factors that function as chemotactic agents or inhibit cell migration or invasion of tumor cells, factors that modulate differentiated functions of cells, factors involved in apoptosis, or factors that promote survival of cells without influencing growth and differentiation Examples of growth factors are bFGF, EGF, CNTF, HGF, NGF, and activin-A.

Hepatocyte growth factor receptor (c-Met): A tyrosine kinase comprised of disulfide-linked subunits of about 50 kD (alpha) and about 145 kD (beta), which is a receptor for hepatocyte growth factor. In the fully processed c-Met product, the alpha subunit is extracellular, and the beta subunit has extracellular, transmembrane, and tyrosine kinase domains as well as sites of tyrosine phosphorylation. (See, for example, Bottaro et al., Science, 251:802-804, 1991).

Induce: To cause to move forward to a result. For example, certain cell culture conditions may establish an environment that prompts one or more events (sometime, a cascade of events), which results in the specialization of a previously unspecialized cell type. In this example, placing an unspecialized cell into such culture conditions induces the cell to become more specialized, such as to differentiate.

Isolated: An "isolated" cell is a cell that has been purified from the other cellular components of a tissue. Cells can be isolated by a variety of methods, including mechanical and/or enzymatic methods. In one embodiment, an isolated population of cells includes greater than about 50%, greater than about 75%, greater than about 90%, greater than about 95%, or greater than about 99% of the cells of interest. In another embodiment, an isolated population of cells is one in which no other cells of a different phenotype can be detected. In a further embodiment, an isolate population of cells is a population of cells that includes less than about 5%, or less than about 1% of cells of a different phenotype than the cells of interest. An "isolated" cell may be a population of clonally derived cells, such as cells expanded into a single-cell-derived colony.

Low density: A relatively small number of cells per unit area of a container in which the cells are contained. Adherent cells are often considered to be at low density when the population of cells do not form a continuous monolayer on the surface on which the cells are adhered. Exemplary low cell densities include no more than about $10^4$ cells/cm$^2$, or no more than about $10^5$ cells/cm$^2$.

Low-oxygen tension (or low oxygen conditions): Any culturing conditions below the normal atmospheric oxygen level (which is approximately 21%). Thus, in particular embodiments, low oxygen conditions are less than about 15% oxygen, less than about 10% oxygen, less than about 5% oxygen, or less than about 3% oxygen. In some embodiments, the culture oxygen conditions are kept as close as possible to the normal physiological oxygen conditions in which a particular cell would be found in vivo. This may mean that the oxygen conditions employed for a particular cell type will depend on the regional origin of that particular cell type. For example, cells from an alveolar origin may prefer growth at about 14% O2; cells from an arterial source will prefer an oxygen concentration of about 12%; whereas those from certain regions of the brain may prefer oxygen conditions as low as about 1.5%. Low oxygen conditions are not to be considered the same as "hypoxic" conditions. Low oxygen conditions are intended to mimic physiological conditions, whereas hypoxic conditions describe oxygen levels that are less than normal physiological conditions for a particular cell type.

Marker: A protein, glycoprotein, or other molecule expressed on the surface of a cell, which serves to help identify the cell. A cell surface marker can generally be detected by conventional methods. Specific, non-limiting examples of methods for detection of a cell surface marker are immunohistochemistry, fluorescence activated cell sorting (FACS), or an enzymatic analysis.

Multilineage-inducible cell: A cell capable of differentiating into more than one cell lineage. A multilineage cell is capable of differentiating into cell types derived from more tam one germ layer, including cell types of mesodermal, ectodermal or endodermal origin. In particular examples, a multilineage-inducible cell can be differentiated into mesodermal, neuroectodermal, and endodermal cell lineages, including, for instance, osteoblasts, chondrocytes, adipocytes, neurons, and β-like cells.

Neurological disorder: A disorder in the nervous system, including the central nervous system or the peripheral nervous system. The term "neurological disorder" includes neurogenerative disorders. A "neurogenerative disorder" is an abnormality in the nervous system of a subject, such as a mammal, in which neural integrity is threatened. Without being bound by theory, neural integrity can be threatened when neural cells display decreased survival or when the neurons can no longer propagate a signal. Specific, non-limiting examples of a neurological disorders are provided in the specification.

Neurotrophin-3 receptor (NTRK3) (also known as gp145 and trkC): A member of the TRK family of tyrosine protein kinase genes, which is expressed, for example, regions of the brain, including the hippocampus, cerebral cortex, and the granular cell layer of the cerebellum NTRK3 is a glycoprotein of about 145 kD, and a receptor for neurotrophin-3 (see, for example, Lamballe et al., *Cell*, 66:967-979, 1991; Valent et al., *Europ. J. Hum. Genet.*, 5:102-104, 1997; McGregor et al., *Genomics*, 22:267-272, 1994).

Oct-4: A known developmentally regulated, mammalian transcription factor containing the POU homeo domain, which is characteristically expressed in undifferentiated pluripotent embryonic stem cells (see, for example, Flasza et al., *Cloning Stem Cells*, 5(4):339-354, 2003; Bhattacharya et al., *Blood*, Dec. 30, 2003, published online at www.bloodjournal.org; Sui et al., *Differentiation*, 71(9-10): 578-585, 2003; Palmieri et al., *Dev. Biol.*, 166(1):259-267, 1994).

Pharmaceutically acceptable carriers: The pharmaceutically acceptable carriers useful in this invention are conventional. *Remington's Pharmaceutical Sciences*, by E. W. Martin, Mack Publishing Co., Easton, Pa., 15th Edition (1975), describes compositions and formulations suitable for pharmaceutical delivery of the multilineage-inducible cells herein disclosed.

In general, the nature of the carrier will depend on the particular mode of administration being employed. For instance, parenteral formulations usually comprise injectable fluids that include pharmaceutically and physiologically acceptable fluids such as water, physiological saline, balanced salt solutions, aqueous dextrose, glycerol or the like as a vehicle. For solid compositions (for example, powder, pill, tablet, or capsule forms), conventional non-toxic solid carriers can include, for example, pharmaceutical grades of mannitol, lactose, starch, or magnesium stearate. In addition to biologically neutral carriers, pharmaceutical compositions to be administered can contain minor amounts of non-toxic auxiliary substances, such as wetting or emulsifying agents, preservatives, and pH buffering agents and the like, for example sodium acetate or sorbitan monolaurate.

Post-natal: After birth. For example, a neonate (a newborn), a child, an adolescent, or an adult (including, for example, an aged adult).

Rex-1 (also known as Zfp-42): A known mammalian transcription factor containing zinc finger motifs, which is characteristically expressed in undifferentiated pluripotent embryonic stem cells (see, for example, Hosler et al., *Mol. Cell. Biol.*, 9(12):5623-5629, 1989; Rogers et al., *Development*, 113(3):815-824, 1991; Hosler et al., *Mol. Cell. Biol.*, 13(5):2919-2928, 1993; Nishiguchi et al., *J. Biochem. (Tokyo)*, 116(1):128-139, 1994).

Stage-specific embryonic antigen 4 (SSEA4): A globoseries glycolipid (related to SSEA1 and SSEA3) recognized by monoclonal antibodies originally raised to distinguish early stages of mouse development Primate pluripotent cells express SSEA-4 and SSEA-3, while SSEA-1 is expressed only upon differentiation of such cells. (See, for example, Andrews et al., *Int. J. Cancer*, 66:806-816, 1996; Thomson and Marshall, *Curr. Topics Dev. Biol.*, 38:133-165, 1998; Thomson et al., *Science*, 282:1145-1147, 1998).

Subject: Any living or postmortem mammal, such as humans, non-human primates, pigs, sheep, cows, rodents and the like which is to be the recipient of the particular treatment. In one embodiment, a subject is a human subject or a murine subject. Death of a subject is determined by any standard known in the art, including, for example, cessation of heart or brain function. A postmortem subject typically will have been dead for less than 48 hours, such as less than 24 hours. A postmortem subject may be housed in an environment that may slow cellular degradation, which occurs following death; for example, a cool environment (such as between about 0° C. and about 15° C., or between about 0° C. and about 10° C. between about 0° C. and about 4° C.) may slow cellular degradation.

Therapeutically effective amount of a cell: An amount of a MIAMI cell (or a differentiated MIAMI cell) that can be determined by various methods, including generating an empirical dose-response curve, potency and efficacy modeling, and other methods used in the biological sciences. In general, a therapeutically effective amount of MIAMI cells (or differentiated MIAMI cells) is an amount sufficient to alleviate at least one symptom of a disease or disorder to be treated in a subject. In one embodiment, a therapeutically effective amount of MIAMI cells (or differentiated MIAMI cells) is more than about 10,000 cells, more than about 20,000 cells, more than about 30,000 cells, or between about 5,000 cells and about 50,000 cells.

The therapeutically effective amount of cells will be dependent on the subject being treated (for example, the species or size of the subject), the degree that the subject is compromised, and the method and/or location of administration of the cells. In one embodiment, a therapeutically effective amount of cells is an amount of cells sufficient to measure MIAMI cells in the peripheral blood of a recipient.

Transduced and Transformed: A virus or vector "transduces" a cell when it transfers nucleic acid into the cell. A cell is "transformed" by a nucleic acid transduced into the cell when the DNA becomes stably replicated by the cell, either by incorporation of the nucleic acid into the cellular genome, or by episomal replication. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

Transplantation: The transfer of a tissue or an organ, or cells, from one body or part of the body to another body or part of the body. An "allogeneic transplantation" or a "heterologous transplantation" is transplantation from one individual to another, wherein the individuals have genes at one or more loci that are not identical in sequence in the two individuals. An allogeneic transplantation can occur between two individuals of the same species, who differ genetically, or between individuals of two different species. An "autologous transplantation" is a transplantation of a tissue or cells from one location to another in the same individual, or transplantation of a tissue or cells from one individual to another, wherein the two individuals are genetically identical.

Treating a disease: Refers to inhibiting (or preventing) the partial or full development or progression of a disease, for example in a person who is known to have a predisposition to a disease. An example of a person with a known predisposition is someone with a history of diabetes in the family, or who has been exposed to factors that predispose the subject to a condition, such as lupus or rheumatoid arthritis. Moreover, treating a disease refers to a therapeutic intervention that ameliorates at least one sign or symptom of a disease or pathological condition, or interferes with a pathophysiological process, after the disease or pathological condition has begun to develop.

Unless otherwise explained, all technical and scientific terms used herein have the same meaning as commonly understood by one of ordinary skill in the art to which this invention belongs. The singular terms "a," "an," and "the" include plural referents unless context clearly indicates otherwise. Similarly, the word "or" is intended to include "and" unless the context clearly indicates otherwise. "Comprising" means "including." Hence "comprising A or B" means including A or B, or including A and B. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including explanations of terms, will control. In addition, the materials, methods, and examples are illustrative only and not intended to be limiting.

Except as otherwise noted, the methods and techniques of the present invention are generally performed according to conventional methods well known in the art and as described in various general and more specific references that are cited and discussed throughout the present specification. See, e.g., Sambrook et al., *Molecular Cloning: A Laboratory Manual*, 2d ed., Cold Spring Harbor Laboratory Press, 1989; Sambrook et al., *Molecular Cloning: A Laboratory Manual*, 3d ed., Cold Spring Harbor Press, 2001; Ausubel et al., *Current Protocols in Molecular Biology*, Greene Publishing Associates, 1992 (and Supplements to 2000); Ausubel et al., *Short Protocols in Molecular Biology: A Compendium of Methods from Current Protocols in Molecular Biology*, 4th ed., Wiley & Sons, 1999; Harlow and Lane, *Antibodies: A Laboratory Manual*, Cold Spring Harbor Laboratory Press, 1990; and Harlow and Lane, *Using Antibodies: A Laboratory Manual*, Cold Spring Harbor Laboratory Press, 1999; each of which is specifically incorporated herein by reference in its entirety.

IV. MIAMI Cells

Disclosed herein are isolated post-natal, multilineage-inducible cells (MIAMI cells), which express a unique set of molecular markers. A summary of selected markers expressed (or not expressed, as applicable) in various MIAMI cell embodiments is shown in Table 1.

TABLE 1

Representative MIAMI Cell Markers

| Marker | MIAMI Cell Expression |
|---|---|
| CD10 | + |
| CD13 | − |
| CD29 | + |
| CD34 | − |
| CD36 | − |
| CD44 | + |
| CD45 | − |
| CD49b | − |
| CD49e | + |
| CD54 (ICAM-1) | − |
| CD56 (NCAM) | − |
| CD63 | + |
| CD71 | − |
| CD81 (TAPA-1) | + |
| CD90 | + |
| CD103 | + |
| CD109 | − |
| CD117 (cKit) | − |
| CD122 (IL-2Rβ) | + |
| CD133 | − |
| CD156 | + |
| CD164 | + |
| BMP-receptor 1B | + |
| CNTFR | + |
| HGF Receptor (c-Met) | + |
| Class I-HLA | − |
| HLA-DR | − |
| hTERT | + |
| NTRK3 | + |
| POU4F1 (Oct-4) | + |
| Rex-1 | + |
| SSEA4 | + |

MIAMI cells may be identified by any unique set of the markers set forth in Table 1. For example, MIAMI cells may uniquely express at least one, at least two, at least three, at least four, at least five, or at least six of the Table 1 markers. In some embodiments, MIAMI cells express at least one of CD29, CD81, CD90, or stage-specific embryonic antigen 4 (SSEA4), and at least one of CD122, CD164, hepatocyte growth factor receptor (c-Met), bone morphogenetic protein receptor, type IB (BMP-receptor 1B), neurotrophic tyrosine kinase receptor type 3 (NTRK3), Oct-4, or Rex-1. In other examples, MIAMI cells express at least one of c-Met, BMP-receptor 1B, or NRTK3. In still other examples, MIAMI cells express at least a combination of CD29, CD81, CD90, CD122, and CD164.

Figure 1:
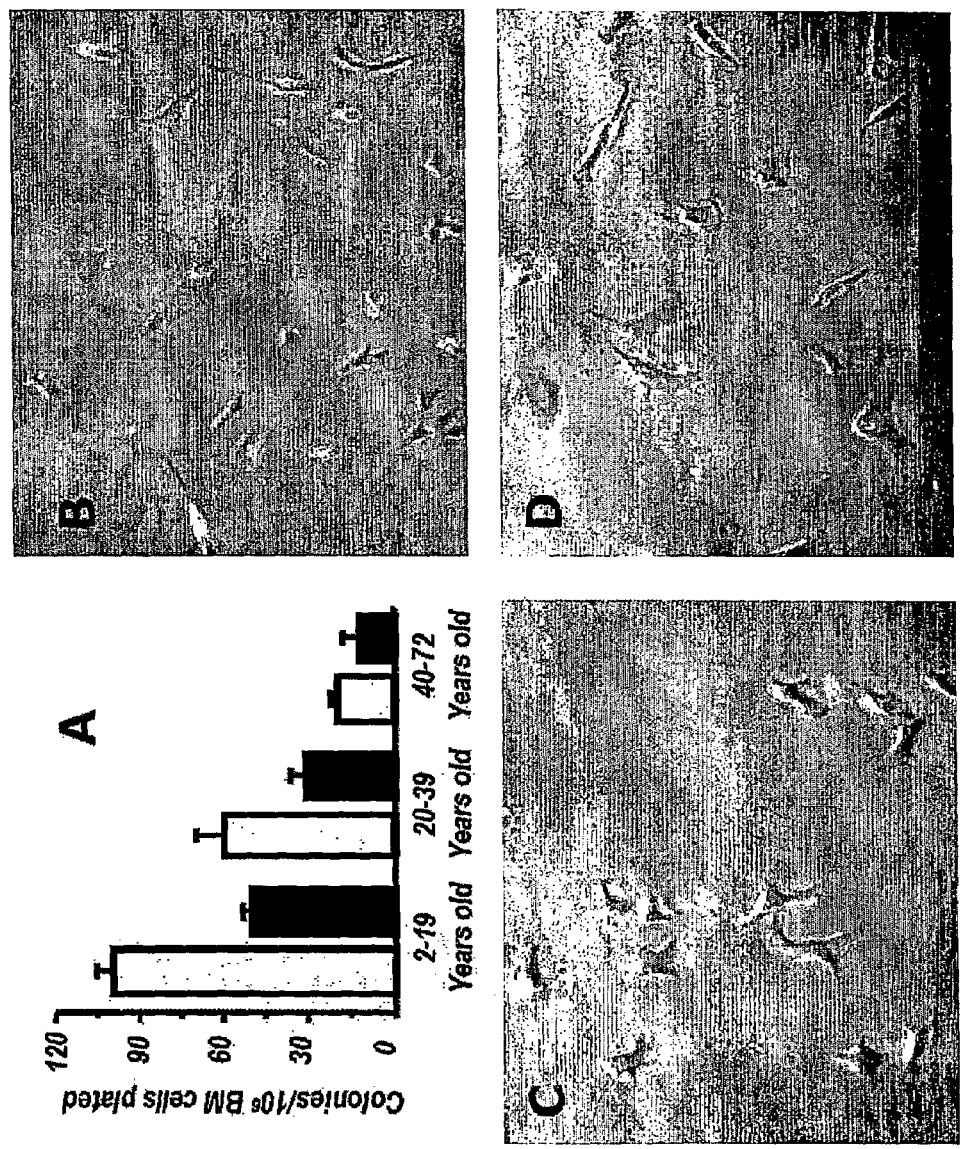
FIG. 1A shows a histogram of the number of colonies obtained with and without density gradient centrifugation of bone marrow cells harvested from donors of the indicated ages. The number of colonies arising after density gradient centrifugation (black bars) was significantly smaller compared to the number of colonies obtained without centrifugation (white bars) after plating the same number of bone marrow cells per dish using the conditions for expansion/selection of MIAMI cells. This result was observed in all cultures examined independent of age. The graph shows the mean±sem of more than 15 representative experiments.
FIG. 1B-C each show digital photographs of MIAMI cells taken at 20× magnification. MIAMI cells are small (7-10-micron), highly proliferative cells exhibiting reduced cytoplasm (e.g., FIG. 1B). The morphology of the cells is maintained after 5° cell doublings (FIG. 1C) and 52 cell doublings (FIG. 1D).

MIAMI cells are generally small cells. In some examples, a MIMI cell is between about 5 μm and about 12 μm, such as between about 7 μm and about 10 μm MIAMI cells typically contain relatively little cytoplasm (see, for example, FIG. 1) and are highly proliferative. In some examples, MIAMI cells have a population doubling time of about 20 hours to about 36 hours.

MIAMI cells can be isolated from a living or postmortem mammal of any age. A mammal includes either human or non-human mammals. In some examples, MIAMI cells are isolated from post-natal subjects, such as a neonate, a child, an adolescent or an adult (including, without limitation, an aged adult) of any mammalian species. In particular embodiments, MIAMI cells are isolated from an adult primate, such as a human.

A subject from whom a biological sample is collected may be a postmortem subject. In particular examples, a postmortem subject is recently deceased. Death of a subject may be determined by any standard known in the art, such as cessation of heart function, or cessation of brain function. In some embodiments, a postmortem subject is one whose heart has recently (such as within about 1 to about 4 hours) stopped beating, or a subject who has no measurable brain activity, or a subject intended for organ or tissue donation. In other examples, a postmortem subject may have been dead for up to 48 hours, such as up to 24 hours or up to 12 hours. In particular examples, a postmortem subject may be housed in a cold environment, such as between about 0° to about 15° C., between about 1° C. to about 10° C., or between about 1° C. to about 5° C., prior to collection of a biological sample.

MIAMI cells may be isolated from one or more biological sample(s), such as bone marrow, vertebral bodies, peripheral blood, umbilical cord blood, iliac crest aspirate, fat, cartilage, muscle, skin, bone, teeth, liver or brain Methods for collection of a biological sample will vary depending upon, for example, the type of sample to be collected. Such collection methods are well known in the art. For instance, bone marrow may be collected by inserting a needle into the marrow cavity of a bone under local anesthetic and aspirating marrow from the bone. It may be useful (though not required) to maintain sterile conditions during collection of a sample to reduce the possibility of bacterial, fungal or other infection in a subsequent cell culture of MIAMI cells (see below).

MIAMI cells may be isolated from a biological sample by any method known in the art or a combination thereof, including without limitation the methods disclosed herein (see, for example, Example 1). In one embodiment, MIAMI cells are selectively expanded using cell culture techniques. In other embodiments, MIAMI cells are isolated from a biological sample based on the physical properties of the MIAMI cells. For example, several techniques are known in the art by which MIAMI cells may be isolated based on the unique set of markers expressed by MIAMI cells, including, for example, fluorescence-activated cell sorting (FACS), immobilized marker-specific antibodies (such as, antibody-coupled beads), or magnetic-activated cell sorting (MACS).

MIAMI cells may also be isolated on the basis of other physical properties of the MIAMI cells, such as cell size. A biological sample can be sorted on the basis of cell size using any method known in the art. For example, cells in a biological sample may be passed through one or more filters of varying pore size, including filters having a larger pore size, such as of about 50-200 µm, or about 80-100 µm, or filters having a smaller pore size, such as of about 10-50 µm or 20-40 µm. In some examples, sequential filters having decreasing pore size may be employed. In one embodiment, the cells passed through one or more filters are less than 40 µm in diameter. In other embodiments, isolated cells are between about 5 µm and 12 µm in diameter. The cellular component of a biological sample can also be sorted by size by passing a cell population through one or more size-exclusion column(s). In one such embodiment, the cells are eluted along a size gradient such that the largest cells are eluted first and the smallest cells are eluted last. The cells can also be sorted by size using FACS. MIAMI cells may comprise more than about 10%, about 25%, about 50%, about 90% of size-sorted cell sample.

V. Methods of Isolating and Expanding MIAMI Cells

Methods for isolation and expansion of MIAMI cells have been identified and are disclosed herein. A method of isolation of the MIMI cells includes obtaining a cell population from one or more biological sample(s), such as bone marrow, vertebral bodies, peripheral blood, umbilical cord blood, iliac crest aspirate, fat, cartilage, muscle, skin, bone, teeth, liver or brain Methods for collecting a biological sample useful in the disclosed methods are the same as discussed above.

A biological sample, optionally, may be partially purified after collection. For example, non-cellular materials or dead or damaged cells may be removed by any technique known in the art.

Though not bound by theory, it is believed that MIAMI cells respond favorably to signals (whether humoral, physical, or other signals) produced by one or more other cell types that reside with MIAMI cells within a biological compartment (from which a biological sample is taken); thus, isolation of MIAMI cells may be enhanced by maintaining MIAMI cells and such other resident cell type(s) in proximity to one another and/or in functional contact. In some embodiments, unfractionated cellular components of a biological sample will be retained for subsequent isolation of MIAMI cells. In other embodiments, a biological sample may be fractionated so as to co-fractionate MIAMI cells and any other cell types functionally relevant to MIAMI cells viability. In yet another embodiment, a biological sample may be fractionated to selectively remove cells (or other components) that do not reside with MIAMI cells, but which may be inadvertently included in a sample as a result of a particular cell collection process, such as connective tissue, or mature red blood cells.

In one specific, non-limiting example, the resulting population of cells includes MIAMI cells as greater than 50% of the population, greater than 80% of the population, greater than 90% of the population, or greater than 95% of the population.

1. Cell Culture Methods

Once a biological sample is collected and, as applicable, prepared, the cell population from the sample is further selected and expanded in culture medium. A cell population comprising at least one MIAMI cell is contemplated. In some examples, between about $10^4$ cells/cm$^2$ and about $10^6$ cells/cm$^2$ are used to seed the culture. In a particular example, about $10^5$ cells/cm$^2$ are used to seed the culture.

The mean PO$_2$ in various tissues has been estimated from 5 to 71 Torr (that is, about 0.7% to about 9% oxygen at sea level) (Kaufman and Mitchell, *Comp. Biochem. Physiol A*, 107: 673-678, 1994; Volhmar et al., *Anesth. Analg.*, 75:421-430, 1992; Buerk and Nair, *J. Appl. Physiol.*, 74:1723-1728, 1993; Levy et al., *Pflugers Archiv.*, 407: 388-95, 1986; Jiang et al., *J. App. Physiol.* 80: 552-558, 1996). In comparison, pO$_2$ of tissue culture performed in room air is about 149 Torr or about 21% oxygen (at sea level). A cell population containing MIAMI cells is cultured under low oxygen conditions. In some embodiments, low oxygen conditions comprise about 0.5% to about 10% oxygen, such as about 1% to about 5% oxygen, or about 1% to about 3% oxygen. In a particular example, low oxygen conditions comprise about 3% oxygen.

In some methods, a subpopulation of cells from the sample adheres to a solid substrate (referred to as "adherent cells"), such as a cell culture container (for example, a culture dish, a culture flask, or beads designed for tissue culture). In some embodiments the solid substrate comprises an extracellular matrix (ECM) substrate. ECM substrates include, for example, fibronectin, collagen, laminin, vitronectin, polylysine, tenascin, elastin, proteoglycans (such as, heparan sulfate proteoglycans), entactin, Matrigel™, synthetic RGDS-containing peptides covalently crosslinked to hydrophobic biocompatible scaffolds (such as polyethylene glycol (PEG), poly glycolic acid (PGA), poly(D,L-lactide-co-glycolide) (PLGA), or others), or a combination thereof. Any or all forms of a particular ECM substrate are contemplated herein. For example, collagen is commonly known to occur in multiple isoforms (*Molecular Biology of the Cell*, 3rd Edition, ed. by Alberts et al., New York: Garland Publishing, 1994, Ch. 19), including eighteen different collagen isoforms (such as collagen I, II, III, IV, V, and others). Similarly, multiple isoforms of laminin (Ekblom et al., *Ann. N.Y. Acad. Sci.*, 857: 194-211, 1998) and fibronectin ((*Molecular Biology of the Cell*, 3rd Edition, ed. by Alberts et al., New York: Garland Publishing, 1994, Ch 19) are known. In specific, non-limiting embodiments, an ECM substrate comprises a 1-1000 ng/ml fibronectin-coated solid substrate, for example a 10 ng/ml fibronectin-coated solid substrate.

In other methods, adherent cells are co-cultured with cells from the biological sample, which do not adhere to a solid substrate and remain in suspension (referred to as "non-adherent cells"). Adherent and non-adherent cells may be co-cultured for various durations, such as for no less than about 3 days, no less than about 5 days, no less than about 7 days, or no less than about 14 days. In a particular example, adherent and non-adherent cells are co-cultured for about 14 days. After which time, non-adherent cells may be removed from the culture.

The culture medium can be any medium or any buffer that maintains the viability of the cells, such as a growth medium. Numerous culture media are known and are suitable for use. Generally, a growth medium includes a minimal essential medium. In one embodiment, the medium is DMEM-low glucose (DMEM-LG).

The growth medium may be supplemented with serum. Specific, non-limiting examples of serum are horse, calf or fetal bovine serum (FBS). The medium can have between about 2% by volume to about 10% by volume serum, or about 5% by volume serum, or about 2%. In one embodiment, a growth medium is supplemented with about 5% FBS.

In one embodiment, the medium contains one or more additional additives, such as antibiotics or nutrients. Specific non-limiting examples of antibiotics include 10-1000 U/ml penicillin and about 0.01 mg/ml to about 10 mg/ml streptomycin. In a particular example, a growth medium contains about 100 U/ml penicillin and about 1 mg/ml streptomycin.

In one embodiment, the cells are cultured in the growth medium for about 7 days to about 20 days. In another embodiment, the cells are cultured in the growth medium for about 12 days to about 16 days. In a particular embodiment, the cells are cultured in the growth medium for about 14 days. Thereafter, single-ell-derived colonies of MIAMI cells may be isolated for expansion using any technique known in the art, such as cloning rings. Alternatively, single-cell-derived colonies of MIAMI cells may be pooled for expansion.

MIAMI cells are expanded under low oxygen conditions and in a growth medium as described above. In a particular example, MIAMI cells are expanded in growth medium supplemented with about 2% FBS. In another example, MIAMI cells are expanded in growth medium supplemented with about 100 U/ml penicillin and about 1 mg/ml streptomycin. In some embodiments, MIAMI cells are expanded on a solid substrate comprising an ECM substrate, such as (1-1000 ng/ml) fibronectin-coated substrates, for example a 10 ng/ml fibronectin-coated substrate.

2. Other Methods of MIAMI Cell Separation

As unique sets of MIAMI cell markers have been disclosed herein, fluorescence activated cell sorting (FACS) may be one exemplary technique useful for isolating MIAMI cells. FACS can be used to sort cells that express a particular cell surface marker or set of cell surface markers by contacting the cells with one or more appropriately labeled antibody(ies). FACS employs a plurality of color channels, low angle and obtuse light-scattering detection channels, and impedance channels, among other more sophisticated levels of detection, to separate or sort cells. Any FACS technique may be employed as long as it is not detrimental to the viability of the desired cells. (For exemplary methods of FACS, see U.S. Pat. No. 5,061, 620). In one embodiment, multiple antibodies and FACS sorting can be used to produce isolated populations of $CD29^+$, $CD81^+$, $CD90^+$, $CD122^+$, $CD164^+$, multilineage-inducible cells, or to purify cells that express CD29, CD81, CD90, CD122, and CD164, but do not express at least one of CD13, CD49b, or CD71. In other embodiments, FACS sorting can be used to produce isolated populations of multilineage-inducible cells that express at least one of CD29, CD81, CD90, or stage-specific embryonic antigen 4 (SSEA4), and at least one of CD122, CD164, hepatocyte growth factor receptor (c-Met), bone morphogenetic protein receptor, type IB (BMP-receptor 1B), neurotrophic tyrosine kinase receptor type 3 (NTRK3), Oct-4, or Rex-1. In still other embodiments, post-natal, multilineage-inducible cells that express at least one of c-Met, BMP-receptor 1B, or NTRK3 may be isolated by FACS.

Other techniques of differing efficacy may be employed to purify and isolate desired populations of cells. The separation techniques employed should maximize the retention of viability of the fraction of the cells to be collected. The particular technique employed will, of course, depend upon the efficiency of separation, cytotoxicity of the method, the ease and speed of separation, and what equipment and/or technical skill is required.

Separation procedures may include magnetic separation, using antibody-coated magnetic beads, affinity chromatography, cytotoxic agents, either joined to a monoclonal antibody or used in conjunction with complement, and "panning," which utilizes a monoclonal antibody attached to a solid matrix, or another convenient technique. Antibodies attached to magnetic beads and other solid matrices, such as agarose beads, polystyrene beads, hollow fiber membranes and plastic petri dishes, allow for direct separation. Cells that are bound by the antibody can be removed from the cell suspension by simply physically separating the solid support from the cell suspension. The exact conditions and duration of incubation of the cells with the solid phase-linked antibodies will depend upon several factors specific to the system employed. The selection of appropriate conditions, however, is well within the skill in the art.

The unbound cells then can be eluted or washed away with physiologic buffer after sufficient time has been allowed for the cells expressing a marker of interest (for example, CD29, CD81, CD90, CD122, or CD164) to bind to the solid-phase linked antibodies. The bound cells are then separated from the solid phase by any appropriate method, depending mainly upon the nature of the solid phase and the antibody employed.

Antibodies may be conjugated to biotin, which then can be removed with avidin or streptavidin bound to a support or fluorochromes, which can be used with a fluorescence activated cell sorter (FACS), to enable cell separation (see above).

In one embodiment, MIAMI cells may be separated from other cells by the cell-surface expression of CD29, CD81, CD90, CD122, and CD164. In one specific, non-limiting example, CD29+ cells are positively selected by magnetic bead separation, wherein magnetic beads are coated with CD29-reactive antibody. The CD29+ cells are then removed from the magnetic beads, for example, by culture release or other methods known in the art. The CD29+ cells may be further purified, for example, in serial steps using magnetic beads coated with CD81−, then CD90−, then CD122, and finally CD164-reactive antibody (as described for α-CD29-coated beads). Alternatively, at any stage, different purification methods may be performed, such as FACS sorting the population of cells released from the magnetic beads.

In one embodiment, magnetic bead separation is used to first separate a population of cells that do not express at least one of CD36, CD49b, CD71, or CD133. In this embodiment, the unbound cells will be enriched for MIAMI cells. MIAMI cells may be separated from the enriched cell population as previously described. In addition, panning can be used to separate cells that do not express one or more specific markers, such as CD36, CD49b, CD71, or CD133 (for panning methods see Small et al., *J. Immunol. Meth.*, 167(1-2):103-107, 1994).

MIAMI cells isolated by these or other methods can be maintained in culture, such as described herein.

VI. Methods of Inducing MIAMI Cell Differentiation

MIAMI cells may be differentiated into mesodermal, ectodermal, and endodermal cell lineages. In particular examples, MIAMI cells may be differentiate into osteoblasts, chondrocytes, adipocytes, neurons, and pancreatic-islet-like cells.

1. Osteogenic Differentiation

A method is disclosed herein for differentiating a MIMI cell into an osteogenic cell, such as an osteoblast. In one embodiment, osteogenic differentiation is induced by culturing MIAMI cells in an osteogenic medium. The osteogenic medium can be any medium or any buffer that maintains the viability of the cells and induces osteogenic differentiation in the cells. Numerous culture media are known and are suitable for use (see, for example, Kitamura et al., *Artif. Organs*, 28(1):72-82, 2004; Temenoff et al., *Biomacromolecules*, 5(1):5-10, 2004; Ogawa et al., *Biochem. Biophys. Res. Commun.*, 313(4):871-877, 2004; Ikeuchi et al., *J. Biomed. Mater. Res.*, 67A(4):1115-1122, 2003; Li et al., *Bone*, 33(4):652-659, 2003; Gerstenfeld et al., *Connect. Tissue Res.*, 44(Suppl 1):85-91, 2003; Sottile et al., *Cloning Stem Cells*, 5(2): 149-155, 2003; Yeh et al., *J. Cell. Biochem.*, 87(3):292-304, 2002; Jaiswal et al.; *J. Biol. Chem.*, 275(13):9645-9652, 2000).

Generally, an osteogenic medium includes a minimal essential medium. In one embodiment, the medium is A-MEM (GIBCO-BRL). An osteogenic medium typically contains one or more additional additives, such as one or more antibiotics, growth factors, nutrients, or combinations thereof. Specific, non-limiting examples of such additives are shown in Table 2 below:

TABLE 2

Osteogenic Media Supplements

| Additive | Exemplary Concentration |
|---|---|
| serum | About 2% to about 10% |
| penicillin | About 1 U/ml to about 1000 U/ml |
| streptomycin | About 0.01 mg/ml to about 10 mg/ml |
| ascorbic acid 2-phosphate | About 10 µM to about 1 mM |
| β-glycerolphosphate | About 10 µM to about 1 mM |

TABLE 2-continued

Osteogenic Media Supplements

| Additive | Exemplary Concentration |
|---|---|
| dexamethasone | About 1 nM to about 100 nM |
| DMSO | About 0.0001% to about 0.01% |

In one embodiment, the osteogenic medium includes at least ascorbic acid 2-phosphate and β-glycerolphosphate. In one specific example, the osteogenic medium includes between about 50 µM to about 200 µM ascorbic acid 2-phosphate, such as for example between about 75 µM to about 125 µM, or between about 90 µM to about 110 µM ascorbic acid 2-phosphate. In yet another example, the osteogenic medium includes about 100 µM ascorbic acid 2-phosphate. In another embodiment, the osteogenic medium includes between about 1 mM to about 20 mM β-glycerolphosphate, such as for example between about 5 mM to about 15 mM, or between about 8 mM to about 12 mM β-glycerolphosphate. In a particular embodiment the osteogenic medium includes about 10 mM β-glycerolphosphate.

In another embodiment, an osteogenic medium includes dexamethasone, such as between about 1 nM to about 20 nM dexamethasone, between about 5 nM to about 15 nM, or between about 8 nM to about 12 nM dexamethasone. In yet another example, the osteogenic medium includes about 10 nM dexamethasone. In one method, dexamethasone is added to an osteogenic medium after MIAMI cells are first introduced to an osteogenic medium. In some embodiments, dexamethasone is added between about 6 hours and about 72 hours later, such as between about 12 hours and about 36 hours later, or between about 18 hours and about 28 hours later. In one embodiment, dexamethasone is added to an osteogenic medium after about 24 hours.

In one, non-limiting example, MIAMI cells are contacted with an osteogenic medium comprising α-MEM supplemented with 10% FBS, 100 µM ascorbic acid 2-phosphate and 10 mM β-glycerolphosphate; then, about 24 hours later, 10 nM dexamethasone is added to the osteogenic medium. In a more specific example, the α-MEM is further supplemented with 100 U/ml penicillin and 1 mg/ml streptomycin.

Osteogenic differentiation may be expected to occur, for example, in a 100% humidified atmosphere of 95% air, 5% CO2 at 37° C. Osteogenic differentiation may be detected between about 3 weeks to about 4 weeks.

Differentiation of MIAMI cells into osteogenic cells, such as osteoblasts, can be measured by any method known to one of skill in the art. Specific, non-limiting examples are immunohistochemical analysis to detect expression of bone-related polypeptides (for example, Runx2, osteocalcin, collagen (such as, collagen I α1), or bone sialoprotein), or assays such as ELISA assay and Western blot analysis. Differentiation of cells can also be measured by assaying the level of mRNA coding for bone-related polypeptides (for example, Runx2, osteocalcin, collagen (such as, collagen I α1), or bone sialoprotein) using techniques such as Northern blot, RNase protection and RT-PCR. In another embodiment, functional assays of bone-forming capacity can be measured, including alkaline phosphatase activity, in vitro mineralization, and in vitro production of extracellular matrix or bone nodules.

2. Chondrogenic Differentiation

A method is disclosed herein for differentiating a MIAMI cell into a chondrogenic cell, such as a cartilage cell. In one embodiment, chondrogenic differentiation is induced by culturing MIAMI cells in a chondrogenic medium. The chondrogenic medium can be any medium or any buffer that maintains the viability of the cells and induces chondrogenic differentiation in the cells. Numerous culture media are known and are suitable for use (see, for example, Ogawa et al., *Biochem. Biophys. Res. Commun.*, 313(4):871-877, 2004; Kavalkovich, *In Vitro Cell. Dev. Biol. Anim.*, 38(8):457-466, 2002; Barry et al., *Exp. Cell Res.*, 268(2):189-200, 2001; Kramer et al., *Mech. Dev.*, 92(2):193-205, 2000; Mackay et al., *Tissue Eng.*, 4(4):415-428, 1998).

Generally, a chondrogenic medium includes a serum-free, minimal essential medium. In one embodiment, the medium is DMEM-high glucose (DMEM-HG) (GIBCO-BR-L). A chondrogenic medium typically contains one or more additional additives, such as one or more antibiotics, growth factors, nutrients, or combinations thereof. Specific, non-limiting examples of such additives are shown in Table 3 below:

TABLE 3

Chondrogenic Media Supplements

| Additive | Exemplary Concentration |
|---|---|
| dexamethasone | About 10 nM to about 1000 nM |
| TGF-β3 | About 1 ng/ml to about 100 ng/ml |
| ascorbic acid 2-phosphate | About 5 μg/ml to about 500 μg/ml |
| sodium pyruvate | About 1 μg/ml to about 1000 μg/ml |
| proline | About 4 μg/ml to about 400 μg/ml |
| insulin | About 0.6 μg/ml to about 63 μg/ml |
| transferrin | About 0.6 μg/ml to about 63 μg/ml |
| selenous acid | About 0.6 μg/ml to about 63 μg/ml |
| linoleic acid | About 0.5 μg/ml to about 55 μg/ml |
| albumin | About 0.1 mg/ml to about 13 mg/ml |
| penicillin | About 1 U/ml to about 1000 U/ml |
| streptomycin | About 0.01 mg/ml to about 10 mg/ml |

In one embodiment, the chondrogenic medium includes at least TGF-β3. In one specific example, the chondrogenic medium includes between about 5 ng/ml to about 20 ng/ml TGF-β3, such as for example between about 7 ng/ml to about 15 ng/ml, or between about 8 ng/ml to about 12 ng/ml TGF-3. In yet another example, the chondrogenic medium includes about 10 ng/ml TGF-β3. In another embodiment, the chondrogenic medium includes at least dexamethasone (for example, between about 50 nm to about 200 nM, or between about 75 nM to about 150 nM), TGF-β3, (for example, between about 5 ng/ml to about 20 ng/ml, or between about 7.5 ng/ml to about 15 ng/ml) ascorbic acid 2-phosphate (for example, between about 25 μg/ml to about 100 μg/ml, or between about 40 μg/ml to about 60 μg/ml), sodium pyruvate (for example, between about 50 μg/ml to about 200 μg/ml, or between about 75 μg/ml to about 150 μg/1 ml), proline (for example, between about 20 μg/ml to about 80 μg/ml, or between about 30 μg/ml to about 50 μg/1 ml), insulin (for example, between about 1 μg/ml to about 15 μg/ml, or between about 3 μg/ml to about 10 μg/ml), transferrin (for example, between about 1 μg/ml to about 15 μg/ml, or between about 3 μg/ml to about 10 μg/ml), and selenous acid (for example, between about 1 μg/ml to about 15 μg/ml, or between about 3 μg/ml to about 10 μg/ml).

In one, non-limiting example, a chondrogenic medium is serum-free, DMEM-HG, 100 nM dexamethasone, 10 ng/ml TGF-β3, 50 μg/ml ascorbic acid 2-phosphate, 100 μg/ml sodium pyruvate, 40 μg/ml proline, 6.25 μg/ml bovine insulin, 6.25 μg/ml transferrin, 6.25 μg/ml selenous acid, 5.33 μg/ml linoleic acid, and 1.25 mg/ml bovine serum albumin).

In one method, MIAMI cells are suspended in a chondrogenic medium and placed in a tube, such as a conical tube. In this example, MIAMI cells are allowed to settle to the bottom of the tube. Chondrogenic differentiation may be expected to occur, for example, in a 100% humidified atmosphere of 95% air, 5% CO2 at 37° C. Chondrogenic differentiation may be detected between about 2 weeks to about 8 weeks, for example between about 3 weeks to about 6 weeks. In a particular example, chondrogenic differentiation is detected within about 4 weeks of contacting MIAMI cells with a chondrogenic medium.

Differentiation of MIAMI cells into chondrogenic cells, such as cartilage cells, can be measured by any method known to one of skill in the art. Specific, non-limiting examples are immunohistochemical analysis to detect expression of cartilage-related polypeptides (for example, collagen II), or assays such as ELISA assay and Western blot analysis. Differentiation of cells can also be measured by assaying the level of mRNA coding for cartilage-related polypeptides (for example, collagen II or aggrecan) using techniques such as Northern blot, RNase protection and RT-PCR. In another embodiment, functional assays can be used to determine chondrogenic differentiation, including for example cartilaginous tissue-forming capacity or production of a proteoglycan-rich soft collagen matrix.

3. Adipogenic Differentiation

A method is disclosed herein for differentiating a MIAMI cell into an adipogenic cell, such as an adipocyte. In one embodiment, adipogenic differentiation is induced by culturing MIAMI cells in an adipogenic medium. The adipogenic medium can be any medium or any buffer that maintains the viability of the cells and induces adipogenic differentiation in the cells. Numerous culture media are known and are suitable for use (see, for example, Kitamura et al., *Artif. Organs*, 28(1):72-82, 2004; Temenoff et al., *Biomacromolecules*, 5(1):5-10, 2004; Ogawa et al., *Biochem. Biophys. Res. Commun.*, 313(4):871-877, 2004; Ikeuchi et al., *J. Biomed. Mater. Res.*, 67A(4): 1115-1122, 2003; Li et al., *Bone*, 33(4):652-659, 2003; Gerstenfeld et al., *Connect. Tissue Res.*, 44(Suppl 1):85-91, 2003; Sottile et al., *Cloning Stem Cells*, 5(2): 149-155, 2003; Yeh et al., *J. Cell. Biochem.*, 87(3):292-304, 2002; Jaiswal et al., *J. Biol. Chem.*, 275(13):9645-9652, 2000).

Generally, an adipogenic medium includes a minimal essential medium. In one embodiment, the medium is A-MEM (GIBCO-BRL). An adipogenic medium may be supplemented with serum, such as horse, calf, or fetal bovine serum or combinations thereof. An adipogenic medium can have between about 5% by volume to about 25% by volume serum, or about 20% by volume serum, or about 10%. In one embodiment, a growth medium is supplemented with 10% FBS and 10% horse serum.

An adipogenic medium typically contains one or more additional additives, such as one or more antibiotics, growth factors, nutrients, or combinations thereof. Specific, non-limiting examples of such additives are shown in Table 4 below:

TABLE 4

Adipogenic Media Supplements

| Additive | Exemplary Concentration |
|---|---|
| serum | About 5% to about 25% |
| penicillin | About 1 U/ml to about 1000 U/ml |
| streptomycin | About 0.01 mg/ml to about 10 mg/ml |
| hydrocortisone | About 0.05 μM to about 5 μM |
| isobutylmethylxanthine | About 0.05 mM to about 5 mM |
| indomethacine | About 6 μM to about 600 μM |

In one embodiment, the adipogenic medium includes at least hydrocortisone, isobutylmethylxanthine, and indomethacine. In one specific example, the adipogenic medium includes between about 0.2 μM to about 1.0 μM hydrocortisone, such as for example between about 0.3 μM to about 0.7 μM, or between about 0.4 μM to about 0.6 μM hydrocortisone. In yet another example, the adipogenic medium includes about 0.5 μM hydrocortisone. In another embodiment, the adipogenic medium includes between about 0.2 mM to about 1.0 mM isobutylmethylxanthine, such as for example between about 0.3 mM to about 0.7 mM, or between about 0.4 mM to about 0.6 mM isobutylmethylxanthine. In a particular embodiment, the adipogenic medium includes about 0.5 mM isobutylmethylxanthine. In another specific example, the adipogenic medium includes between about 30 μM to about 120 μM indomethacine, such as for example between about 40 μM to about 90 μM, or between about 50 μM to about 70 μM indomethacine. In yet another example, the adipogenic medium includes about 60 μM indomethacine.

In one, non-limiting example, MIAMI cells are contacted with an adipogenic medium comprising α-MEM, 10% FBS, 10% horse serum, 0.5 μM hydrocortisone, 0.5 mM isobutylmethylxanthine, and 60 μM indomethacine. In a more specific example, the α-MEM is further supplemented with 100 U/ml penicillin and 1 mg/ml streptomycin.

Adipogenic differentiation may be expected to occur, for example, in a humidified atmosphere (such as, 100% humidity) of 95% air, 5% CO2 at 37° C. Adipogenic differentiation may be detected between about 1.5 weeks to about 6 weeks. In particular examples, adipogenic differentiation may be detected in about 3 weeks.

Differentiation of MIAMI cells into adipogenic cells, such as adipocytes, can be measured by any method known to one of skill in the art. Specific, non-limiting examples are immunohistochemical analysis to detect expression of adipose-related polypeptides (for example, lipoprotein lipase or peroxisome proliferators-activated receptor γ-2), or assays such as ELISA assay and Western blot analysis. Differentiation of cells can also be measured by assaying the level of mRNA coding for bone-related polypeptides (for example, lipoprotein lipase or peroxisome proliferators-activated receptor γ-2) using techniques such as Northern blot, RNase protection and RT-PCR. In another embodiment, assays of adipocyte function can be measured, including cytoplasmic accumulation of triglycerides.

4. Neural Differentiation

A method is disclosed herein for differentiating a MIAMI cell into a neural cell, such as a glial cell, oligodendrocyte, or neuron. In specific embodiments, a MIAMI cell is differentiated into a neuron. In one embodiment, neural differentiation is induced by culturing MIAMI cells in a series of neurogenic media. Such neurogenic media can include any medium or any buffer that maintains the viability of the cells and induces neural differentiation in the cells. Numerous culture media are known and are suitable for use (see, for example, Abranches et al., *Biotechnol. Lett.*, 25(9): 725-730, 2003; Calhoun et al., Biochem. Biophys. Res. Commun., 306(1):191-197, 2003; Lou et al., *Brain Res.*, 968(1):114-121, 2003; Stavridis and Smith, *Biochem. Soc. Trans.*, 31(Pt 1):45-49, 2003; Pachernik et al., *Reprod. Nutr. Dev.*, 42(4): 317-326, 2002; Hung et al., *Stem Cells*, 20(6):522-529, 2002).

Generally, neural differentiation proceeds in at least three sequential steps: neural specification, neural commitment, and neural differentiation.

a. Neural Specification

Neural specification is induced by contacting MIAMI cells with a neural specification medium. A neural specification medium includes a minimum essential medium, such as DMEM-HG. A neural specification medium typically contains one or more additional additives, such as serum, antibiotics, growth factors, nutrients, or combinations thereof. Specific non-limiting examples of such additives include serum (from about 5% to about 25% by volume) and bFGF (from about 1 ng/ml to about 100 ng/ml). In particular examples, a neural specification medium includes between about 15% and about 25% serum, such as FBS, or more specifically about 20% FBS. In other examples, a neural specification medium includes between about 5 ng/ml to about 20 ng/ml bFGF, such as between about 7 ng/ml to about 15 ng/ml, or between about 8 ng/ml to about 12 ng/ml bFGF. In one specific example, a neural specification medium includes about 10 ng/ml bFGF.

MIAMI cells are incubated in a neural specification medium for sufficient time to induce neural specification. Such incubation time can be between about 12 hours to about 36 hours, such as about 24 hours.

Neural specification may be determined by any method known in the art. Specific non-limiting examples include morphological determinations (for example, a subpopulation of cells, such as about 30% to about 40% of cells obtain a spherical shape), and expression of stage-specific polypeptide(s) or mRNA(s) for nestin, neuron specific enolase or GFAP. At this stage, cells are generally negative for polypeptides (or mRNAs), such as neuron-specific class III β-tubulin, TrkA, NF-L, NF-M, and NeuN.

b. Neural Commitment

Neural commitment is induced by contacting neurally specified MIAMI cells with a neural commitment medium. A neural commitment medium includes a minimum essential medium, such as DMEM-HG. A neural commitment medium typically contains one or more additional additives, such as antibiotics, growth factors, nutrients, or combinations thereof. Specific non-limiting examples of such additives include βME (from about 0.1 mM to about 10 mM) and NT-3 (from about 1 ng/ml to about 100 ng/ml). In particular examples, a neural commitment medium includes between about 0.5 mM to about 2 mM βME, such as between about 0.7 mM to about 1.5 mM, or between about 0.8 mM to about 1.2 mM βME. In one specific example, a neural commitment medium includes about 1.0 mM βME. In another example, a neural commitment medium includes between about 5 ng/ml to about 20 ng/ml NT-3, such as between about 7 ng/ml to about 15 ng/ml, or between about 8 ng/ml to about 12 ng/ml NT-3. In one specific example, a neural commitment medium includes about 10 ng/ml NT-3. In one, non-limiting example, a neural commitment medium comprises DMEM-HG, 1 mM βME and 10 ng/ml NT-3.

Neurally specified MIAMI cells are incubated in a neural commitment medium for sufficient time to induce neural commitment. Such incubation time can be between about 1 day to about 4 days, such as about 2 days.

Neural commitment may be determined by any method known in the art. Specific non-limiting examples include morphological determinations (for example, up to about 80% of the cells acquire a bipolar spindle shape characteristic of neural cells, and/or cell bodies become increasingly spherical and retractile), functional characteristics (such as, the presence of a resting membrane, for example, between about −40 to about −57 mV), or expression of stage-specific polypeptides and/or mRNA, including for example, decreasing nestin expression, or expression of neuron-specific class III β-tubulin or TrkA in a subpopulation of cells (for example between about 40 to 50% of cells).

c. Neural Differentiation

Neural differentiation is induced by contacting neurally committed M cells with a neural differentiation medium. A neural differentiation medium includes a minimum essential medium, such as DMEM-HG. A neural differentiation medium typically contains one or more additional additives, such as antibiotics, growth factors, nutrients, or combinations thereof. Specific non-limiting examples of such additives include NT-3 (from about 1 ng/ml to about 100 ng/ml), NGF (from about 1 ng/ml to about 100 ng/ml), and BDNF (from about 5 ng/ml to about 500 ng/ml).

In particular examples, a neural differentiation medium includes between about 5 ng/ml to about 20 ng/ml NT-3, such as between about 7 ng/ml to about 15 ng/ml, or between about 8 ng/ml to about 12 ng/ml NT-3. In other examples, a neural differentiation medium includes about 10 ng/ml NT-3. In another example, a neural differentiation medium includes between about 5 ng/ml to about 20 ng/ml NGF, such as between about 7 ng/ml to about 15 ng/ml, or between about 8 ng/ml to about 12 ng/ml NOF. In one specific example, a neural differentiation medium includes about 10 ng/ml NGF. In still other examples, a neural differentiation medium includes between about 25 ng/ml to about 100 ng/ml BDNF, such as between about 30 ng/ml to about 75 ng/ml, or between about 40 ng/ml to about 60 ng/ml BDNF. In one specific example, a neural differentiation medium includes about 50 ng/ml BDNF.

In one, non-limiting example, a neural differentiation medium comprises DMEM-HG, about 10 ng/ml NT-3, about 10 ng/ml NGF, and about 50 ng/ml BDNF.

Neurally committed MIAMI cells are incubated in a neural differentiation medium for sufficient time to induce neural differentiation. Such incubation time can be between about 1 day to about 14 days, such as between about 3 days to about 7 days.

Neural differentiation may be determined by any method known in the art. Specific non-limiting examples include morphological determinations (for example, typical neural perikaryal appearance, neurite outgrowth and arborization), functional characteristics (such as, the presence of a resting membrane, for example, between about −40 to about −60 mV, capacitance of about 5 to about 8 pF, and inward and outward currents upon depolarization), or expression of neuron-specific polypeptides and/or mRNA, including for example, NeuN and neurofilament (for example, NF-L or NF-M).

5. Differentiation to Pancreatic Islet-Like Cells

A method is disclosed herein for differentiating a MIAMI cell into a pancreatic islet-like cell, such as a β-like cell. Cells are treated according to a sequential protocol of specification, commitment, and differentiation under conditions to promote the expression of a β-cell-like phenotype (see, for example, Movassat et al., *J. Clin. Endocrinol. Metab.*, 87:4775-4781, 2002; Hunziker and Stein, *Biochem. Biophys. Res. Commun.*, 271:116-119, 2000; Zulewski et al., *Diabetes*, 50:521-533, 2001; Lumelsky et al., *Science*, 292:1389-1394, 2001; WO 02/059278). In some examples, a pre-conditioning step is included prior to specification.

a. Pre-Conditioning

MIAMI cells are optionally pre-conditioned for β-cell-like differentiation by contacting the cells with a pre-conditioning medium. A preconditioning medium includes a minimum essential medium, such as DMEM-HG. A pre-conditioning medium typically contains one or more additional additives, such as serum, antibiotics, growth factors, nutrients, or combinations thereof. Specific non-limiting examples of such additives include serum (from about 5% to about 25% by volume) and bFGF (from about 1 ng/ml to about 100 ng/ml). In particular examples, a pre-conditioning medium includes between about 15% and about 25% serum, such as FBS, or more specifically about 20% FBS. In other examples, a pre-conditioning medium includes between about 5 ng/ml to about 20 ng/ml bFGF, such as between about 7 ng/ml to about 15 ng/ml, or between about 8 ng/ml to about 12 ng/ml bFGF. In one specific example, a pre-conditioning medium includes about 10 ng/ml bFGF.

In specific embodiments, MIAMI cells are incubated in a pre-conditioning medium for between about 12 hours to about 36 hours, such as for about 24 hours.

b. Specification

β-cell-like specification is induced by contacting MIAMI cells (or pre-conditioned MIMI cells) with a specification medium. A specification medium includes a minimum essential medium, such as DMEM-HG. A specification medium typically contains one or more additional additives, such as antibiotics, growth factors, nutrients, or combinations thereof. Specific non-limiting examples of such additives include DMSO (from about 0.1% to about 10%), butylated hydroxyanisole (BHA) (from about 10 μM to about 1000 μM), and exendin-4 (from about 1 nM to about 100 nM).

In particular examples, a specification medium includes between about 0.5% to about 2% DMSO, such as between about 0.7% to about 1.5%, or between about 0.8% to about 1.2% DMSO. In one specific example, a specification medium includes about 1.0% DMSO. In another example, a specification medium includes between about 50 μM to about 200 μM BHA, such as between about 70 μM to about 150 μM, or between about 80 μM to about 120 μM BHA. In one specific example, a specification medium includes about 100 μM BHA. In yet another example, a specification medium includes between about 5 nM to about 20 nM exendin-4, such as between about 7 nM to about 15 nM, or between about 8 nM to about 12 nM exendin-4. In one specific example, a specification medium includes about 10 nM exendin-4.

In one, non-limiting example, a specification medium comprises DMEM-HG, 1% DMSO, 100 μM BHA, and 10 nM exendin-4.

MIAMI cells (or pre-conditioned MIAMI cells) are incubated in a specification medium for sufficient time to induce specification. Such incubation time can be between about 1 day to about 4 days, such as about 2 days.

Specification may be determined by any method known in the art. Non-limiting examples of β-cell-like specification include morphological determinations (for example, formation of small non-adherent spherical cell clusters) and increased expression of islet-specific polypeptides and/or mRNA, including for example, ISL-1 and Beta-2/Neuro-D.

c. Commitment

β-cell-like commitment is induced by contacting β-cell-specified MIAMI cells with a commitment medium. A commitment medium includes a minimum essential medium, such as RPMI (GIBCO). A commitment medium typically contains one or more additional additives, such as serum, antibiotics, growth factors, nutrients, or combinations thereof. Specific non-limiting examples of such additives are included in Table 5.

TABLE 5

β-Cell-Like Commitment Media Supplements

| Additive | Exemplary Concentration |
| --- | --- |
| serum | About 5% to about 25% |
| glucose | About 1 mM to about 110 mM |
| HEPES | About 1 mM to about 100 mM |
| sodium pyruvate | About 0.1 mM to about 10 mM |
| bFGF | About 2 ng/ml to about 200 ng/ml |
| EGF | About 2 ng/ml to about 200 ng/ml |
| exendin-4 | About 1 nM to about 100 nM |

In one embodiment, the commitment medium includes at least bFGF, EGF, and exendin-4. In one specific example, the commitment medium includes between about 10 ng/ml to about 40 ng/ml bFGF, such as for example between about 15 ng/ml to about 30 ng/ml, or between about 18 ng/ml to about 25 ng/ml bFGF. In yet another example, the commitment medium includes about 20 ng/ml bFGF. In another embodiment, the commitment medium includes between about 10 ng/ml to about 40 ng/ml EGF, such as for example between about 15 ng/ml to about 30 ng/ml, or between about 18 ng/ml to about 25 ng/ml EGF. In yet another example, the commitment medium includes about 20 ng/ml EGF. In another specific example, the commitment medium includes between about 5 nM to about 20 nM exendin-4, such as for example between about 7 nM to about 15 nM, or between about 8 nM to about 12 nM exendin-4. In yet another example, the adipogenic medium includes about 10 nM exendin-4.

In one, non-limiting example, treated MIAMI cells are contacted with a commitment medium comprising RPMI, 10% FBS, 11 mM glucose, 10 mM HEPES, 1.0 mM sodium pyruvate, 20 ng/ml bFGF, 20 ng/ml EGF, and 10 nM exendin-4.

β-cell-specified MIAMI cells are incubated in a commitment medium for sufficient time to induce β-cell-like commitment. Such incubation time can be between about 2 days to about 8 days, such as between about 3 days to about 6 days, or more specifically about 4 days.

β-cell-like commitment may be determined by any method known in the art. Specific non-limiting examples include morphological determinations (for example, increase in size and number of non-adherent spherical and oblong cell clusters) and increased expression of β-cell-specific polypeptides and/or mRNA, including for example, Nkx6.1.

d. Differentiation

β-cell-like differentiation is induced by contacting β-cell-like committed MIAMI cells with a differentiation medium. A differentiation medium includes a minimum essential medium, such as RPMI (GIBCO). A differentiation medium typically contains one or more additional additives, such as serum, antibiotics, growth factors, nutrients, or combinations thereof. Specific non-limiting examples of such additives are included in Table 6.

TABLE 6

β-Cell-Like Differentiation Media Supplements

| Additive | Exemplary Concentration |
| --- | --- |
| glucose | About 0.25 mM to about 25 mM |
| HEPES | About 1 mM to about 100 mM |
| nicotinamide | About 1 mM to about 100 mM |
| HGF | About 10 pM to about 1000 pM |
| exendin-4 | About 1 nM to about 100 nM |
| activin-A | About 0.2 nM to about 20 nM |

In one embodiment, the differentiation medium includes at least glucose, nicotinamide, HGF, exendin-4, and activin-A. In one specific example, the differentiation medium includes between about 1.0 mM to about 5.0 mM glucose, such as for example between about between about 1.5 mM to about 4.0 mM, or between about 1.5 mM to about 3.5 mM glucose. In a more specific example, the differentiation medium includes about 2.5 mM glucose. In another embodiment, the differentiation medium includes between about 5 mM to about 20 mM nicotinamide, such as for example between about 7 mM to about 15 mM, or between about 8 mM to about 12 mM nicotinamide. In a more specific embodiment, the differentiation medium includes about 10 mM nicotinamide. In another embodiment, the differentiation medium includes between about 50 pM to about 200 pM HGF, such as for example between about 75 pM to about 150 pM, or between about 80 pM to about 120 pM HGF. In a more specific embodiment, the differentiation medium includes about 100 pM HGF. In another embodiment, the differentiation medium includes between about 5 nM to about 20 nM exendin-4, such as for example between about 7.5 nM to about 15 nM, or between about 8 nM to about 12 nM exendin-4. In a more specific embodiment, the differentiation medium includes about 10 nM exendin-4. In another embodiment, the differentiation medium includes between about 0.5 nM to about 5.0 nM activin-A, such as for example between about 0.75 nM to about 3.5 nM, or between about 1 nM to about 3 nM activin-A. In a more specific embodiment, the differentiation medium includes about 2.0 nM activin-A.

In one, non-limiting example, β-cell-like committed MIAMI cells are contacted with a differentiation medium comprising RPMI, 2.5 mM glucose, 10 mM HEPES, 10 mM nicotinamide, 100 pM HGF, 10 nM exendin-4, and 2.0 nM activin-A.

β-cell-like committed MIAMI cells are incubated in a differentiation medium for sufficient time to induce β-cell-like differentiation Such incubation time can be between about 2 days to about 14 days, such as between about 3 days to about 10 days, or more specifically about 5 days to about 7 days.

β-cell-like differentiation may be determined by any method known in the art. Specific non-limiting examples include expression of β-cell-like polypeptides and/or mRNAs, including for example Beta2/NeuroD, Nkx6.1, Isl1, insulin and glucagon, and morphological characteristics, such as attachment-independent spherical or oblong clusters.

VII. Methods of Using Multilineage-Inducible Cells

Methods are provided for treating a subject suffering from a disease or a disorder, such as a neural disorder, a cartilage disorder, a bone disorder, or diabetes, or alleviating the symptoms of such a disorder, by administering cells isolated and cultured according to the methods disclosed. The cells can be administered alone or in conjunction with another pharmaceutical agent, such as a growth factor or immunosuppressive agent.

1. Generally Applicable Methods

In one embodiment, MIAMI cells are isolated as described herein and a therapeutically effective amount of MIAMI cells is administered to the subject. In another embodiment, MIAMI cells are isolated and differentiated (as described above) into a cell type useful for the desired treatment, for example into osteoblasts, chondrocytes, neurons, adipocytes, or β-like cells, and a therapeutically effective amount of the differentiated cells are administered to a subject, such as a human.

The cells may be administered in any fashion, for example in a dose of, for example about $10^5$ to about $10^8$ cells, such as about $10^6$ cells. Different dosages can of course be used depending on the clinical circumstances. The cells may be administered systemically (for example intravenously) or locally (for example directly into the brain, the pancreas, a soft tissue, a bone or joint, as applicable). In another example, the cells can be administered in a gel matrix (such as Gelfoam from Upjohn Company) which polymerizes to form a substrate in which the administered cells can grow.

In one embodiment the MIAMI cells or differentiated MIAMI cells are administered systemically by injection. Specific, non-limiting examples include administration by subcutaneous injection, intramuscular injection, or intravenous injection. If administration is intravenous, an injectible liquid suspension of MIAMI cells can be prepared and administered by a continuous drip or as a bolus.

In another embodiment, the MIAMI cells or differentiated MIAMI cells are administered locally. One specific, non-limiting example of local administration is by injection. The site of local administration will depend upon the particular disorder being treated. In some embodiments, MIAMI cells (or differentiated MIAMI cells) are in an injectable liquid suspension preparation or in a biocompatible medium which is injectible in liquid form and becomes semi-solid at the desired site, such as in a bone, joint, or soft tissue. A conventional syringe or a controllable endoscopic delivery device can be used so long as the needle lumen or bore is of sufficient diameter (for example, 30 gauge or larger) that shear forces will not damage the MIAMI cells.

In other embodiments, MIAMI cells or differentiated MIAMI cells are administered locally on a support medium. One specific, non-limiting example of a support medium is a sterile mesh, or matrix, upon which the MIAMI cells are cultured. In one embodiment, the support medium is a biodegradable mesh. In another embodiment, the support medium is not biodegradable. The size of the mesh, and the density of cells on it, can vary depending on the defect being treated.

In another embodiment, the cells are encapsulated prior to administration, such as by co-incubation with a biocompatible matrix known in the art. A variety of encapsulation technologies have been developed (for example, Lacy et al., *Science*, 254:1782-1784, 1991; Sullivan et al., *Science*, 252:718, 1991; WO 91/10470; WO 91/10425; U.S. Pat. No. 5,837,234; U.S. Pat. No. 5,011,472; U.S. Pat. No. 4,892,538).

The cells can be repeatedly administered at intervals until a desired therapeutic effect is achieved. In certain embodiments, MIAMI cells may be isolated from the subject requiring treatment to avoid rejection of administered cells.

Isolated MIAMI cell can be transduced using standard procedures known in molecular biology in order to introduce a nucleic acid molecule of interest into the cell. In one embodiment, the nucleic acid molecule encodes a polypeptide. The polypeptide encoded by the nucleic acid molecule can be from the same species as the cells (homologous), or can be from a different species (heterologous). For example, a nucleic acid molecule can be utilized that supplements or replaces deficient production of a peptide by the tissue of the host wherein such deficiency is a cause of the symptoms of a particular disorder. In this case, the cells act as a source of the peptide.

In one embodiment, the nucleic acid sequence of interest is operably linked to a regulatory element, such as a transcriptional and/or translational regulatory element. Regulatory elements include elements such as a promoter, an initiation codon, a stop codon, mRNA stability regulatory elements, and a polyadenylation signal. A promoter can be a constitutive promoter or an inducible promoter. Specific non-limiting examples of promoters include the immunoglobulin promoter, or a T cell specific promoter, and promoters including TET-responsive element for inducible expression of transgene. In another embodiment, the nucleic acid sequence of interest is inserted into a vector, such as an expression vector. Procedures for preparing expression vectors are known to those of skill in the art and can be found in Sambrook et al., *Molecular Cloning: A Laboratory Manual*, 2nd Ed., Cold Spring Harbor Press, Cold Spring Harbor, N.Y. (1989). Expression of the nucleic acid of interest occurs when the expression vector is introduced into an appropriate host cell. The vector can be a viral vector, such as an adenoviral or retroviral vector.

Retroviral vectors of use are produced recombinantly by procedures already taught in the art. For example, WO 94/29438 describes the construction of retroviral packaging plasmids and packaging cell lines. The techniques used to construct vectors, and transfect and infect cells are widely practiced in the art. Examples of retroviral vectors are those derived from murine, avian or primate retroviruses. Retroviral vectors based on the Moloney (Mo) murine leukemia virus (MuLV) are the most commonly used because of the availability of retroviral variants that efficiently infect human cells. Other suitable vectors include those based on the Gibbon Ape Leukemia Virus (GALV) or HIV.

In producing retroviral vector constructs derived from the Moloney murine leukemia virus (MoMLV), in most cases, the viral gag, pol and env sequences are removed from the virus, creating room for insertion of foreign DNA sequences. Genes encoded by the foreign DNA are usually expressed under the control of the strong viral promoter in the LTR. Such a construct can be packed into viral particles efficiently if the gag, pol and env functions are provided in trans by a packaging cell line. Thus, when the vector construct is introduced into the packaging cell, the gag-pol and env proteins produced by the cell, assemble with the vector RNA to produce infectious virions that are secreted into the culture medium. The virus thus produced can infect and integrate into the DNA of the target cell, but does not produce infectious viral particles since it is lacking essential packaging sequences. Most of the packaging cell lines currently in use have been transfected with separate plasmids, each containing one of the necessary coding sequences, so that multiple recombination events are necessary before a replication competent virus can be produced. Alternatively, the packaging cell line harbors an integrated provirus. The provirus has been crippled so that, although it produces all the proteins required to assemble infectious viruses, its own RNA cannot be packaged into virus. Instead, RNA produced from the recombinant virus is packaged. The virus stock released from the packaging cells thus contains only recombinant virus.

The range of host cells that may be infected by a retrovirus or retroviral vector is determined by the viral envelope protein. The recombinant virus can be used to infect virtually any other cell type recognized by the env protein provided by the packaging cell, resulting in the integration of the viral genome in the transduced cell and the stable production of the foreign gene product. In general, murine ecotropic env of MoMLV allows infection of rodent cells, whereas amphotropic env allows infection of rodent, avian and some primate cells, including human cells. Amphotropic packaging cell lines for use with MoMLV systems are known in the art and commercially available and include, but are not limited to, PA 12 and PA317 (Miller et al., *Mol. Cell. Biol,* 5:431437, 1985; Miller et al., *Mol Cell. Biol.,* 6:2895-2902, 1986; and Danos et al., *Proc. Natl. Acad. Sci. USA,* 85:6460-6464, 1988. Xenotropic vector systems exist which also allow infection of human cells (U.S. Pat. No. 5,638,928).

According to this example, cells are cultured in vitro as described herein and an exogenous nucleic acid is introduced into the cells by any method known to one of skill in the art, for example, by transfection or electroporation. The transfected cultured cells can then be studied in vitro or can be administered to a subject. Methods for the introduction of nucleic acid sequences into multilineage-inducible cells are known in the art (e.g., see U.S. Pat. No. 6,110,743).

2. Specific Treatments a. Bone Disorders

In certain embodiments, MIAMI cells or MIAMI cells induced to undergo osteogenic differentiation may be administered to a subject having a bone disorder. Examples of bone disorders include, without limitation, arthritis, osteoporosis, osteosclerotic metaphyseal dysplasia, osteomyelitis, Paget's disease of bone, hypophosphatasia, osteopetrosis, osteomalacia, or bone fracture (such as, resulting from physical trauma or secondary to other bone malformations).

MIAMI cells may be used in any manner known in the art to treat such bone disorders (for example, Murphy et al., *Arthritis Rheum.*, 48(12): 3464-3474, 2003; Dragoo et al., *J. Bone Joint Surg. Br.*, 85(5):740-747, 2003; Peng and Huard, *Curr. Opin. Pharmacol.*, 3(3):329-333, 2003; Pelled et al., *Curr. Pharm. Des.*, 8(21):1917-1928, 2002), including those methods discussed above.

MIAMI cells or MIAMI cells induced to undergo osteogenic differentiation may also be useful for in vitro bone tissue engineering.

b. Cartilage Disorders

In some methods, MIAMI cells or MIAMI cells induced to undergo chondrogenic differentiation may be administered to a subject having a cartilage disorder. Examples of cartilage disorders include, without limitation, arthritis, pseudoachondroplasia, articular cartilage degeneration, osteogenesis imperfecta, or cartilage disruptions (such as, tearing) resulting from physical trauma (for example, as a result of a sport injury).

MIAMI cells may be used in any manner known in the art to treat such cartilage disorders (for example, Murphy et al., *Arthritis Rheum.*, 48(12): 3464-3474, 2003; Dragoo et al., *J. Bone Joint Surg. Br.*, 85(5):740-747, 2003; Peng and Huard, *Curr. Opin. Pharmacol.*, 3(3):329-333, 2003; Barry, *Novartis Found. Symp.*, 249:175-186, 2003; Pelled et al., *Curr. Pharm. Des.*, 8(21):1917-1928, 2002), including those methods discussed above.

MIAMI cells or MIAMI cells induced to undergo chondrogenic differentiation may also be useful for in vitro cartilage tissue engineering.

c. Adipocyte Treatments

MIAMI cells or MIAMI cells induced to undergo adipogenic differentiation may be useful fat augmentation in the body. For example, such cells may be injected into regions of the body where additional volume in required or desired, such as in cosmetic surgery applications. In particular examples, the cells may be injected into the lips, breasts, cheeks, or brows of an individual. Alternatively, the cells may be injected to "fill" wrinkles in the face or elsewhere on the body. Other examples include use of such cells to cosmetically correct scarring anywhere on a subject's body.

d. Neurological Disorders

In one embodiment, MIAMI cells or MIAMI cells induced to undergo neural differentiation may be administered to a subject having a neurological disorder (including neurogenerative disorders). Examples of neurological disorders include Parkinson's disease, Huntington's disease, Alzheimer's disease, severe seizure disorders including epilepsy, familial dysautonomia as well as injury or trauma to the nervous system, such as neurotoxic injury, spinal cord injury, or stroke, or disorders of mood and behavior such as addiction, schizophrenia and amyotrophic lateral sclerosis. Neural disorders also include Lewy body dementia, multiple sclerosis, cerebellar ataxia, progressive supranuclear palsy, affective disorders, anxiety disorders, obsessive compulsive disorders, personality disorders, attention deficit disorder, attention deficit hyperactivity disorder, Tourette Syndrome, Tay Sachs, Nieman Pick, and other lipid storage and genetic brain diseases and/or pantothenate kinase associated neurodegeneration, and HIV encephalopathy (Miszkziel et al., *Magnetic Res. Imag.*, 15:1113-1119, 1997).

In some embodiments, cells may be locally administered in the brain, spinal cord, or peripheral nervous system, using methods discussed above. Laboratory and clinical studies have shown the transplantation of cells into the CNS is a potentially significant alternative therapeutic modality for neurodegenerative disorders such as Parkinson's disease (Borlongan et al., *J. Fla. Med. Assoc.*, 81(10):689-694, 1994; Wictorin et al., *Nature*, 347:556-558, 1990; Lindvall et al., *Science*, 247:574-557, 1990; *Neural Grafting in the Mammalian CNS*, ed. by Bjorklund and Stenevi, New York:Elsevier Science Ltd, 1985). In some cases, transplanted neural tissue can survive and form connections with the CNS of the recipient, for example, the host (Wictorin et al., *Nature*, 347:556-558, 1990). When successfully accepted by the host, the transplanted cells and/or tissue have been shown to ameliorate the behavioral deficits associated with the disorder (Borlongan et al., *J. Fla. Med. Assoc.*, 81(10):689-694, 1994). The obligatory step for the success of this kind of treatment is to have enough viable cells available for the transplant. The culturing conditions described herein can be used to differentiate MIAMI cells into neural cells useful for transplantation.

Methods of grafting cells are now well known to those of skill in art (U.S. Pat. Nos. 5,762,926; 5,650,148; 5,082,670). Neural transplantation or grafting involves transplantation of cells into the central nervous system or into the ventricular cavities or subdurally onto the surface of a host brain. Conditions for successful transplantation include: (a) viability of the implant; (b) retention of the graft at the site of transplantation; and (c) minimum amount of pathological reaction at the site of transplantation.

Methods for transplanting various nerve tissues, for example MIAMI cells or neurally differentiated MIAMI cells, into host brains have been described in *Neural Grafting in the Mammalian CNS* (ed. by Bjorklund and Stenevi, New York:Elsevier Science Ltd, 1985; see, Das, Ch. 3 pp. 23-30; Freed, Ch. 4, pp. 31-40; Stenevi et al., Ch. 5, pp. 41-50; Brundin et al., Ch. 6, pp. 51-60; David et al., Ch. 7, pp. 61-70; Seiger, Ch. 8, pp. 71-77). These procedures include intraparenchymral (within the host brain) transplantation (as compared to outside the brain or extraparenchymal transplantation) achieved by injection or deposition of tissue within the host brain so as to be opposed to the brain parenchyma at the time of transplantation.

The two main procedures for intraparenchymal transplantation are (a) injecting the transplanted cells within the host brain parenchyma or (b) preparing a cavity by surgical means to expose the host brain parenchyma and then depositing the graft into the cavity. Both methods provide parenchymal apposition between the graft and host brain tissue at the time of grafting, and both facilitate anatomical integration between the graft and host brain tissue. This is of importance if it is required that the graft become an integral part of the host brain and to survive for the life of the host.

Alternatively, the graft may be placed in a ventricle, for example, a cerebral ventricle or subdurally (on the surface of the host brain) where it is separated from the host brain parenchyma by the intervening pia mater or arachnoid and pia mater. Grafting to the ventricle may be accomplished by injection of the transplanted cells or by growing the cells in a substrate such as 3% collagen to form a plug of solid tissue which may then be implanted into the ventricle to prevent dislocation of the graft. For subdural grafting, the cells may be injected around the surface of the brain after making a slit in the dura. Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord. The transplanted cells may also be introduced into the putamen, nucleus basalis, hippocampus cortex, striatum or caudate regions of the brain, as well as the spinal cord.

For grafting, the cell suspension is drawn up into the syringe and administered to anesthetized graft recipients. Multiple injections may be made using this procedure. The cellular suspension procedure thus permits grafting of transplanted cells to any predetermined site in the brain or spinal cord, is relatively non-traumatic, allows multiple grafting simultaneously in several different sites or the same site using the same cell suspension, and permits mixtures of cells from different anatomical regions. Multiple grafts may consist of a mixture of cell types, and/or a mixture of transgenes inserted into the cells. Preferably from approximately $10^4$ to approximately $10^8$ cells are introduced per graft.

For transplantation into cavities, which may be preferred for spinal cord grafting, tissue is removed from regions close to the external surface of the CNS to form a transplantation cavity, for example by removing bone overlying the brain and stopping bleeding with a material such a gelfoam (Stenevi et al., *Brain Res.*, 114:1-20, 1976). Suction may be used to create the cavity. The graft is then placed in the cavity. More than one transplant may be placed in the same cavity.

Grafting of transplanted cells into a traumatized brain will require different procedures, for example, the site of injury must be cleaned and bleeding stopped before attempting to graft. In addition, the transplanted cells should possess sufficient growth potential to fill any lesion or cavity in the host brain to prevent isolation of the graft in the pathological environment of the traumatized brain.

e. Diabetes

In certain methods, MIAMI cells or MIAMI cells induced to undergo β-cell-like differentiation may be administered to a subject having diabetes. MIAMI cells (or differentiated MIAMI cells) useful for the treatment of diabetes may, for example, be injected directly into the pancreas, transplanted elsewhere in the body, or may be adhered to a biopolymer (as discussed above) and surgically inserted into an acceptable location in the body.

MIAMI cells or MIAMI cells differentiated to β-like cells can be administered by any method known to one of skill in the art. In one specific, non-limiting example the cells are administered by subcutaneous injection, or by implantation under the kidney capsule, through the portal vein of the liver, or into the spleen. In one embodiment, about 1,000 to about 10,000 cells are implanted. If, based on the method of administration, cell survival after transplantation in general is low (5-10%), an estimated 14 million MIAMI cells or MIAMI cells differentiated to Alike cells are transplanted.

In one embodiment, transplantation is done by injection. Injections can generally be made with a sterilized syringe having an 18-23 gauge needle. Although the exact size needle will depend on the species being treated, and whether a cell suspension or an artificial islet is transplanted, the needle should not be bigger than 1 mm diameter in any species. As used herein, "artificial islets" are clusters of β-like cells derived from MIAMI cells formed by the differentiation of MIAMI cells in vitro. The injection can be made via any means known to one of skill in the art. Specific, non-limiting examples include subcutaneous injection, intraperitoneal injection, injection under the kidney capsule, injection through the portal vein, and injection into the spleen.

In one embodiment, the cells are encapsulated prior to administration, such as by co-incubation with a biocompatible matrix known in the art (as discussed above).

MIAMI cells or β-cell-like differentiated MIAMI cells may be implanted using an alginate-polylysine encapsulation technique (O'Shea and Sun, *Diabetes,* 35:943-946, 1986; Frischy et al., *Diabetes,* 40:37, 1991). In this method, the cells are suspended in 1.3% sodium alginate and encapsulated by extrusion of drops of the cell/alginate suspension through a syringe into $CaCl_2$. After several washing steps, the droplets are suspended in polylysine and rewashed. The alginate within the capsules is then reliquified by suspension in 1 mM EGTA and then rewashed with Krebs balanced salt buffer. Each capsule is designed to contain several hundred cells and have a diameter of approximately 1 mm. Capsules containing cells are implanted (approximately 1,000-10,000/animal) intraperitoneally and blood samples taken daily for monitoring of blood glucose and insulin.

Other methods for implanting islet substitutes into mammals have been described (Lacy et al., *Science,* 254:1782-1784, 1991; Sullivan et al., *Science,* 252:718-721, 1991; U.S. Pat. No. 5,993,799). In one specific, non-limiting example, MIAMI cells or β-like cells derived from MIAMI cells are encapsulated in hollow acrylic fibers and immobilized in alginate hydrogel. These fibers are then transplanted intraperitoneally or subcutaneously implants.

In another embodiment, MIAMI cells or β-like cells derived from MIAMI cells can be administered as part of a biohybrid perfused "artificial pancreas", which encapsulates the cells in a selectively permeable membrane (Sullivan et al., *Science,* 252:718-721, 1991). In this method, a tubular semipermeable membrane is coiled inside a protective housing to provide a compartment for the islet cells. Each end of the membrane is then connected to an arterial polytetrafluoroethylene (PTFE) graft that extends beyond the housing and the device is joined to the vascular system as an arteriovenous shunt. Other suitable methods are known to those of skill in the art.

VIII. Use of MIAMI Cells to Screen for Agents that Induce Differentiation

Methods are provided for screening agents that induce differentiation. According to this method, a population of MIAMI cells is produced as described above. The population of cells is contacted with an agent of interest, and the effect of the agent on the cell population is then assayed. Differentiation of some or all of the MIAMI cells identifies the agent as a differentiation-inducing agent.

An agent may induce MIAMI cells to differentiate into cells of endodermal, endodermal or mesodermal origin. In some instances, MIAMI cells can undergo chondrogenic differentiation, osteogenic differentiation, adipogenic differentiation, neural differentiation, or β-cell-like differentiation.

Differentiation of MIAMI cells contacted with an agent can be assessed by any means known to one of skill in the art, including those methods described herein. Such methods include, without limitation, morphological, biochemical, or functional determinations.

In one embodiment, morphology of cells contacted with a test agent is examined, for example by light or electron microscopy. Suitable parameters for morphological evaluation include, size and shape of the cells, for example an agent that induces neural differentiation may result in cells assuming a perikaryal appearance possibly with neurite outgrowth and arborization; alternatively, an agent that induces β-cell-like differentiation may result in cells assuming attachment-independent clusters.

In other embodiments, functional assays are performed, for example, resting membrane potential or depolarization-induced currents may be measured in cells undergoing neural differentiation in response to an agent. Cells undergoing osteogenic differentiation in response to an agent may be assayed for alkaline phosphatase activity, in vitro mineralization, or in vitro production of extracellular matrix or bone nodules. Cells undergoing chondrogenic and adipogenic differentiation in response to an agent may be assayed for production of a proteoglycan-rich soft collagen matrix and triglycerides, respectively.

In other embodiments, immunohistochemical or immunofluorescence techniques are used to assess differentiation. In yet another embodiment, differentiation is assessed by analysis expression of specific mRNA molecules expressed in differentiated cells. Suitable assay systems include, but are not limited to RT-PCR, in situ hybridization, Northern analysis, or RNase protection assays. In a further embodiment the levels of polypeptides expressed in differentiated cells are assayed. Specific, non-limiting examples of polypeptide assays of use include Western blot analysis, ELISA assay, or immunofluorescence.

In one embodiment, cells contacted with the agent are compared with a control. Suitable controls include MIAMI cells not contacted with the agent, or contacted with vehicle alone. Standard values can also be used as a control.

IX. Kits

The cells described herein are ideally suited for the preparation of a kit. The kit can include a carrier means, such as a box, a bag, or plastic carton. In one embodiment, the carrier contains one or more containers such as vials, tubes, and the like that include a sample of MIAMI cells. In another embodiment, the carrier includes a container with an agent that affects differentiation, a buffer, or a vehicle for the introduction of the cells. Instructions can be provided to detail the use of the components of the kit, such as written instructions, video presentations, or instructions in a format that can be opened on a computer (for example, a diskette or CD-ROM disk). These instructions indicate, for example, how to administer the cells to treat a disease or defect or how to use the cells to screen test agents of interest (such as differentiation-inducing drugs).

The following examples are provided to illustrate certain particular features and/or embodiments. These examples should not be construed to limit the invention to the particular features or embodiments described.

EXAMPLES

Example 1

Isolation and Characterization of MIAMI Cells

This example demonstrates the isolation, characterization and expansion of novel multipotent cells obtained from postnatal, human bone marrow.

1. Materials and Methods a. Cytokines

Human recombinant hepatocyte growth factor (HGF), basic-fibroblast growth factor (b-FGF), epidermal growth factor (EGF), and exendin-4 were from Sigma Chemical (St. Louis, Mo.); β-nerve growth factor (NGF), neurotrophin-3 (NT-3), brain-derived neurotrophic factors (BDNF), were from Calbiochem (San Diego, Calif.); and transforming growth factor-β3 (TGF-β3) and activin-A were from R&D (Minneapolis, Minn.).

b. Antibodies

The following primary antibodies were used for immunocytochemistry: neuron-specific enolase (NSE), neurofilament-M, nestin, neuronal nuclear protein (Neu-N), glial fibrillary acid protein (GFAP), and NGF receptor (TrkA) were obtained from Chemicon (Temecula, Calif.); neuron-specific class III β-tubulin (antibody referred to as TuJ1) was obtained from Covance (Princeton, N.J.); NT-3 receptor (NTRK-3) was obtained from Santa Cruz Biotechnology (Santa Cruz, Calif.).

The following primary antibody was used for immunoblotting: cMet, which was obtained from Santa Cruz Biotechnology.

The following primary antibodies were used for flow cytometry: CD10, CD29, CD34, CD36, CD49e, CD45, CD54, CD56, CD63, CD81, CD103, CD117, BMPR-1B, CNRTR, Flt-1, Flk-1, NTRK3, and HLA-DR were obtained from Santa Cruz Biotechnology and CD44, CD90, CD109, CD122, and CD164 were obtained from BD-Pharmigen (San Diego, Calif.).

c. Bone Marrow and Cells

Whole bone marrow was obtained from vertebral bodies (T1-L5) of 12 normal, previously healthy cadaveric male and female donors who died of fatal traumatic injury (age range; 3-72 years old: #519 [3-year-old boy], #849 [7-year-old boy], #769 [10-year-old boy], #657 [3-year-old girl], #764 [11-year-old girl], #645 [14-year-old girl], #502 [40-year-old man], #869 [55-year-old man], #812 [72-year-old man], #619 [42-year-old woman], #507 [55-year-old woman], and #889 [59-year-old woman]), following guidelines for informed consent set by the University of Miami School of Medicine Committee on the Use of Human Subjects in Research. Vertebral bodies were removed from the donors within two hours after the heart stopped beating.

Whole bone marrow, adherent and nonadherent cells, was plated (without prior gradient centrifugation, immunoselection, or immunodepletion) at a constant density of $10^5$ cells/$cm^2$ (D'Ippolito et al., *J. Bone Miner. Res.*, 14:1115-1122, 1999) in fibronectin-coated 15-cm dishes. The human foreskin fibroblast cell line hTERT-BJ1 that stably expresses exogenous human telomerase reverse transcriptase (hTERT) was obtained from BD Bioscience Clontech (Palo Alto, Calif.). The prostate cancer cell line PC-3, which expresses high levels of cMet, was obtained from Dr. Carlos Perez- Stable, at the University of Miami School of Medicine. The primary human pancreatic islet cells were obtained from Dr. Antonello Pillegi, at the University of Miami School of Medicine.

d. Selection/Expansion of MIAMI Cells

Whole bone marrow cells (without gradient centrifugation, immunoselection, or immunodepletion) from cadaveric thoracolumbar (T1-L5) vertebral bodies were plated at a constant density of $10^5$ cells/cm$^2$ in DMEM-low glucose media, containing 5% fetal bovine serum (FBS) and 100 U/ml penicillin/1000 U streptomycin in fibronectin-coated 10-cm dishes. Whole bone marrow cells, containing adherent and nonadherent cells, were maintained in a humidified incubator at 37° C. undisturbed in an atmosphere of 3% $O_2$/5% $CO_2$/92% $N_2$; 7 days later half of the culture medium was replaced. Fourteen days after the initial plating, the nonadherent cells were removed. Under these conditions the highest number of single-cell-derived colonies ($\geq$50 cells) per number of whole bone marrow cells plated could be obtained at 14 days after the initial plating.

Single-cell-derived (isolated using cloning rings) and pooled colonies of adherent cells were carefully rinsed in medium and removed by treatment with trypsin/EDTA. These cells were selected and expanded at low density ($\leq$30% confluency) by plating single-cell-derived or pooled colonies in fibronectin (10 ng/mL)-coated dishes using an expansion medium composed of: 98% DMEM-low glucose, 2% FBS, and 100 U/ml penicillin/1000 U streptomycin (Gibco-BRL) at 3% $O_2$/5% $CO_2$/92% $N_2$.

e. Differentiation Culture Conditions

Osteogenic Differentiation: For osteogenic differentiation cells derived from single-cell-derived or pooled colonies were plated at 10,000 cells/cm$^2$ in 6-well plates (Costar, Cambridge, Mass.) in the presence of α-MEM/10% FBS with 100 U/ml penicillin (GIBCO-BRL), 1 mg/ml streptomycin (GIBCO-BRL), 100 µM ascorbic acid 2-phosphate, and 10 mM β-glycerophosphate (D'Ippolito et al., *J. Bone Miner. Res.*, 14:1115-1122, 1999; D'Ippolito et al., *Bone*, 31:269-275, 2002). The next day, dexamethasone (Dex, Sigma, St. Louis, Mo.) dissolved in DMSO was added to a final concentration of 10 nM. DMSO at the final concentration of 0.001% was used as vehicle. The medium was changed twice a week.

Chondrogenic Differentiation: For chondrogenic differentiation (Mackay, *Tissue Eng.*, 4:415-428, 1998), cells were trypsinized, washed in serum-containing medium, and resuspended in serum-free chondrogenic medium composed of DMEM high-glucose (DMEM-HG), 100 nM Dex, 10 ng/ml TGF-β3, 50 µg/ml ascorbic acid 2-phosphate, 100 µg/ml sodium pyruvate, 40 µg/ml proline, and ITS-plus (Collaborative Biomedical Products, final concentrations: 6.25 µg/ml bovine insulin, 6.25 µg/ml transferrin, 6.25 µg/ml selenous acid, 5.33 µg/ml linoleic acid, and 1.25 mg/ml bovine serum albumin). Aliquots of 250,000 cells were suspended in 0.5 ml of chondrogenic medium and distributed to 15-ml conical polypropylene centrifuge tubes (Costar). The cells were centrifuged for 5 min at 600 g and left at the bottom of the tube. Tubes were incubated, with caps loosened, in a 100% humidified atmosphere of 95% air, 5% $CO_2$, at 37° C. for up to four weeks. The medium was changed twice a week.

Adipogenic Differentiation: For adipogenic differentiation (modified from DiGirolamo et al., *Br. J. Haematol.*, 107:275-281, 1999), cells were plated at 10,000 cells/cm$^2$ in 6-well plates in the presence of α-MEM/10% FBS/10% horse serum with 100 U/ml penicillin, 1 mg/ml streptomycin, 0.5 µM hydrocortisone, 0.5 mM isobutylmethylxanthine (Sigma), and 60 µM indomethacine (Sigma). Cells were incubated for three weeks in a 100% humidified atmosphere of 95% air, 5% $CO_2$, at 37° C. The medium was changed twice a week.

Neural Differentiation: For neural induction cells were plated at low density on 6-well-plates containing fibronectin (10 ng/ml-coated coverslips) in DMEM-HG/20% FBS with 100 U/ml penicillin and 1 mg/ml streptomycin for 24 hours. Neural specification (step 1) was induced by exposing cells to DMEM-HG/20% FBS/10 ng/ml bFGF for 24 hours. At the end of the neural specification treatment cells were washed thrice with PBS, and then neuronal commitment (step 2) was induced by exposing the cells to DMEM-HG supplemented with 1 mM β-mercaptoethanol (βME) and 10 ng/ml NT-3 for 2 days. Finally, neural differentiation (step 3) was induced by first washing thrice with PBS and then exposing the cells to NT-3 (10 ng/ml), NGF (10 ng/ml), and BDNF (50 ng/ml) in DMEM-HG for 3 to 7 days.

Endodermal Differentiation: To induce differentiation to pancreatic islet-like cells, cells were treated according to a sequential protocol of specification, commitment, and differentiation with factors known to promote the expression of a β-like-cell phenotype in other systems (Movassat et al., *J. Clin. Endocrinol. Metab.*, 87:4775-4781, 2002; Hunziker and Stein, *Biochem. Biophys. Res. Commun.*, 271:116-119, 2000; Zulewski et al., *Diabetes*, 50:521-533, 2001; Lumelsky et al., *Science*, 292:1389-1394, 2001). Briefly, cells were plated at a density of 10,000 cells/cm$^2$ in the presence of DMEM-HG, 20% FBS, for 24 hours. On the next day medium containing DMEM-HG, 20% FBS, and 10 ng/ml b-FGF was added for 24 hours. Endodermal specification was induced by exposure to medium containing DMEM-HG, 1% DMSO, and 100 µM butylated hydroxyanisole (BHA), 10 nmol/l exendin-4, for 24 hours. Cells were washed thrice, and endodermal commitment was induced by exposure to medium containing RPMI (GIBCO), 11.1 mmol/l glucose, 10% FBS, 10 mmol/l HEPES, 1.0 mmol/l Na-pyruvate, 20 ng/ml b-FGF, and 20 ng/ml EGF, 10 mmol/l exendin-4, for 4 days. Islet-like differentiation was induced by exposing the cells to medium composed of RPMI, 2.5 mmol/l glucose, 10 mmol/l HEPES, 10 mmol/l nicotinamide, 100 pmol/l HGF, 10 nmol/l exendin-4, and 2.0 nmol/l activin-A for 5-7 days.

f. RNA Isolation and Analysis

For RNA isolation, cells were grown in 60-mm dishes (Costar). At the indicated time points, the medium was removed, total RNA was extracted, and RT and amplification were performed as previously described (Schiller et al., *Bone*, 28:38-44, 2001; Schiller et al., *Bone*, 28:362-369, 2001). Total RNA was extracted using Trizol reagent (Gibco-BRL) according to manufacturer's instructions. RNA was quantified spectrophotometrically.

For reverse transcription-polymerase chain reaction (RT-PCR) analysis, total RNA was treated with RQ1 RNase-free DNase (Promega, Madison, Wis.), and RNA was precipitated in a 2-mol/l LiCl (Sigma) solution. Five micrograms of high-molecular-weight RNA was reverse transcribed using MuLV reverse transcriptase, 200 pmol random hexamer primer, and 50 pmol of oligo(dT). Aliquots (4%) of the total cDNA were amplified in each PCR in 20 µL of reaction mixture containing 10 pmol of 5' and 3' primers in a standard PCR buffer supplemented with 0.5 µCi of [$^{32}$P]dCTP (10 µCi/L; NEN, Boston, Mass.). All PCR reagents were from Perkin-Elmer (Norwalk, Conn.). Amplifications were performed in a Gene-Amp 9600 thermal cycler (Perkin-Elmer) for 20-27 cycles (typically: 94° C./30 sec; 55° C./45 sec; 72° C./60 sec) after an initial denaturation at 94° C. every 2 min. PCR products in a 10-µL aliquot were size-separated by electrophoresis in precast 6% acrylamide/TBE gels (Bio-Rad, Hercules, Calif.). The products of the amplification reactions were visualized by electronic autoradiography using an InstantImager analyzer (Packard Instrument Co., Meriden, Conn.).

The following human-specific PCR primer sequences were used. The size of the amplification product produced by each primer pair is shown in parentheses.

telomerase reverse transcriptase (Accession No. NM_003219) (272-bp product)
hTERT-F 5'-AGCCAGTCTCACCTTCAACCGC-3' (SEQ ID NO: 1) and
hTERT-R 5'-GGAGTAGCAGAGGGAGGCCG-3' (SEQ ID NO: 2);

elongation factor 1-alpha (Accession No. L41490) (235-bp product)
hEF1α-F 5'-AGGTGATTATCCTGAACCATCC-3' (SEQ ID NO: 3) and
hEF1α-R 5'-AAAGGTGGATAGTCTGAGAAGC-3' (SEQ ID NO: 4);

osteocalcin (Accession No. NM_000711) (315-bp product)
hOC-F 5'-CATGAGAGCCCTCACA-3' (SEQ ID NO: 5) and
hOC-R 5'-AGAGCGACACCCTAGAC-3' (SEQ ID NO: 6);

bone sialoprotein (Accession No. J05213) (667-bp product)
hBSP-F 5'-TCAGCATTTTGGGAATGGCC-3' (SEQ ID NO: 7) and
hBSP-R 5'-GAGGTTGTTGTCTTCGAGGT-3' (SEQ ID NO: 8);

osteopontin (Accession No. X13694) (348-bp product)
hOP-F 5'-CCAAGTAAGTCCAAVGAAAG-3' (SEQ ID NO: 9) and
hOP-R 5'-GGTGATGTCCTCGTCTGTA-3' (SEQ ID NO: 10);

runt domain transcription factor Runx2 (Accession No. L40992) (318-bp product)
hRunx2-F 5'-GTTTGTTCTCTGACCGCCTC-3' (SEQ ID NO: 11) and
hRunx2-R 5'-CCAGTTCTGAAGCACCTGA-3' (SEQ ID NO: 12);

collagen type II-alpha 1 (Accession No. NM_001844) (517-bp product)
hCOL2A1-F 5'-AACCAGATTGAGAGCATCCGC-3' (SEQ ID NO: 13) and
hCOL2A1-R 5'-CCTTCAGGGCAGTGTACGTGA-3' (SEQ ID NO: 14);

peroxisome proliferator-activated receptor gamma-2 (Accession No. U79012) (419-bp product)
hPPAR-γ2-F 5'-ATTCTCCTATTGACCCAGAAAGCG-3' (SEQ ID NO: 15) and
hPPAR-γ2-R 5'-AGCTTTATCTCCACAGACACGA-CATT-3' (SEQ ID NO: 16);

lipoprotein lipase (Accession No. X14390) (276-bp product)
hLPL-F 5'-GAGATCTCTGTATGGCACC-3' (SEQ ID NO: 17) and
hLPL-R 5'-CTGCAAATGAGACACTTTCTC-3' (SEQ ID NO: 18);

islet-1 transcription factor (ISL-1) (Accession No. BC017027) (542-bp product)
hISL-1-F 5'-CAACAAACAAAACGCAAAAC-3' (SEQ ID NO: 19) and
hISL-1-R 5'-AAGTCAAACACAATCCCGA-3' (SEQ ID NO: 20);

NK6 transcription factor related, locus 1 (Accession No. NM_006168) (239-bp product)
hNkx6.1-F 5'-CTGGAGAAGACTTTCGAACAA-3' (SEQ ID NO: 21) and
hNkx6.1-R 5'-AGAGGCTTATRGTAGTCGTCG-3' (SEQ ID NO: 22);

beta-cell transcription factor Beta2/NeuroD (Accession No. NM_002500) (295-bp product)
hBeta2-F 5'-TCTTTCAAACACGAACCGT-3' (SEQ ID NO: 23) and
hBeta2-R 5'-GCCTTTTGTAAACACGACAGT-3' (SEQ ID NO: 24);

glucagon (Accession No. NM002054) (170-bp product)
hGLUC-F 5'-ATCTGGACTCCAGGCGTGCC-3' (SEQ ID NO: 25) and
hGLUC-R 5'-AGCAATGAATTCCTTRGGCAG-3' (SEQ ID NO: 26); and insulin (Accession No. NM_000207) (94-bp product)
hINS-F 5'-AGGCTTCTTCTACACA-3' (SEQ ID NO: 27) and
hINS-R 5'-CAGGCTGCCTGCACCA-3' (SEQ ID NO: 28).

POU domain, class 5, transcription factor 1 (POU5F1/Oct-4) (Accession No. NM_002701) (577-bp product)
hOct-4-F 5'-CGACCATCTGCCGCTTTGAG-3' (SEQ ID NO: 29)
hOct-4-R 5'-CCCCCTGTCCCCCATTCCTA-3' (SEQ ID NO: 30)

Rex-1 (Accession No. AF450454) (306 bp product)
hRex1-F 5'-CAGATCCTAAACAGCTCGCAGAAT-3' (SEQ ID NO: 31)
hRex1-R 5'-GCGTACGCAAATTAAAGTCCAGA-3' (SEQ ID NO: 32)

g. Western Blot Analysis

Immunoblots were performed as previously described (D'Ippolito et al., *Bone,* 31:269-275, 2002). Briefly, total cell extracts were prepared using NP-40 lysis buffer (50 mmol/L Tris, pH 8.0, 1.0% NP-40, 150 mmol/L NaCl, 2 mmol/L ethylene-glycol tetraacetic acid [EGTA], 2 mmol/L ethylene-diamine tetraacetic acid [EDTA], protease inhibitor tablet [Roche Molecular Biochemicals, Indianapolis, Ind.], 50 mmol/L sodium fluoride, and 0.1 mmol/L sodium vanadate), and protein concentrations were determined using a protein assay (Bio-Rad Laboratories, Hercules, Calif.). After separation of 10 µg protein by sodium dodecylsulfate-polyacrylamide gel electrophoresis (SDS-PAGE), proteins were transferred by electrophoresis to an Immobilon-P membrane (Millipore Corp., Bedford, Mass.) and incubated in 5% nonfat dry milk, phosphate-buffered saline (PBS), and 0.25% Tween-20 for 1 hour. Antibodies were diluted in 5% nonfat dry milk, PBS, and 0.25% Tween-20 and incubated overnight at 4° C. Membranes were washed in PBS and 0.25% Tween-20 (three times, 10 min each time) and incubated with horseradish peroxidase-conjugated secondary antibody (antirabbit; 1/2000 dilution; Santa Cruz Biotechnology) for 1 hour, washed in PBS and 0.25% Tween-20, and analyzed by exposure to X-ray film (X-Omat, Eastman Kodak Co., Rochester, N.Y.) using enhanced chemiluminescence plus (ECL Plus, Amersham Pharmacia Biotech, Arlington Heights, Ill.). Membranes were subsequently washed for 1 hour in PBS and 0.25% Tween-20, and actin protein was measured using goat-polyclonal antibodies (1/1000 dilution; C-11, Santa Cruz Biotechnology) and antigoat horseradish peroxidase-conjugated secondary antibody (Santa Cruz Biotechnology).

h. Immunofluorescence

For staining of cytoskeletal proteins, cells were fixed with methanol at −20° C. for 2 min and permeabilized with 0.1% Triton X-100 for 10 min. For staining of other intracellular molecules, cells were fixed with 4% paraformaldehyde at 4° C. for 10 min and permeabilized with 0.1% Triton X-100 for 10 min. For staining of cell surface receptors, cells were fixed with 4% paraformaldehyde at 4° C. for 10 min. Blocking and diluent solution consisted of phosphate-buffered saline (PBS), 1% BSA, and 1% serum (Sigma) from a species similar to the species in which the secondary antibody was raised. Slides were blocked for 30 min, incubated sequentially for 30 min each with secondary specific antibodies, followed by incubation with fluorescein- or rhodamine-conjugated anti-mouse or antirabbit IgG antibody. Between each step, slides were washed with PBS plus 0.3% BSA. Specific immunostaining was demonstrated in control experiments in which cells were exposed to primary isotypic antibodies and then incubated with conjugated antibodies.

i. Flow Cytometry Analysis

Undifferentiated MIAMI cells grown from single-cell-derived colonies were plated in triplicate on 60-mm dishes in the presence of expansion medium. Five days later the cells were trypsinized, and 1×10$^6$ cells were aliquoted into FACS tubes (BD Bioscience). Cells were rinsed twice with a cold buffer solution (DPBS, 0.5% BSA, 0.02% sodium azide, at pH 7.4) and then stained with the specific conjugated primary antibody. Cells were rinsed again twice with the cold buffer solution and fixed with 1% paraformaldehyde until analysis with FACScan (BD Bioscience).

j. Cell Proliferation Assay

Cells were plated in quadruplicate on 96-well plates in 200 μL of expansion medium. At the end of each assay day, cells were rinsed with PBS and then fixed with 70% cold (4° C.) ethanol for 1 hour. Thereafter, cells were stained with 0.1% crystal violet (w/v) for 30 min at room temperature and rinsed with distilled water to remove the nonspecific stain; then 200 μL of 1% Triton (v/v) was added to each well to dissolve the crystal violet bound to the cell nuclei. Plates were incubated overnight at room temperature in an orbital shaker, and absorbance was read at 620 nm on an EAR 400-AT (SLT Instruments, Austria) microplate reader. Absorbance values were transformed into absolute cell numbers using a standard curve.

k. Alkaline Phosphatase Activity

Cells were plated on 96-well plates in the presence of differentiation medium Alkaline phosphatase activity was measured in quadruplicate as previously described (Schiller et al., Bone, 28:362-369, 2001). Briefly, cells were rinsed twice with PBS, and then 200 μL of 1 mg/mL p-nitrophenylphosphate (Sigma) in 0.1 mol/L glycine buffer (pH 10.5) was added to each well. Plates were incubated at 37° C. for 10 min Enzyme activity, expressed as nanomoles of p-nitrophenol produced per minute normalized to cell number, was measured with a microplate reader at 405 nm.

l. Calcium Accumulation Assay

In vitro mineralization was evaluated on 6-well plates at the end of day 21, as previously described (Schiller et al., Bone, 28:362-369, 2001; D'Ippolito et al., Bone, 31:269-275, 2002). Briefly, cells were rinsed three times with PBS at room temperature, fixed with ice-cold 70% ethanol for 1 hour at 4° C., rinsed three times with distilled water, and then stained with 40 mmol/L Alizarin red sulfate (AR-S, Sigma), pH 4.2, for 10 min at room temperature using an orbital shaker (100 rpm). Nonspecifically bound stain was subsequently removed using five brief rinses with distilled water and one rinse for 15 min with PBS at room temperature. Extracellular matrix (ECM) mineral-bound stained nodules were photographed using inverted light microscopy. ECM mineral-bound AR-S was quantified by spectrophotometric evaluation at 562 nm (using an AR-S standard curve) after solubilizing the stain by a 15-min incubation (orbital shaker) in 1 mL of 10% cetylpyridinium chloride in 10 mmol/L sodium phosphate, pH 7.0.

m. Sudan-IV Staining

For Sudan-IV staining of cytoplasmic triglyceride lipid droplets, cells were fixed with 10% formalin at −20° C. for 2 min and rinsed in water. Slides were stained in Sudan-IV (Sigma) for 10 min and rinsed in water (Schiller et al., J. Biol. Chem., 276:14133-14138, 2001).

2. Isolation and Expansion of MIAMI Cells

Isolation of MIAMI-cell colonies was 100% more efficient when unfractionated cells, which were not subjected to density gradient centrifugation or immunodepletion, were used (FIG. 1A). Cell selection was based on the capacity of the cells to proliferate under specific conditions of low oxygen tension, ECM substrate, plating density, and co-culture with nonadherent cells. These unique isolation and culture conditions result in the selection/expansion of a population of cells with less cytoplasm (see FIG. 1B).

Figure 2:
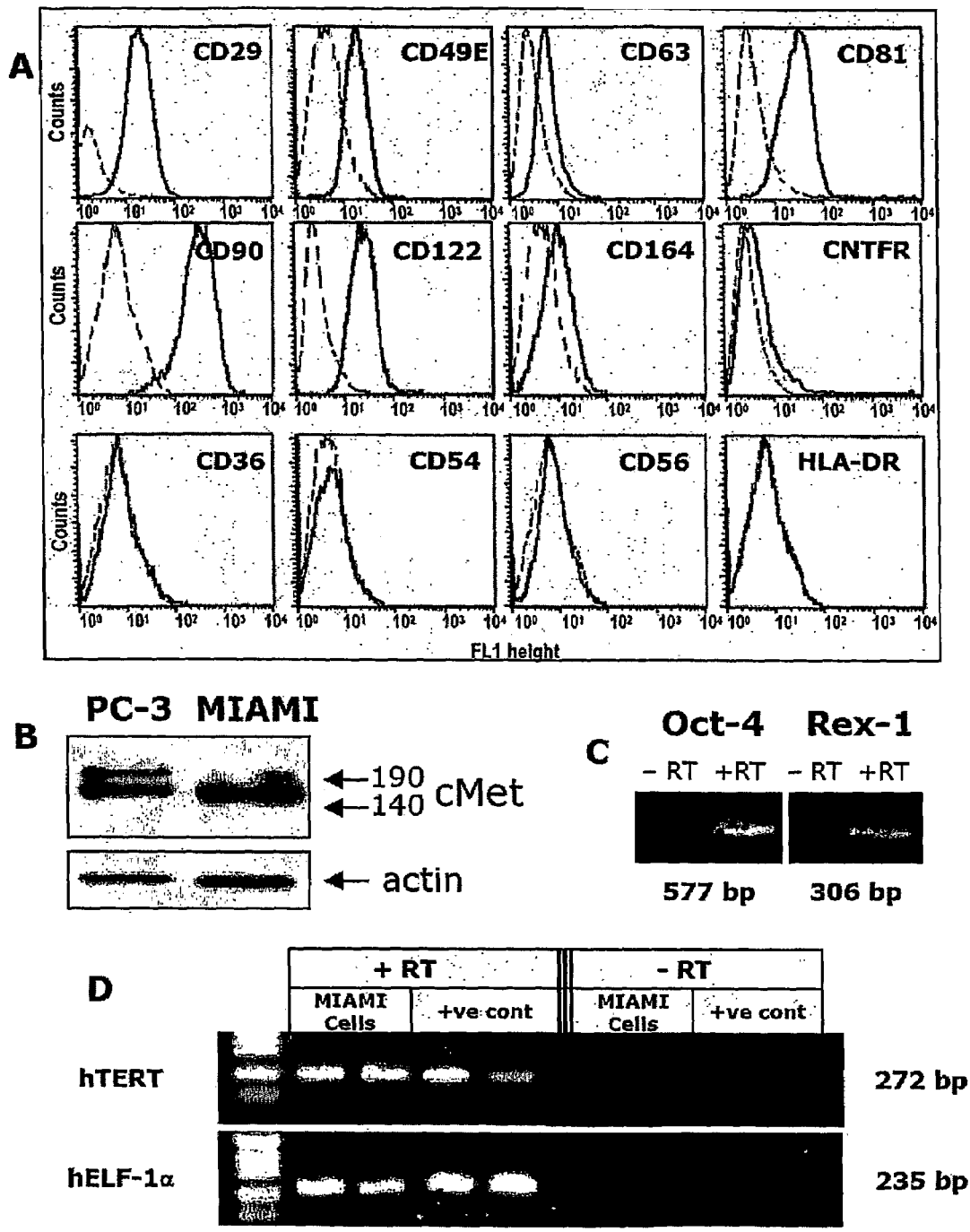
FIG. 2 shows the results of experiments characterizing the expression of various markers in MIAMI cells.

Single-cell-derived colonies were molecularly defined by expression of the following combination of markers: CD29, CD49e, CD63, CD81, CD90, CD122, CD164, and CNTFR (FIG. 2A); they were also positive for cMet (FIG. 2B), NTRK3, and BMP-receptor 1B. In addition, these cells were negative for CD36, ICAM-1 (CD54), N-CAM (CD56), CD 109, and HLA-DR (FIG. 2A). They were also negative for CD34, CD45, CD117 (cKit), and Class I-HLA. Telomerase (hTERT) was expressed in all cultures examined (FIG. 2C). Expression of this marker combination, unique to the disclosed cells, is consistently found in all samples, regardless of donor age and gender. After culture expansion, undifferentiated MIAMI cells remained negative for CD34, CD45, HLA-DR, expressed low levels of Flt-1, and Flk-1/KDR and were positive for CD10, CD44, and CD103 in addition to the markers described above. The expanded MIAMI subpopulation of hMSCs remained morphologically unchanged (FIG. 1D). MIAMI cells also consistently expressed markers found in mesodermal, endodermal, and ectodermal lineages in samples taken from all ages, as summarized in the compilation of RT-PCR, northern blot, immunocytochemistry, immunoblot, and flow cytometry data shown in Table 7.

TABLE 7

Ectodermal, Endodermal, And Mesodermal
Gene Products in MIAMI Cells*

| Ectoderm | Endoderm | Mesoderm |
| --- | --- | --- |
| Neurotrophic tyrosine kinase, receptor, type 3 | Hepatocyte growth factor (HGF) | Decorin<br>Cadherin 11 |
| Ciliary neurotrophic factor receptor | C-met (HGF receptor) | CD81/TAPA1<br>Runx2 |
| BMP receptor, type IB | ISL-1 (Islet-1) transcription factor | Osteopontin<br>CD63 |
| Neuron specific enolase | Beta-2 transcription factor | CD164 |
| POU4F1 transcription factor | Nkx6.1 transcription factor | |

*Cells were derived from males and females 3 to 72 years old.

Figure 3:
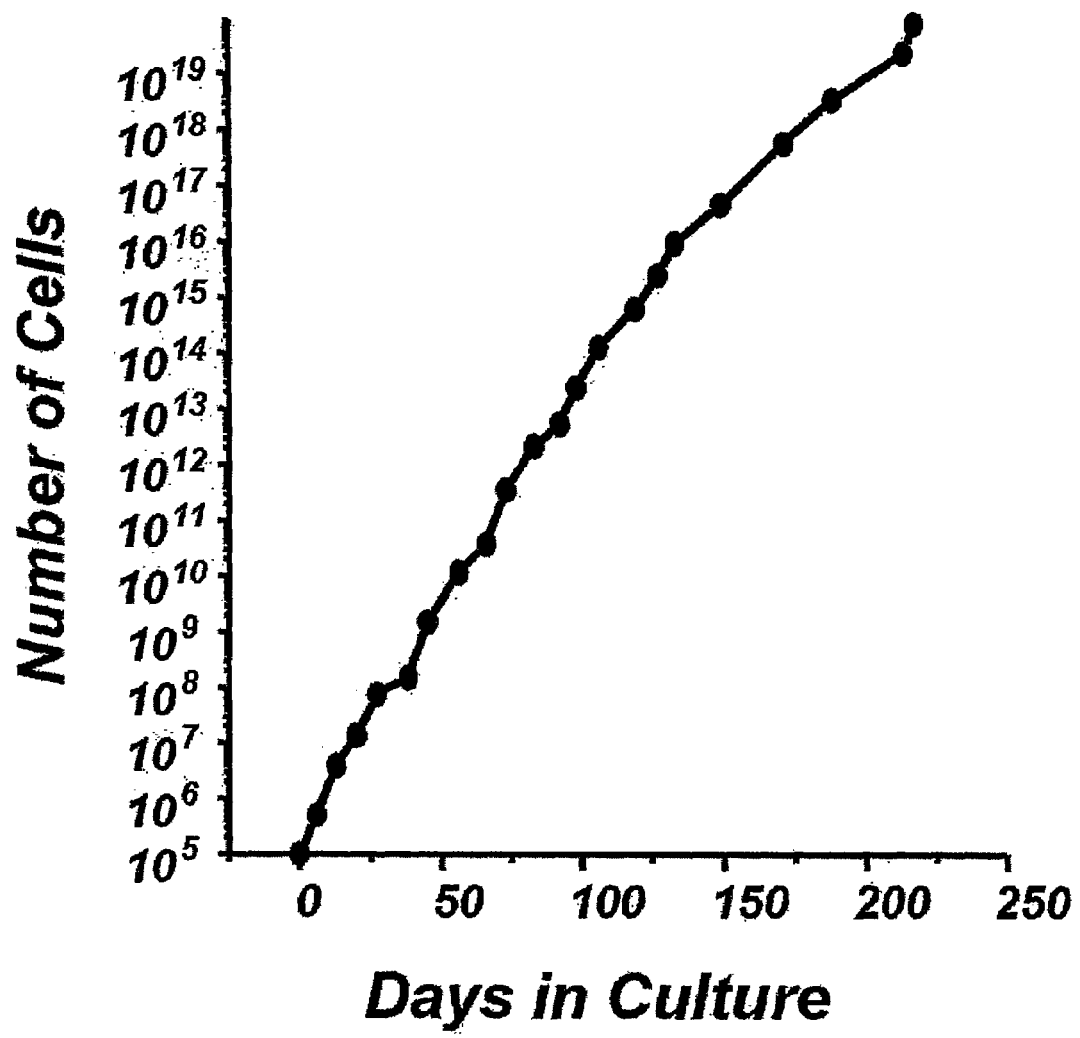
FIG. 3 shows a graph of MIAMI cell number versus days in culture. More than 50 cell doublings without detectable differentiation could be obtained in cultures grown in medium containing low serum (2%) supplemented with 15% conditioned medium (2% serum). Cells cultured for a few passages or cells expanded in excess of 50 population doublings remained small, with reduced cytoplasm, and differentiated into osteoblastic and neural phenotypes. Cells were counted at each passage with a hemacytometer.

MIAMI cell cultures from all 12 donors, ages 3 to 72 years are capable of proliferating beyond 30 cell doublings and of differentiating to numerous cell types (see below). MIAMI cells have been expanded more than 50 cell doublings, beyond the Hayflick limit for primary cells (Hayflick and Moorhead *Exp. Cell. Res.,* 25:585-621, 1961), in at least 3 donors (#519 [3-year-old boy], #849 [7-year-old boy], and #869 [55-year-old man]). These results support the stem-like properties of the MIAMI cells. When MIAMI cells were cultured at low density (≦30% confluency) in expansion medium containing low serum (2%), cell doubling time increased to more than 60 hours. In cultures in which the low-serum medium was supplemented with 15% conditioned medium (from expanded MIAMI cell), cells could be expanded for more than 50 population doublings. As was seen for cells cultured for a low number of passages, cells expanded in excess of 50 population doublings remained small with reduced cytoplasm (FIG. 1D); no morphological changes could be detected. Expanded cells differentiated into osteoblastic and neural phenotypes (see below). A typical graph of the expansion potential profile of MIAMI cells is shown in FIG. 3. Several MIAMI cells isolated from donors of different ages (#869 [55-year-old man], #812 [72-year-old man], and #889 [59-year-old woman]) have responded identically to long-term expansion whether the cells were used immediately after isolation or after cryopreservation for periods of time ranging from 2-12 months.

3. Multilineage Potential of MIAMI Cells In Vitro

Single-cell-derived colonies as well as multicolony-derived MIAMI cells isolated from donor #849, a 7-year-old boy, can be expanded ex vivo and induced to differentiate to bone-forming osteoblasts, cartilage-forming chondrocytes, and fat-forming adipocytes as well as to neural cells (ectoderm-derived lineage) and pancreatic β-like cells (endoderm-derived lineage).

a. Osteogenic Differentiation

Cells with bone-forming capacity showed high alkaline phosphatase activity, produced and mineralized an extracellular matrix, and made bone nodules in vitro (see FIG. 3A). In addition, these cells expressed the osteoblast gene markers Runx2, osteocalcin, collagen I α1, and bone sialoprotein (FIG. 3B).

b. Chondrogenic Differentiation.

For chondrogenic differentiation, cells were incubated in tubes containing the micromass cultures, with caps loosened, in a 100% humidified atmosphere of 95% air, 5% $CO_2$ at 37° C. for various periods of time. Sedimented cells formed a spherical mass at the bottom of the tube within 24 hours. Medium was replaced three times a week. Virtually all of the cells showed cartilaginous tissue-forming capacity and produced a proteoglycan-rich soft collagen matrix. The cells expressed the chondrocyte gene marker collagen II protein and mRNA.

c. Adipogenic Differentiation.

Figure 4:
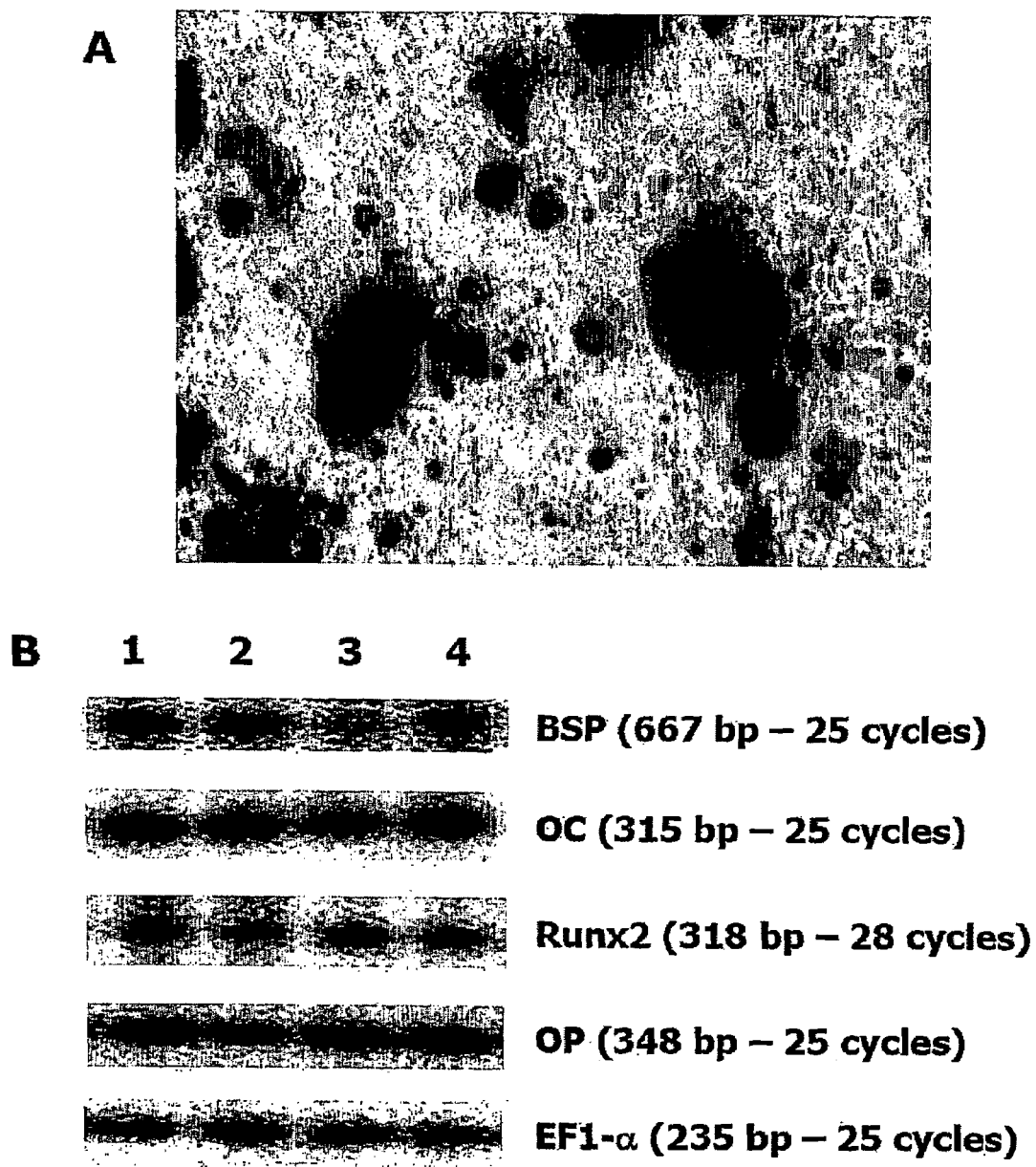
FIG. 4 shows the result of experiments characterizing osteoblastic induction of MIAMI cells.
Figure 5:
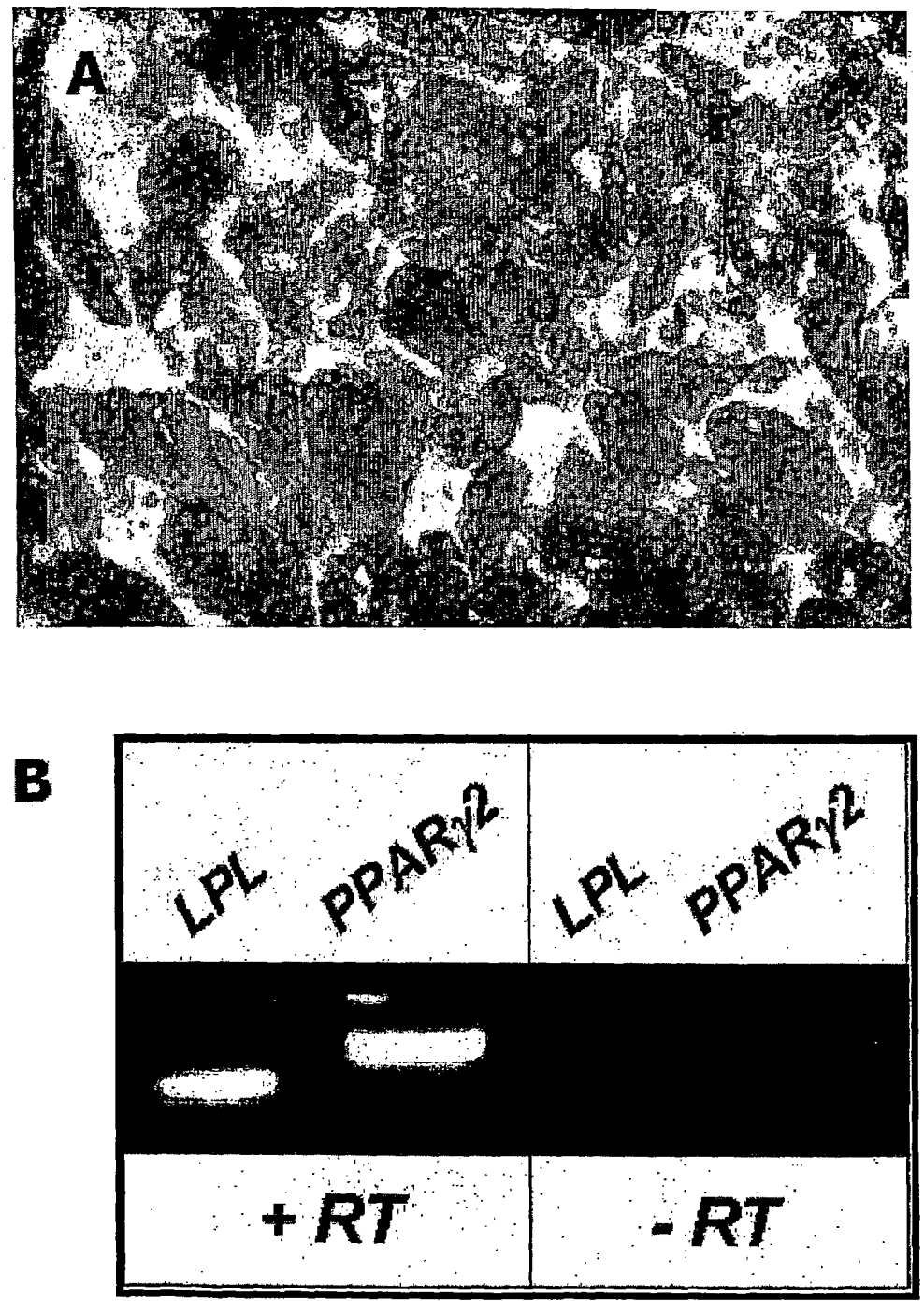
FIG. 5 shows the result of experiments characterizing adipogenic induction of MIAMI cells.

For adipogenic differentiation cells were plated in 6-well plates and incubated for three weeks in a 100% humidified atmosphere of 95% air, 5% $CO_2$ at 37° C. At the end of three weeks incubation, cells were washed thrice with PBS at room temperature, fixed with ice-cold 10% formalin buffer, and stained with fresh Sudan-IV solution. Plates were rinsed briefly with water. Nearly all the cells showed adipose tissue-forming capacity and accumulated large amounts of triglycerides in their cytoplasm (FIG. 4A). The cells expressed the adipocyte gene markers lipoprotein lipase and the pro-adipocytic transcription factor peroxisome proliferators-activated receptor γ-2 (FIG. 4B).

d. Neural Differentiation.

Figure 6:
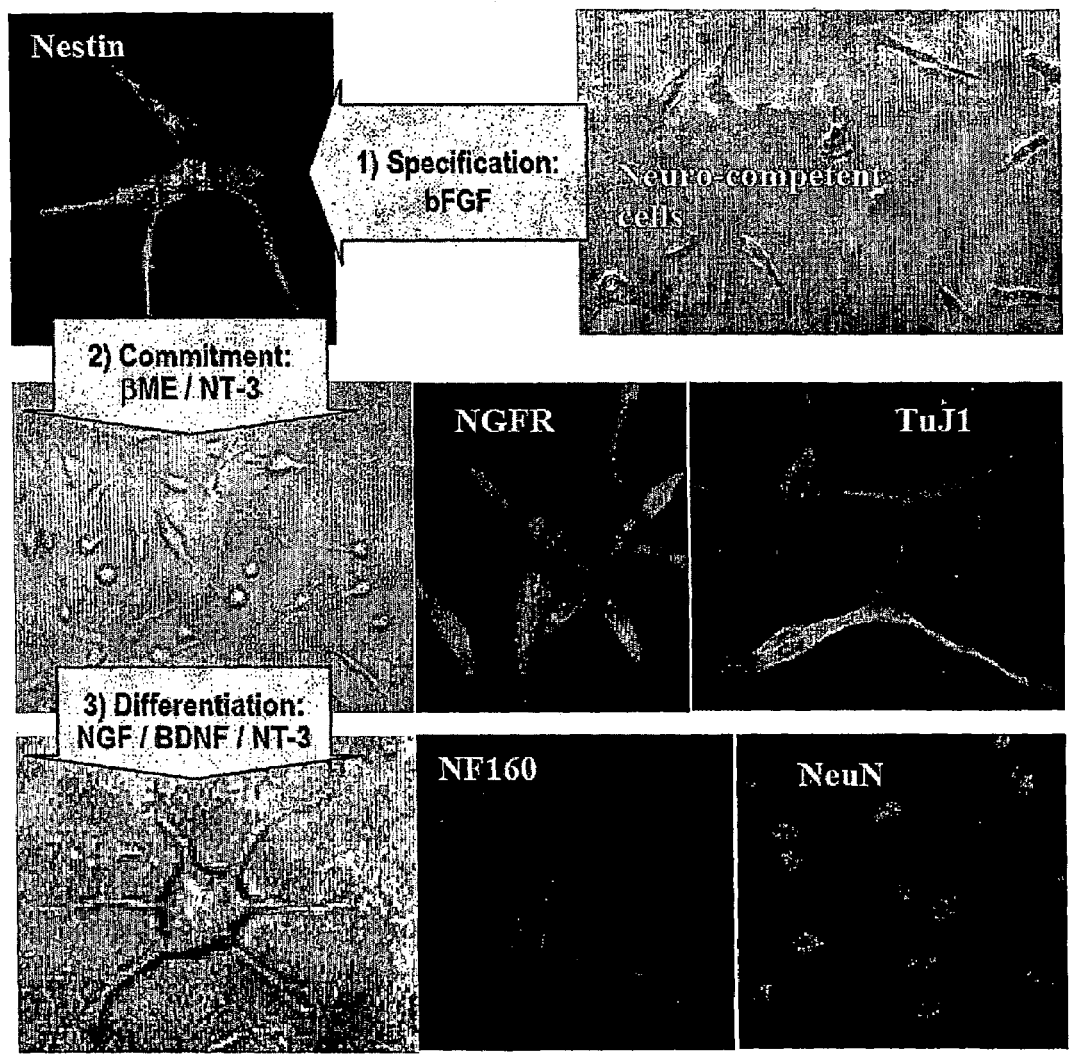
FIG. 6 shows digital photographs demonstrating neural induction of MIAMI cells.

For neural induction MIAMI cells (FIG. 6) were plated on 6-well-plates. The next day a neural preinduction was performed for 24 hours. After 24 hours the cells were washed thrice with PBS, and neural specification medium (DMEM-HG/bFGF) was added for 24 hours. Some of the cells acquired the bipolar spindle shape characteristic of neural cells within 2 hours. At this stage, cells expressed nestin (FIG. 6, top left) and GFAP, but were negative for neuron-specific class III β-tubulin (TuJ1), neurofilament 160 (NF160), and neuronal nuclear protein (NeuN). After the neural specification treatment, cells were washed thrice with PBS and neuronal commitment (step 2) was induced for 2 days. At this stage a morphologically homogeneous neural-like cell population was observed as a result of each neuronal commitment step (FIG. 6, middle). Expression of neuron-specific class III β-tubulin (TuJ1) and NGF receptor was detected in a fraction (40-50%) of these cells (FIG. 6, middle). Neural differentiation (step 3) was then induced by exposing the cells to NT-3, NGF, and BDNF for 3 to 7 days. At this stage, cells expressed NeuN and neurofilament-160 (FIG. 6, bottom), while expression of nestin was not detected, consistent with a mature neural phenotype. Specific immunostaining was demonstrated in experiments in which no staining was detected when primary isotypic antibodies were used as negative controls and fetal brain-derived human neuroepithelial progenitor cells (McCarthy et al., *J. Hum. Virol.,* 3:215-228, 2000) were used as positive controls.

The morphology of the neural-induced MIAMI cells closely resembled that of mature neurons, exhibiting a large number of neurites with significant branching (FIG. 6, bottom left). Moreover, the electrophysiological properties of the neural-like cells obtained after the final differentiation step were undistinguishable from properties of mature neurons (as described in more detail in Example 2). None of the mature neural markers was detected in the expanded MIAMI cells before their in vitro neural differentiation induction.

Several MIAMI cells isolated from donors of various ages (#519 [3-year-old boy], #869 [55-year-old man], #812 [72-year-old man], and #889 [59-year-old woman]), responded in a similar fashion. Ten single-cell-derived colonies from MIAMI cells derived from sample #519 (3-year-old boy) were expanded under conditions described and tested for their ability to differentiate toward the ectodermal-derived neural lineage. These cells responded to differentiation in a manner similar to that described above. Characterization to other ectodermal-derived lineages is ongoing.

e. Differentiation of MIAMI Cells to Insulin-Expressing Structures Similar to Pancreatic Islets.

Data showing that MIAMI cells express markers associated with an endodermal lineage together with knowledge that precursors of pancreatic β-cells and neural cells share common factors associated with their development and differentiation prompted an investigation of the possibility of promoting the expression of genes associated with the phenotype of β-cells in MIAMI cells.

Cells were treated with factors known to promote the expression of a β-like-cell phenotype in other systems (Movassat et al., *J. Clin. Endocrinol. Metab.,* 87:4775-4781, 2002; Hunziker and Stein, *Biochem. Biophys. Res. Commun.,* 271:116-119, 2000; Zulewski et al., *Diabetes,* 50:521-533, 2001; Lumelsky et al., *Science,* 292:1389-1394, 2001). Culture conditions were developed (see above) in which cells proliferated, from attached cells, in an attachment-independent fashion, forming structures that acquired the shape of spherical clusters similar to embryonic stem cell-derived insulin-secreting structures (FIGS. 7 A and B). This process was effective with the sequential treatment of the cells first with bFGF followed by exendin-4 (an agonist for glucagon-like peptide 1 receptor [GLP1R]).

Portions of the treated and untreated cells were used for total RNA isolation and the expression of transcripts encoding for insulin and glucagon (two hormones associated with the phenotype of pancreatic islets) and for Beta2/NeuroD, Nkx6.1, and Isl1 (transcription factors involved in β-cell development). The RNAs were analyzed by RT-PCR using human specific primers. FIG. 7C (bottom) shows the detection of specific bands corresponding to the β-cell-associated transcription factors Beta2/NeuroD, Nkx6.1, and Isl1, in both treated and control cells. The addition of forskolin to augment protein kinase A-mediated signaling did not increase the level of expression of these transcripts. However, transcripts for insulin and glucagon were observed only after sequential treatment with bFGF, followed by exendin-4 and then HGF/exendin-4/activin A (FIG. 7C, top). RNA from human pancreatic islet cells was used as a positive control.

4. Novel Features of Cells and Methods of their Isolation and Expansion

Based on molecular profile and differentiation potential, this example describes the isolation of novel and distinctive populations of multipotent cells from human bone marrow. The methods described in this example utilize unfractionated whole bone marrow and a unique expansion/selection procedures that involve a combination of culture conditions, including for example, ECM substrate, oxygen tension, growth factors and vitamins, cell density, and/or co-culture of cells, designed to resemble an in vivo niche microenvironment in which more primitive cells are expected to thrive (Watt and Hogan, Science, 287:1427-1430, 2000). Via this process bone marrow cells with broad differentiation potential, expressing markers found among mesodermal-, endodermal-, and ectodermal-derived lineages were isolated.

In this example, adherent cells are co-cultured with nonadherent cells for 14 days. Nonadherent cells are thought to provide the cytokines needed for maintenance and proliferation of the more primitive stromal cells. The nonadherent cells are removed only after single-cell-derived colonies are established. The selection/expansion protocol is then continued with the adherent cells.

This selection/expansion culture protocol is performed under hypoxic conditions (3-5% [23.4-39 mmHg] oxygen), with the rationale of providing the conditions that resemble an in vivo niche housing the most primitive stem cells (Chow et al., Biophys. J., 81:675-684, 2001; Cipolleschi et al., Blood, 82:2031-2037, 1993; Lord, In: Concise Reviews in Clinical and Experimental Haematology (ed, Murphy, M., Jr.), Dayton, Ohio: AlphaMed Press, 1992). In comparison, the standard approaches use air (21% [159 mmHg] oxygen) for expansion/selection of bone marrow progenitor cells (Friedenstein et al., Cell Tissue Kinet., 3:393-403, 1970; Ferrari et al., Science, 279:1528-1530, 1998; Young et al., J. Orthop. Res., 16:406-413, 1998; Conget and Minguell, J. Cell. Physiol., 181:67-73, 1999; Kopen et al., Proc. Natl. Acad. Sci USA, 96:10711-10716, 1999; Pittenger et al., Science, 284:143-147, 1999; Asahara et al., EMBO J., 18:3964-3972, 1999; Theise et al., Hepatology, 31:235-240, 2000; Brazelton et al., Science, 290:1775-1779, 2000; Krause et al., Cell, 105:369-377, 2001; Orlic et al., Proc. Natl. Acad. Sci. USA, 98:10344-10349, 2001; Mezey et al., Proc. Natl. Acad. Sci. USA, 100:1364-1369, 2003).

The MIAMI cell population isolated using the methods described in this example is morphologically homogeneous and expresses a unique set of surface markers distinguishing MIAMI cells from those reported to be expressed in other primitive bone marrow stromal cell populations, such as RS-1 (Colter et al., Proc. Natl. Acad. Sci. USA, 97:3213-3218, 2000; Colter et al., Proc. Natl. Acad. Sci. USA, 98:7841-7845, 2001) and/or MAPCs (Reyes et al., Blood, 98:2615-2625, 2001; Jiang et al., Nature, 418:41-49, 2002). Some of these distinctions are shown in Table 8. For example, while MAPCs were reported positive for CD13, CD49b, and to a lesser extent, CD133 (Reyes et al., Blood, 98:2615-2625, 2001; Jiang et al., Nature, 418:41-49, 2002), expression of these markers was not detected in MIAMI cells. On the contrary, CD10 (a neutral endopeptidase in B-cell progenitors and germinal center cells) was detected in MIAMI cells but not in MAPCs or RS-1 cells. While RS-1 cells express CD36 and CD71 (Colter et al., Proc. Natl. Acad. Sci. USA, 97:3213-3218, 2000; Colter et al., Proc. Natl. Acad. Sci. USA, 98:7841-7845, 2001), these markers were not detected in MIAMI cells. Expression of CD71 has also been reported for mesenchymal stem cells (Pittenger et al., Science, 284:143-147, 1999). MIAMI cells also express CD164, a sialomucin-like molecule found on early hematopoietic progenitors, as well as molecules involved in signaling of various types of progenitor and mature cells including CD122 (IL-2Rβ), CD81 (TAPA-1 involved in cell growth and signal transduction), bone morphogenetic receptor 1B, and HGF receptor (c-Met).

TABLE 8

Comparison of Marker Expression among Selected Multipotent Cells

| Marker | MIAMI | MAPC[1] | MSC[2] | Reserve[3] | RS-1[4] |
| --- | --- | --- | --- | --- | --- |
| CD10 (CALLA) | ++ | − | | +++ | − |
| CD13 (Aminopeptidase N) | − | +++ | | +++ | |
| CD29 (Integrin β$_1$)* | +++ | | +++ | | |
| CD34 (Sialomucin) | − | − | − | | − |
| CD36 | − | − | | | + |
| CD44e (Hyaluronate) | + | ± | + | | |
| CD49b (Integrin α$_2$) | − | +++ | + | | |
| CD49d (Integrin α$_4$) | − | | − | | |
| CD49e (Integrin α$_5$)* | ++ | | − | | |
| CD71 (Transferrin R) | − | | ++ | | +++ |
| CD81 (TAPA-1)* | +++ | | | | ± |
| CD133 | − | ± | | | − |
| CD140a (PDGFR) | − | | ++ | | − |

[1]Reyes et al., Blood, 98: 2615-2625, 2001; Jiang et al, Nature, 418: 41-49, 2002
[2]Pittenger et al., Science, 284: 143-147, 1999
[3]Young et al, Proc. Soc. Exp. Biol Med., 221: 63-71, 1999; Young et al., Anat. Rec., 264: 51-62, 2001.
[4]Colter et al., Proc. Natl. Acad. Sci. USA, 97: 3213-3218, 2000; Colter et al., Proc. Natl. Acad. Sci. USA, 98: 7841-7845, 2001

MIAMI cells clearly express markers found among stem-like cells. Moreover, MIAMI cells are equipped to respond to signals leading to differentiation toward diverse lineages. Like hMSCs, RS-1, or MAP cells, MIAMI cells can be differentiated to cells that express markers unique to bone-forming osteoblasts, cartilage-forming chondrocytes, and fat-forming adipocytes and to cells with features of immature neural-like cells. MIAMI cells, unlike RS-1 and/or MAP cells, have been induced to differentiate into attachment-independent spherical clusters, which express markers associated with endodermal-derived lineages and are found among cells in pancreatic islets.

Single-cell-derived clonogenic colonies of MIAMI cells were able to differentiate toward cell lineages from at least two different embryonic germ layers. Specifically, mesodermal-derived osteoblastic cells and ectodermal-derived neural cells, with phenotypic and functional features of specialized mature cells, were obtained from MIAMI cells derived from single-cell-derived colonies. Such clonogenic colonies show extensive proliferative capacity and have been expanded in excess of 50 population doublings without detectable senescence or loss of differentiation potential.

While cell fusion of somatic to ES cells has been suggested as an explanation for stem cell plasticity (Terada et al., *Nature*, 416:542-545, 2002; Ying et al., *Nature*, 416:545-548, 2002), the in vitro studies described in this example demonstrate that single euploid MIAMI cells, never exposed to ES cells or other embryonic or mature somatic cells, differentiated into cells of two germ layers. Thus, the in vitro behavior of MIAMI cells cannot be attributed to cell fusion.

When MIAMI cells were cultured at high density (>10,000 cells/cm$^2$) and exposed to cytokines that induce their differentiation, the cells stopped proliferating and terminal differentiation was evident on both a molecular and functional basis. Long-term culture ($\geq$30 days) of differentiated cells led in many cases to apoptosis with no evidence of transformation.

Although mesodermal-derived lineages could be obtained using primary marrow stromal stem cells isolated by standard procedures for mesenchymal stem cell isolation (Pittenger et al., *Science*, 284:143-147, 1999), neural and endodermal differentiation could be obtained only with MIAMI cells. Treatment of marrow stromal stem cells or mesenchymal stem cells (isolated using standard published procedures) with the conditions used for the neural and endodermal differentiation of MIAMI cells did not cause endodermal or neural differentiation of hMSCs. Neural-like differentiation could be obtained using hMSCs, resulting in cells expressing some of the markers found in neurons. However, only differentiation of MIAMI cells produced neural cells with electrophysiological properties (resting membrane potential $\leq$70 mV and ionic channel activity) undistinguishable from those of mature neurons (see Example 2 for additional detail). In a similar fashion, only MIAMI cells (but not hMSCs) were able to synthesize transcripts for insulin in response to exendin-4 following the protocol described.

MIAMI cells were isolated from vertebral bodies of cadaveric donors, confirming cadaveric vertebral bodies as a useful source of material for the isolation of primitive bone marrow cells with extensive proliferative and differentiation potential. MIAMI cells also can be readily isolated from peripheral blood and iliac crest aspirates.

Example 2

Neural Differentiation of MIAMI Cells

This example demonstrates that human bone-marrow-derived MIAMI cells can de induced to differentiate to cells with biochemical, morphological and electrophysiological characteristics of mature neurons in response to defined cytokines without the need of co-culturing with any other cell types.

1. Materials and Methods a. Cytokines

Human recombinant basic-fibroblast growth factor (b-FGF) was from Sigma Chemical (St. Louis, Mo.); β-nerve growth factor (NGF), neurotrophin-3 (NT-3), and brain-derived neurotrophic factor (BDNF), were from Calbiochem (San Diego, Calif.).

b. Antibodies

The following primary antibodies were used for immunocytochemistry (dilution from 1:100-1:1000): neuron-specific enolase (NSE), neurofilament-L (68 kD), neurofilament-M (160 kD), nestin, neuronal nuclear protein (Neu-N), glial fibrillary acid protein (GFAP), and NGF receptor (TrkA) were obtained from Chemicon (Temecula, Calif.); neuron-specific class III β-tubulin (antibody referred to as TuJ1) was obtained from Covance (Princeton, N.J.); and NT-3 receptor (NTRK-3) was obtained from Santa Cruz Biotechnology (Santa Cruz, Calif.). Horseradish peroxidase (HRP), rhodamine, and FITC conjugated secondary antibodies were obtained from Santa Cruz Biotechnology (Santa Cruz, Calif.).

c. Bone Marrow and Cells

Whole bone marrow was obtained from vertebral bodies (T1-L5) of 12 cadaveric male and female donors who died of fatal traumatic injury (age range; 3-72 years old), following guidelines for informed consent set by the University of Miami School of Medicine Committee on the Use of Human Subjects in Research. Isolated whole bone marrow cells were plated at a constant density of $10^5$ cells/cm$^2$ in DMEM-low glucose media, containing 5% fetal bovine serum (FBS) and 100 U/ml penicillin/1000 U streptomycin in fibronectin (10 ng/mL)-coated 10-cm dishes as described in Example 1. Whole bone marrow cells, containing adherent and nonadherent cells, were maintained in a humidified incubator at 37° C. undisturbed in an atmosphere of 3% $O_2$/5% $CO_2$/92% $N_2$; 7 days later half of the culture medium was replaced. Fourteen days after the initial plating, the nonadherent cells were removed. Single-cell-derived (isolated using cloning rings) and pooled colonies of adherent cells were carefully rinsed in medium and subcloned. These cells were selected and expanded at low density ($\leq$30% confluency) by plating single-cell-derived or pooled colonies in fibronectin (10 ng/mL)-coated dishes using an expansion medium composed of: 98% DMEM-low glucose, 2% PBS, and 100 U/ml penicillin/1000 U streptomycin (Gibco-BRL) at 3% $O_2$/5% $CO_2$/92% $N_2$.

d. Human Fetal Neuroepithelial Precursors Cells

Human fetal neuroepithelial precursor cells or neurospheres were used as positive controls for the expression of the intermediate filament protein nestin that belongs to the early neural markers (Lendahl et al., *Cell*, 60:585-595, 1990; Cattaneo and McKay, *Nature*, 347:762-765, 1990). Pluripotent neuroepithelial stem cells were prepared from dissociated first trimester gestation fetal human CNS as described previously (Quinn et al., *J. Neurosci. Res.*, 57:590-602, 1999). Fetal CNS tissue specimens included telencephalon, diencephalon, and rostral brainstem. Procedures for procurement and use of this human fetal CNS tissue are approved and monitored by the University of Miami School of Medicine's Medical Sciences Subcommittee for the Protection of Human Subjects. Cells derived from distinct fetal specimens were cultured separately; there was no co-culturing of cells from different specimens. Single cell suspensions were cultured in defined medium supplemented with EGF and b-FGF (Neural Progenitor Maintenance Medium [NPMM] Bullet Kit, Clonetics Division of BioWhittaker, San Diego, Calif.) or Neurobasal medium plus B27 supplement (Brewer et al., *J. Neurosci. Res.*, 35:567-576, 1993) (Gibco Invitrogen Corp, Grand Island, N.Y.). These cultures generated proliferating clones of stem cells in floating spheres ("neurospheres"), which were cultured for 7-10 days. To initiate differentiation of stem cells, the spheres were seeded on an adherent substrate (poly-D, L-ornithine plus fibronectin-coated glass, PO/FBN) in medium supplemented with 2.5% (v/v) heatinactivated FBS. Proliferating and differentiating neuroepithelial precursor cells migrated out from adherent spheres so that a monolayer culture developed within 1 day post seeding.

e. Neural Induction

For neural induction, morphologically homogeneous single-cell- or multicolony-derived MIAMI cells (passage 3 to 9) were seeded at 2,500 cells/cm$^2$ in 35-mm dishes (Costar) coated with fibronectin (10 ng/ml-coated coverslips) in DMEM high glucose medium (DMEM-HG) supplemented with 20% FBS, 100 U/ml penicillin and 1 mg/ml streptomycin and cultured for 24 hours. Neural specification (step 1) was induced by exposing cells to DMEM-HG supplemented with 20% FBS and 10 ng/ml b-FGF for 24 hours. At the end of the neural specification treatment cells were washed twice with PBS, and then neuronal commitment (step 2) was induced by exposing the cells to DMEM-HG supplemented with 1 mM β-mercaptoethanol (βME) and 30 ng/ml NT-3 for 2 days. Finally, neural differentiation (step 3) was induced by first washing the cells twice with PBS and then exposing the cells to 200 µM butylated hydroxyanisole (BHA, Sigma), 25 mM KCl, 2 mM valproic acid, 4 µM forskolin, 1 µM hydrocortisone, 5 µM insulin, NT-3 (30 ng/ml), NGF (10 ng/ml), and BDNF (50 ng/ml) in DMEM-HG for 3 to 7 days.

f. Immunocytochemistry

For staining of cytoskeletal proteins at the indicated times, cells were rinsed twice with cold Dulbecco's phosphate-buffered saline (DPBS), pH 7.4, fixed with methanol at −20° C. for 2 min and then permeabilized with 0.1% Triton X-100 for 10 min. For other intracellular molecules, cells were fixed with 4% paraformaldehyde at 4° C. for 10 min and then permeabilized with 0.1% Triton X-100 for 10 min. For cell surface receptors, cells were fixed with 4% paraformaldehyde at 4° C. for 10 min. Slides were blocked for 30 min. Blocking solution consisted of PBS, 1% bovine serum albumin (BSA), and 1% serum (Sigma) from the species in which the secondary antibody was raised. Slides were then incubated sequentially for 30 min each with secondary specific antibodies, followed by incubation with HRP-, FITC- or rhodamine-conjugated antimouse or isotypic IgG antibody. Between each step, slides were washed with PBS plus 0.3% BSA. Specific immunostaining was demonstrated in control experiments in which cells were exposed to primary isotypic antibodies and then incubated with conjugated antibodies. DAPI (4′, 6-diamidino-2-phenylindole dihydrochloride) was present in the mounting solution. A Nikon microscope (connected to a Retiga 1300 color digital camera and imaging system) or a confocal fluorescence microscope (Zeiss LSM 510 laser scanning confocal microscope) was used to examine the cells. Cells with neural morphological characteristics were expressed as a percentage of total MIAMI cells counted A the standard deviation (percentage of total MIAMI cells±SD).

g. Electrophysiological Studies of MIAMI-Derived Neural Cells

MIAMI cells not treated or treated with the neural differentiation protocol for different periods of time were subjected to electrophysiological studies as follows.

Whole-cell patch-clamp techniques were used to record from cells maintained at 21-23° C. The methods used were similar to those earlier described (Valeyev et al., *J. Neurophysiol.*, 82:1-9, 1999). Thin glass pipettes (with filament, 1.5 mm OD; WPI, Sarasota, Fla.) pulled by a Flaming Brown micropipette puller (Sutter Instruments, San Rafael, Calif.) were utilized. Series resistance was less than 10 MΩ and was 50 to 70% compensated. The voltage error was less than 5 mV before breaking the patch. Whole-cell currents were monitored via an Ag/AgCl wire with Axopatch 200A amplifier (Axon Instruments, Foster City, Calif.) in the resistive-headstage mode, and recorded on to a computer hard drive for analysis with pClamp software (Version 8.2, Axon Instruments). The holding membrane potential was −70 mV.

The ionic composition of the inside (intracellular) and outside (bath solutions) changed in different experiments. Initially, in order to observe all currents the cells were bathed in a solution of 140 mM NaCl, 5 mM KCl, 2 mM CaCl$_2$, 1 mM MgCl$_2$, 5 mM N-2-hydroxy-ethylpiperazine-N'2-ethane-sulfonic acid (HEPES), and 10 mM D-glucose, titrated to pH 7.35 with NaOH. Osmolarity was adjusted with sucrose, if needed, to 310 mosmol/kg. Patch pipettes for whole cell recording were filled with a solution of 130 mM KCl, 2 mM MgCl$_2$, 0.1 mM CaCl$_2$, 1.1 mM ethylene-glycol-bis(β-aminoethyl ether)-N,N,N',N'-tetraacetic acid (EGTA), 5 mM ATP, and 10 mM HEPES, buffered to pH 7.15 with KOH. Osmolarity was adjusted, if needed, with sucrose to 290 mosmol/kg. In order to study sodium currents in the absence of potassium currents the cells were bathed in 140 mM NaCl, 5 mM CsCl, 0.1 mM CaCl$_2$, 1 mM MgCl$_2$, 5 mM HEPES, and 10 mM D-glucose, titrated to pH 7.35 with NaOH while the intracellular solution contained 130 mM CsCl, 2 mm MgCl$_2$, 0.1 mM CaCl$_2$, 1.1 mM EGTA, 5 mM ATP, and 10 mM HEPES, buffered to pH 7.15 with CsOH.

2. Uninduced MIAMI Cells Lack Neural Features

Cultures of MIAMI cells grown in parallel but not exposed to neuro-inductive conditions did not develop any of the features of neural cells. A few (5-10%) MIAMI cells expressed low levels of nestin (FIG. 8A) early in the culture period. As cells reached confluence, nestin expression was not detected. MIAMI cells did not react with antibodies against GFAP, NSE, class III β-tubulin, neurofilament M (160 kD, NF-M), neurofilament L (68 kD, NF-L), NGF-receptor (TrkA), and neuronal nuclear protein (NeuN). Specific immunostaining was demonstrated in experiments in which human fetal neuroepithelial precursor cells (McCarthy et al., *J. Hum. Virol.*, 3:215-228, 2000) were used as positive controls (for nestin see FIG. 8E) or in experiments in which primary isotypic antibodies were used as negative controls (for nestin see FIG. 8F).

3. Differentiation of MIAMI Cells to Neuron-Like Cells

Within 24 hours of plating, the MI cells (passage 3 to 9; FIG. 9A) were exposed to neural specification medium (Step 1; bFGF). Some of the cells (30-40%) acquired a more spherical shape. At this stage 90% of the cells strongly stained for nestin (FIG. 8B), 70-80% of the neural-like cells expressed neuron specific enolase (NSE, FIG. 10C) and 30-40% expressed GFAP (FIG. 10B). All cells were negative for neuron-specific class III β-tubulin (TuJ1), TrkA, NF-L, NF-M, and NeuN. After a 24-hour period of neural specification treatment, b-FGF was withdrawn and the cells were exposed to the neuronal commitment (Step 2; NT-3/βME) treatment for 2 days. Most of the cells (80%) acquired the bipolar spindle shape characteristic of neural cells progressively over the first 5 hours (FIG. 9B). The cell bodies became increasingly spherical and refractile with time in culture (FIG. 9C). Nestin was still strongly detected in the majority of the cells developing processes (FIG. 8C) shortly after initiation of treatment; however, toward the end of the treatment period the expression of nestin significantly decreased (FIG. 8D). Expression of neuron-specific class III β-tubulin (FIG. 10E) and TrkA (FIG. 10D) was detected in a fraction (40-50%) of these cells. At this point the membrane resting potential ranged from −40 to −57 mV (n=10 cells). No activation potential could be observed. Omission of NT-3 from the neuronal commitment step resulted in a decrease in the number of viable cells by more than two fold. It also decreased the number of cells expressing class III β-tubulin, the level of expression per cell of this neural marker, and resulted in a significant loss of the resting membrane potential which ranged between −10 and −16 mV.

When neural differentiation (step 3; NT-3/NGF/BDNF) was induced for 3 to 7 days, the cells further developed their neural morphology with a typical neural perikaryal appearance (FIG. 9D), and expressed NeuN FIG. 10G) and NF-L (FIG. 10F). Expression of nestin was not detected, consistent with a mature neural phenotype. Omission of NT-3 from the neural differentiation conditions significantly decreased the number of cells expressing mature neural markers (NeuN and neurofilament) and the level of expression of these markers. Moreover, NT-3 promoted the development of morphological features of neurons, such as a more complex neurite outgrowth and arborization (FIG. 11B-E) and was useful for the development of electrophysiological properties in MIAMI-derived neural cells. Furthermore, NT-3 treatment significantly increased the number of branching points (Table 9) and length of neurites (FIG. 11C-D).

TABLE 9

Effect of NT-3 on Cell Morphology after Neural Differentiation

|  | −NT 3 | +NT 3 |
| --- | --- | --- |
| Neuron-like morphology | 30-40% | 75-90% |
| Branching points per neuron-like cell[†] | 2.9 ± 1.2 [0-5] | 7.1 ± 1.5* [3-10] |

Average of 6 visual fields
[†]Mean ± S.D. [RANGE] n = 20
*p = 0.05 compared to untreated The electrophysiological properties of these cells at this stage resembled those of mature neurons. The whole cell resting membrane potential of the cells when KCl was present in the outside and inside solutions was within a range of −45 to −60 mV. The capacitance was in the order of 5-8 pF. As noted above, a holding potential of −70 mV was used. As seen in FIG. 12A depolarizing voltage steps of 10 mV were applied to the cell in order to observe evoked currents. The MIAMI-derived neural cells displayed both inward and outward currents upon depolarization similar to those observed in normal neurons.

CsCl replaced KCl in the bath and pipette solutions in order to observe isolated sodium currents. This also lowered the leakage currents and permitted better compensation of leakage currents and membrane capacity. FIG. 12B is an example of sodium-activated inward currents ($I_{Na}$) produced in response to depolarization steps when stem cells were at negative holding membrane potentials. Note that the amplitude of the inward current was dependent on the size of the voltage steps.

MIAMI cells isolated from donors of various ages (#519 [3-year-old male], #869 [55-year-old male], #812 [72-year-old male], and #889 [59-year-old female]), were used for the neural differentiation experiments described in this example and all responded in a similar fashion.

Single-cell-derived colonies from MIAMI cells isolated from sample #519, a 3-year-old male, were expanded under conditions described in this example and tested for their ability to differentiate toward the ectodermal-derived neural phenotype. These cells responded to neural differentiation in a manner similar to that described for non-clonal MIAMI cell populations. Development of the morphological characteristic, sequential expression of neural proteins, and acquisition of resting membrane potential within a range of −45 to −60 mV was consistently observed (70-90%). However, acquisition of inward and outward currents was observed only in about 20% of the time within 7-10 days of initiating the neural induction of MIAMI cells isolated from donors of all ages. Exposing human marrow stromal cells, not selected for expansion of MIAMI cells, to the neural-differentiation protocol here described resulted only in the low level expression of certain markers (nestin, GFAP, class III β-tubulin, and neuron specific enolase) by a fraction (10-50%) of the cells and in some cases to the development of a resting membrane potential reaching up to −16 mV (n=20).

4. Discussion

This example describes for the first time that a subpopulation of human bone marrow-derived stromal cells, the MIAMI cells, can be induced to differentiate into cells with morphological, phenotypical, and functional characteristics of central nervous system mature neurons.

The sequential expression of markers of MIAMI cells undergoing neural differentiation is reminiscent of the neural developmental program described for neural stem cells in vivo and in vitro (Taupin and Gage, *J. Neurosci. Res.*, 69:745-749, 2002; McKay, *Science*, 276:66-71, 1997; Zimmerman et al., *Neuron* 12:11-24, 1994; Messam et al., *Exp. Neurol.*, 161:585-596, 2000). Similar to neurons derived from embryonic stem cells and neural stem cells (NSCs) in vitro, MIAMI-derived neural cells exhibit electrophysiological properties of bona fide neurons.

NSCs divide symmetrically to enrich the NSCs pool of the subventricular zone (self renewing) or asymmetrically to generate differentiated progeny that lose their attachment to the base lamina and rapidly migrate to their specific location (Cai et al., *J. Neurosci.*, 17:2088-2100, 1997). These differentiated progeny, also called restricted precursors, acquire specific differentiation markers while migrating and can be distinguished from stem cells by such expression. The neuron-restricted precursors express essentially nestin, neuron-specific class III β-tubulin, and polysialylated NCAM (PSA-NCAM). After neural differentiation and migration to the cortex they mainly express neurofilament and NeuN, they develop electrical activity, and they synthesize and respond to neurotransmitters. NSCs can be isolated based on their dependence on b-FGF for growth (Shihabuddin et al., *Exp. Neurol.*, 148:577-586, 1997) and b-FGF appears to be a prerequisite for neural differentiation (Kennea and Mehmet, *J. Pathol.*, 197:536-550, 2002; Craig et al., *J. Neurosci.*, 16:2649-2658, 1996).

Similarly, neural specification (Step 1) of competent MIAMI cells is promoted by b-FGF which leads to the upregulation of nestin expression MIAMI cells express NTRK-3 and it has been reported that treatment of NSCs with NT-3 promotes neural maturation (Takahashi et al., *J. Neurobiol.*, 38:65-81, 1999). Progression of induced MIAMI cells toward a neural phenotype was assisted by subsequent exposure to NT-3 (Step 2). This neuronal commitment step induced the expression of neuron-specific class III β-tubulin and TrkA with the paralleled decrease in nestin expression, a phenotype consistent with that of a neural precursor cell (Messam et al., *Exp. Neurol.*, 161:585-596, 2000). Final neuronal differentiation (Step 3) of MIAMI cells was promoted by simultaneous treatment with the neurotrophic factors NT-3, NGF, and BDNF, factors known to support differentiation and survival of neurons (Barnabe-Heider and Miller, *J. Neurosci.*, 23:5149-5160, 2003; Park et al., *J. Neurosci.*, 19:10383-10389, 1999). Neuronal differentiation of MIAMI cells is demonstrated by the expression of NeuN, neurofilament, neuronal morphology, extensive neurite growth and arborization, and acquisition of electrophysiological properties indistinguishable from bona fide neurons.

Uniquely, MIAMI-derived neurons developed neuronal electrophysiological properties without the need for co-culture with astrocytes as published for rat bone marrow derived cells (Jiang et al., *Proc. Natl. Acad. Sci. USA,* 100(Supp 1): 11854-11860, 2003) and other brain-derived stem cells (Song et al., *Nature,* 417:39-44, 2002; Wagner et al., *Nat. Biotechnol.,* 17:653-659, 1999). This demonstrates that differentiation of human MIAMI cells to neurons can be achieved without any type of co-culture. In other examples, co-culturing with primary astrocytes may further enhance the efficiency and extent of neuronal differentiation of MIAMI cells.

This example further demonstrates that marrow stem cells can differentiate to a functionally mature neuronal phenotype without the need for fusion with precursor cells of the neuroectodermal lineage.

MIAMI cells are capable of differentiating into cells that express neuronal proteins, maintain a neuronal morphology, and respond to neurotrophic factors. Acquisition of electrophysiological characteristics is clear evidence that MIAMI-derived neuronal cells are genuine neurons. The cells maintained a resting membrane potential and depolarizing voltage steps activated ion currents. In cells with the potassium currents blocked, the inward current displayed the characteristics of fast neuronal sodium currents.

Acquisition of electrophysiological properties in cells derived from MIAMI cells was assisted by NT-3 treatment MIAMI cells are derived from MSCs after selection/expansion under low oxygen conditions as described in Example 1. Since the more primitive marrow stem cells are thought to be maintained at low oxygen tension in vivo (Danet et al., *J. Clin. Invest.,* 112:126-135, 2003; Chow et al., *Biophys. J.,* 81:675-684, 2001; Lord, In: *Concise Reviews in Clinical and Experimental Haematology* (ed, Murphy, M., Jr.), Dayton, Ohio: AlphaMed Press, 1992), low oxygen tension may represent a factor in the selection of early progenitor cells capable of maintaining their potential to develop into cells of the neuroectodermal lineage. Furthermore, it has been shown that decreased oxygen levels promoted the survival and proliferation of a population of mammalian neural stem cells (Morrison et al., *Cell,* 96:737-749, 1999). The addition of NT-3 facilitated neuronal differentiation in this example even when two other neurotrophic factors, BDNF and NGF, were present. This suggests that specific signals mediated by NTRK-3 were useful for inducing the development of a more complex arborization pattern and the acquisition of the electrophysiological properties of neurons. It has recently been reported that anti-NT-3 neutralizing antibodies decreased the survival and differentiation of cortical progenitors (Barnabe-Heider and Miller, *J. Neurosci.,* 23:5149-5160, 2003).

MIAMI cells from young and old individuals can serve as a starting material to generate functional neurons because this can be accomplished in vitro without co-culture with other cell types. Since the neuronal differentiation of MIAMI cells resembles that of NSCs, this example demonstrates that MIAMI cells could also serve as a starting material to generate oligodendrocytes for the treatment of damaged, diseased, or aged neural tissue, such as occur in multiple sclerosis.

While this disclosure has been described with an emphasis upon particular embodiments, it will be obvious to those of ordinary skill in the art that variations of the particular embodiments may be used and it is intended that the disclosure may be practiced otherwise than as specifically described herein. Accordingly, this disclosure includes all modifications encompassed within the spirit and scope of the disclosure as defined by the following claims:

We claim:

1. A composition comprising isolated, post-natal, multilineage-inducible cells, which (i) express at least CD29, CD 81, CD90, CD122, and CD164; and (ii) do not express CD13.

2. The composition of claim 1, wherein the cells further express at least one of hepatocyte growth factor receptor (c-Met), bone morphogenetic protein receptor type IB (BMP-receptor 1B), or neurotrophic tyrosine kinase receptor type (NTRK3).

3. The composition of claim 1, wherein the cells are isolated from a biological sample comprising bone marrow, vertebral bodies, peripheral blood, umbilical cord blood, iliac crest aspirate, fat, cartilage, muscle, skin, bone, teeth, liver, brain, or mixtures thereof.

4. The composition of claim 3, wherein the biological sample comprises bone marrow.

5. The composition of claim 1, wherein the cells are isolated from a mammal.

6. The composition of claim 5, wherein the mammal is a human.

7. The composition of claim 6, wherein the mammal is a postmortem subject.

8. A pharmaceutical composition comprising multilineage-inducible cells of claim 1 in a pharmaceutically acceptable carrier.

9. The composition of claim 1, wherein the cells do not express markers comprising CD36, CD49b, CD71, or CD133.

10. A composition comprising isolated, post-natal, multi-lineage-inducible cells, which (i) express at least CD29, CD81, CD90, CD122, and CD164; and (ii) do not express CD34.

11. The composition of claim 8, wherein the cells further express at least one of hepatocyte growth factor receptor (c-Met), bone morphogenetic protein receptor type IB (BMP-receptor 1B), or neurotrophic tyrosine kinase receptor type 3 (NTRK3).

12. The composition of claim 10, wherein the cells do not express markers comprising CD36, CD49b, CD71, or CD133.

13. The composition of claim 10, wherein the cells are isolated from a biological sample comprising bone marrow, vertebral bodies, peripheral blood, umbilical cord blood, iliac crest aspirate, fat, cartilage, muscle, skin, bone, teeth, liver, brain, or mixtures thereof.

14. The composition of claim 13, wherein the biological sample comprises bone marrow.

15. The composition of claim 10, wherein the cells are isolated from a mammal.

16. The composition of claim 15, wherein the mammal is a human.

17. The composition of claim 15, wherein the mammal is a postmortem subject.

18. A kit, comprising a container containing a purified population of the multilineage-inducible cells of claim 10.

19. The kit of claim 18, further comprising a container containing a growth factor, a container containing a culture medium, instructions for using the kit, or a combination thereof.

20. A pharmaceutical composition comprising multilineage-inducible cells of claim 10 in a pharmaceutically acceptable carrier.

21. A method of inducing osteogenic differentiation of the multilineage-inducible cells of claim 10, comprising culturing the multilineage-inducible cells in an osteogenic medium, wherein osteogenic differentiation is induced in the multilineage-inducible cells.

22. The method of claim 21, wherein the osteogenic medium comprises ascorbic acid 2-phosphate, β-glycerophosphate, and dexamethasone.

23. The method of claim 21, further comprising placing the multilineage-inducible cells in a cell culture container, and adding dexamethasone to the osteogenic medium after a portion of the multilineage-inducible cells adhere to the cell culture container.

24. The method of claim 21, wherein osteogenic differentiation comprises expression of Runx2, osteocalcin, collagen I α1, or bone sialoprotein in the multilineage-inducible cells.

25. A method of inducing chondrogenic differentiation of the multilineage-inducible cells of claim 10, comprising culturing multilineage-inducible cells in a serum-free, chondrogenic medium to induce chondrogenic differentiation, wherein the chondrogenic medium comprises dexamethasone, TGF-β3, ascorbic acid 2-phosphate, sodium pyruvate, proline, insulin, transferrin, and selenous acid.

26. The method of claim 25, further comprising suspending the cells in the serum-free, chondrogenic medium and pelleting the cells in a tube.

27. The method of claim 26, further comprising culturing the cells for at least about 4 to 6 weeks.

28. The method of claim 25, wherein chondrogenic differentiation comprises expression of collagen in the multilineage-inducible cells.

29. A method of inducing adipogenic differentiation of the multilineage-inducible cells of claim 10, comprising culturing said multilineage-inducible cells in an adipogenic medium to induce adipogenic differentiation, wherein the adipogenic medium comprises hydrocortisone, isobutylmethylxanthine, and indomethacine.

30. The method of claim 29, wherein adipogenic differentiation comprises expression of lipoprotein lipase or peroxisome proliferators-activated receptor y-2 in the multilineage-inducible cells.

31. A method of inducing neural differentiation of the multilineage-inducible cells of claim 10, comprising in the following order:
  (a) contacting said cells with a first culture medium comprising basic fibroblast growth factor (bFGF);
  (b) contacting the cells with a second culture medium comprising β-mercaptoethanol (βME) and neurotrophin-3 (NT-3); and
  (c) contacting the cells with a third culture medium comprising NT-3, β-nerve growth factor (NGF), and brain-derived neurotrophic factors (BDNF);
  wherein neural differentiation is induced in the multilineage-inducible cells.

32. The method of claim 31, further comprising plating the cells at low density in a cell culture container, comprising an ECM substrate, prior to step (a).

33. The method of claim 32, wherein the ECM substrate comprises fibronectin, collagen, laminin, vitronectin, polylysine, heparan sulfate proteoglycans, entactin, or a combination thereof.

34. The method of claim 31, wherein step (b) has a duration of up to about 48 hours.

35. The method of claim 31, wherein step (c) has a duration of up to about 2 days.

36. The method of claim 31, wherein step (d) has a duration of up to about 14 days.

37. A method of inducing endodermal differentiation of the multilineage-inducible cells of claim 10, comprising in the following order:
  (a) contacting said cells to a first culture medium comprising bFGF;
  (b) contacting the cells to a second culture medium comprising DMSO, butylated hydroxyanisole (BHA), and exendin-4;
  (c) contacting the cells to a third culture medium comprising b-FGF, EGF, and exendin-4; and
  (d) contacting the cells to a fourth culture medium comprising nicotinamide, HGF, exendin-4, and activin-A;
  wherein endodermal differentiation is induced in the multilineage-inducible cells.

38. The method of claim 37, further comprising plating the cells at low density prior to step (a).

39. The method of claim 37, wherein the cells are contacted with the first culture medium for up to about 24 hours.

40. The method of claim 37, wherein the cells are contacted with the second culture medium for up to about 24 hours.

41. The method of claim 37, wherein the cells are contacted with the third culture medium for up to about 4 days.

42. The method of claim 37, wherein the cells are contacted with the fourth culture medium for up to about 14 days.

43. A method of identifying a differentiation-inducing agent comprising:
  (a) providing multilineage-inducible cells of claim 10;
  (b) contacting the cells with the agent; and
  (c) observing the effect of the agent on the cells, wherein differentiation of the cells identifies the agent as differentiation inducing.

44. The method of claim 43, wherein differentiation of the cells comprises assaying expression of an osteogenic marker, a chondrogenic marker, an adipogenic marker, a neural marker, an endodermal marker, or a combination thereof.

45. The method of claim 43, wherein differentiation of the cells comprises assaying a functional property of an osteogenic cell, a chondrogenic cell, an adipogenic cell, a neural cell, or a β-cell.

46. A method of isolating multilineage-inducible cells comprising:
  (a) culturing a cell population isolated from a biological sample comprising bone marrow, vertebral bodies, peripheral blood, umbilical cord blood, iliac crest aspirate, fat, cartilage, muscle, skin, bone, teeth, liver, brain or mixtures thereof, under low-oxygen conditions to produce adherent cells and non-adherent cells;
  (b) removing the non-adherent cells from the cultured cell population; and
  (c) expanding the adherent cells, wherein the adherent cells comprise multilineage-inducible cells, which (i) express at least CD29, CD81, CD90, CD122, and CD164; and (ii) do not express CD13 or CD34.

47. The method of claim 46, wherein the biological sample is collected from a post-natal subject.

48. The method of claim 47, wherein the post-natal subject is a human.

49. The method of claim 46, wherein the biological sample is collected from a postmortem subject.

50. The method of claim 46, wherein low-oxygen conditions comprises no more than about 3% oxygen.

51. The method of claim 46, wherein the adherent cells and the non-adherent cells are co-cultured for at least 7 days.

52. The method of claim 51 further comprising placing the cells in a cell culture container, wherein the cell culture container comprises an extracellular matrix (ECM) substrate.

53. The method of claim 52, wherein the ECM substrate comprises fibronectin, collagen, laminin, vitronectin, polylysine, heparan sulfate proteoglycans, entactin, or a combination thereof.

54. A cell isolated by the method of claim 46, wherein the cell is a multilineage-inducible cell.

55. The method of claim 46, wherein the multilineage-inducible cells do not express CD13.

56. The method of claim 46, wherein the multilineage-inducible cells do not express CD34.

57. Isolated post-natal, multilineage inducible mammalian cells, which express (i) at least CD29, CD81, CD90, CD122, and CD164; but do not express (ii) CD13 or CD34.

58. The cells of claim 57, wherein the cells further express at least one of hepatocyte growth factor receptor (c-Met), bone morphogenetic protein receptor type IB (BMP-receptor 1B), or neurotrophic tyrosine kinase receptor type 3 (NTRK3).

59. The cells of claim 57, wherein the cells further express at least stage-specific embryonic antigen 4 (SSEA4), Oct-4, and Rex-1.

60. The cells of claim 58, wherein the cells further express at least stage-specific embryonic antigen 4 (SSEA4), Oct-4, and Rex-1.

61. The cells of claim 57, wherein the cells expresss CD10 but do not express CD13.

62. The cells of claim 57, wherein the cells are from a biological sample selected from the group consisting of bone marrow, peripheral blood, and umbilical cord blood.

63. The cells of claim 57, wherein the cells are post-natal, multilineage-inducible human cells.

64. A pharmaceutical composition comprising multilineage-inducible cells of claim 54 in a pharmaceutically acceptable carrier.

* * * * *